(12) United States Patent
Albaneze-Walker et al.

(10) Patent No.: US 7,312,334 B2
(45) Date of Patent: Dec. 25, 2007

(54) METHOD OF PREPARING INHIBITORS PHOSPHODIESTERASE-4

(75) Inventors: Jennifer Albaneze-Walker, Westfield, NJ (US); Jerry Anthony Murry, New York, NY (US); Arash Soheili, Iselin, NJ (US); Shawn A. Springfield, Hoboken, NJ (US)

(73) Assignee: Merck & Co. Inc., Rahway, NJ (US)

( * ) Notice: Subject to any disclaimer, the term of this patent is extended or adjusted under 35 U.S.C. 154(b) by 354 days.

(21) Appl. No.: 10/530,465

(22) PCT Filed: Nov. 18, 2003

(86) PCT No.: PCT/US03/36806

§ 371 (c)(1),
(2), (4) Date: Apr. 5, 2005

(87) PCT Pub. No.: WO2004/048377

PCT Pub. Date: Jun. 10, 2004

(65) Prior Publication Data

US 2006/0019981 A1    Jan. 26, 2006

Related U.S. Application Data

(60) Provisional application No. 60/428,315, filed on Nov. 22, 2002.

(51) Int. Cl.
    *C07D 471/02*    (2006.01)

(52) U.S. Cl. ..................................... 546/123; 546/122
(58) Field of Classification Search ................ 546/122, 546/123
    See application file for complete search history.

(56) References Cited

U.S. PATENT DOCUMENTS

| 4,220,646 A | 9/1980 | Cotrel et al. |
| 6,677,351 B2 | 1/2004 | Li et al. |
| 6,743,802 B2 * | 6/2004 | Guay et al. ................. 514/300 |

FOREIGN PATENT DOCUMENTS

DE    20 50 111    11/1975

OTHER PUBLICATIONS

J. Org. Chem., vol. 64, No. 16, pp. 6102-6105, 1999.
J. Org. Chem., vol. 64, pp. 6102-6105, 1999.
Journal of the American Chemical Society, vol. 121, No. 41, pp. 9550-9561, 1999.

* cited by examiner

*Primary Examiner*—Janet Andres
*Assistant Examiner*—Niloofar Rahmani
(74) *Attorney, Agent, or Firm*—Sylvia A. Ayler; William Krovatin

(57) ABSTRACT

In one aspect, the present invention is directed to a one pot method of preparing intermediates of Formula (V), which are useful in making inhibitors of phosphodiesterase-4: The present invention is also directed to a method of preparing phosphodiesterase inhibitors comprising the Formula (IX, IXa).

19 Claims, No Drawings

METHOD OF PREPARING INHIBITORS PHOSPHODIESTERASE-4

CROSS REFERENCE TO RELATED APPLICATIONS

This application is a U.S. National Phase application under 35 U.S.C. § 371 of PCT Application No. PCT/US03/36806, filed Nov. 18, 2003, which claims priority under 35 U.S.C. 119 to U.S. No. 60/428,315, filed Nov. 22, 2002.

BACKGROUND OF THE INVENTION

1. Field of the Invention

The present invention is directed to a method of preparing inhibitors of phosphodiesterase-4. In particular, this invention relates to a method of preparing compounds that are biaryl substituted 1,8-naphthyridin-4(1H)-ones.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, there by triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), Ann. Rep. In Med. Chem., 33:91-109(1998). B. Hughes et al., Br. J. Pharmacol., 118:1183-1191(1996); M. J. Perry et al., Cell Biochem. Biophys., 29:113-132(1998); S. B. Christensen et al., J. Med. Chem., 41:821-835(1998); and Burnouf describe the wide variation of the severity of the undesirable side effects exhibited by various compounds. As described in M. D. Houslay et al., Adv. In Pharmacol., 44:225-342(1998) and D. Spina et al., Adv. In Pharmacol., 44:33-89(1998), there is great interest and research of therapeutic PDE4 inhibitors.

International Patent Publication WO9422852 describes quinolines as PDE inhibitors. International Patent Publication WO9907704 describes 1-aryl-1,8-naphthylidin-4-one derivatives as PDE4 inhibitors.

A. H. Cook, et al., J. Chem. Soc., 413-417(1943) describes gamma-pyridylquinolines. Other quinoline compounds are described in Kei Manabe et al., J. Org. Chem., 58(24):6692-6700(1993); Kei Manabe et al., J. Am. Chem. Soc., 115(12):5324-5325(1993); and Kei Manabe et al., J. Am. Chem. Soc., 114(17):6940-6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

SUMMARY OF THE INVENTION

In one aspect, the present invention is directed to a one pot method of preparing intermediates of Formula V, which are useful in making inhibitors of phosphodiesterase-4:

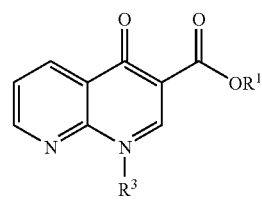

In a second aspect, the present invention invention is directed to a method of preparing compounds of Formula IX and Formula IXa which are inhibitors of phosphodiesterase-4:

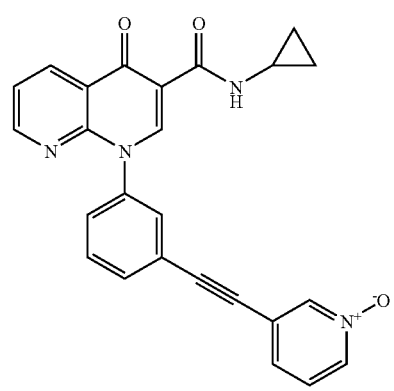

-continued

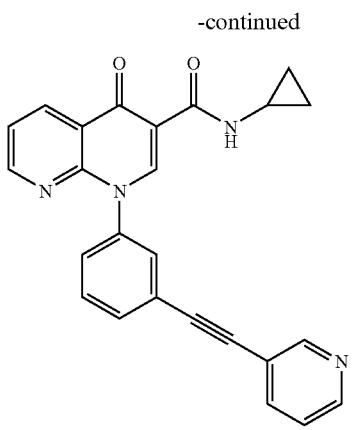

IXa

Inhibitors of phosphodiesterase-4 have been shown to be useful in the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues.

DETAILED DESCRIPTION OF THE INVENTION

In one embodiment the preparation of compounds of Formula IX may begin with the preparation of an intermediate of Formula V:

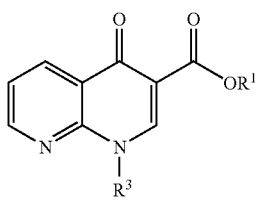

V wherein

—$OR^1$ is a suitable leaving group such as those disclosed in standard texts, such as: Protective Groups in Organic Synthesis, $2^{nd}$ edition, by Theodora W. Greene and Peter G M. Wuts (1991) and Protecting Groups, by Philip J, Kocienski (1994). For example, $R^1$ may be an optionally $C_{1-8}$alkyl, aryl, heteroaryl, wherein the substituents are selected from the group consisting of aryl, $C_{1-8}$ alkyl;

$R^3$ is $C_{1-8}$alkyl, aryl or heteroaryl, optionally mono, di-, tri- or tetra-substituted with Halo, $B(OH)_2$, —C≡CH, aryl, heteroaryl, $C_{1-10}$alkyl, alkoxy, ketone, alcohol, triflate, mesylate, amide, ester, ketone, acetal, phosphate, stannane, silyl, $B(OR)_2$ wherein R is $C_{1-8}$alkyl or aryl; comprising Step A: reacting, in a non-nucleophilic solvent, a compound of Formula II:

II wherein $R^2$ is each independently $C_{1-8}$alkyl, optionally mono or di-substituted with $C_{1-8}$alkyl, such as methyl or ethyl, or aryl, such as phenyl or heteroaryl;

with a compound of Formula I in the presence of a base:

I wherein $R^4$ is bromo or chloro, to yield a compound of Formula III.

III and,

Step B: reacting, in a non-nucleophilic solvent, a compound of Formula III with an amine compound of Formula IV $R^3$—$NH_2$     IV in the presence of a base to yield a compound of Formula V.

The definition for the non-nucleophilic solvent of Step B is as previously defined for Step A. Similarly, the definition for the base of Step B is as previously defined for Step A.

In Step A, the molar ratio of base to compound of Formula I can be varied from about 12:1 to about 3:1. A ratio of 8:1 is typical. A ratio lower than 3:1 may result in trimerization of the aminoacryate to give 1,3,5-tricarboxybenzene. The molar ratio of the compound of Formula I to compound of Formula II can be varied from 1:1 to 1:3; typically about 1:1.5. Reaction Step A may conveniently be conducted at a temperature range of 25 to 100° C.; or typically 40 to about 60° C. and is allowed to proceed until substantially complete in from 2 to 18 hours; typically 6 to 12 hours. Reaction Step B is carried out as described above.

Within this embodiment there is a genus wherein:

$R^1$ is an optionally $C_{1-8}$alkyl, aryl, heteroaryl, wherein the substituents are selected from the group consisting of aryl, $C_{1-8}$ alkyl;

$R^2$ is methyl or ethyl or phenyl;

$R^3$ is $C_{1-8}$alkyl, aryl or heteroaryl, optionally mono, di-, tri- or tetra-substituted with Halo, $B(OH)_2$, —C≡CH, aryl, heteroaryl;

Within this embodiment there is a genus wherein:

$R^1$ is methyl or ethyl;

$R^2$ is methyl;

$R^3$ phenyl substituted with halo, $B(OH)_2$, —C≡CH

Within this embodiment there is a genus wherein:

the non-nucleophilic solvent is selected from dimethylformamide, dimethylacetamide, tetrahydrofuran, ethylacetate, acetonitrile, toulene, benzene, dioxane, methylene chloride Within the genus immediately above there is a sub-genus wherein:

the non-nucleophilic solvent is acetonitrile.

Within this embodiment there is a genus sub-genus wherein:

the base is selected from sodium or potassium carbonate, triethylamine, diethylamine, and Huenigs base.

Within this embodiment there is a genus wherein:

the base is selected from sodium carbonate or triethylamine.

Within this embodiment there is a genus wherein:

the molar ratio of compound of Formula IV to compound of Formula iii is about 2:1 to 1:2.

Within the genus immediately above there is a sub-genus wherein:

the molar ratio of the compound of Formula IV to the compound of Formula III is about 1:1.

Within this embodiment there is a genus wherein:

the molar ratio of base to compound of Formula IV is at least 1:1.

Within the genus immediately above there is a sub-genus wherein:

the molar ratio of base to compound of Formula IV is about 1:1.

Within this embodiment there is a genus wherein:

the reaction is conducted at a temperature range of about 20 to 100° C.

Within the genus immediately above there is a sub-genus wherein:

the reaction is conducted at a temperature range of about 40 to about 50° C.

In a second embodiment there is a method of preparing a compound of Formula V

V wherein

—$OR^1$ is a suitable leaving group;

$R^3$ is $C_{1-8}$alkyl, aryl or heteroaryl, optionally mono, di-, tri- or tetra-substituted with Halo, $B(OH)_2$, —C≡CH (alkyne), aryl, heteroaryl, $C_{1-10}$alkyl, alkoxy, ketone, alcohol, triflate, mesylate, amide, ester, ketone, acetal, phosphate, stannane, silyl, $B(OR)_2$ wherein R is C1-8alkyl or aryl;

comprising

Step A: reacting, in a non-nucleophilic solvent, a compound of Formula II:

II wherein $R^2$ is each independently $C_{1-8}$alkyl, optionally mono or di-substituted with $C_{1-8}$alkyl, such as methyl or ethyl, or aryl or heteroaryl;

with a compound of Formula I in the presence of a base:

I wherein $R^4$ is bromo or chloro to yield a compound of Formula III.

III and,

Step B: reacting, in a non-nucleophilic solvent, a compound of Formula III with an amine compound of Formula IV

R³—NH₂     IV in the presence of a base to yield a compound of Formula V.

Within this second embodiment there is a genus wherein:
R¹ is an optionally C$_{1-8}$alkyl, aryl, heteroaryl, wherein the substituents are selected from the group consisting of aryl, C$_{1-8}$ alkyl;
R² is methyl or ethyl or phenyl;
R³ is C$_{1-8}$alkyl, aryl or heteroaryl, optionally mono, di-, tri- or tetra-substituted with Halo, B(OH)$_2$, —C≡CH, aryl, heteroaryl;

Within this second embodiment there is a genus wherein:
R⁴ is chloro.

Within this second embodiment there is a genus wherein:
R¹ is methyl or ethyl;
R² is methyl;
R³ phenyl substituted with halo, B(OH)$_2$, —C≡CH Within this second embodiment there is a genus wherein:
the non-nucleophilic solvent is selected from dimethylformamide, dimethylacetamide, tetrahydrofuran, ethylacetate, acetonitrile, toulene, benzene, dioxane, methylene chloride Within this genus there is a sub-genus wherein:
the non-nucleophilic solvent is acetonitrile.

Within this second embodiment there is a genus wherein:
the base is selected from sodium or potassium carbonate, triethylamine, diethylamine, and Huenigs base.

Within this genus there is a sub-genus wherein:
the base is selected from sodium carbonate or triethylamine.

Within this second embodiment there is a genus of Step A, wherein:
the molar ratio of base to compound of Formula I is about 12:1 to about 3:1.

Within this genus, there is a sub-genus of Step A, wherein:
the molar ratio of base to compound of Formula I is about 8:1 to 3:1.

Within this second embodiment, there is a genus of Step A, wherein:
the molar ratio of the compound of Formula I to compound of Formula II is about 1:1 to 1:3.

Within this second embodiment, there is a genus of Step A, wherein:
the reaction is carried out at about 25 to 100° C.

Within this second embodiment, there is a genus Step A, wherein:
The reaction is carried out at about 40 to about 60° C.

Within this second embodiment, there is a genus of Step B, wherein:
the molar ratio of compound of Formula IV to compound of Formula m is about 2:1 to 1:2.

Within this genus there is a sub-genus of Step B wherein:
the molar ratio of the compound of Formula IV to the compound of Formula m is about 1:1.

Within this second embodiment there is a genus of Step B, wherein:
the molar ratio of base to compound of Formula IV, is about 1:1 or more.

Within this genus, there is a sub-genus of Step B, wherein:
the molar ratio of base to compound of Formula IV is about 1:1.

Within this second embodiment there is a genus of Step B, wherein:
the reaction is conducted at a temperature range of about 20 to 100° C.

Within this genus there is a sub-genus of Step B, wherein:
the reaction is conducted at a temperature range of about 40 to about 50° C.

Within this second embodiment, there is a genus wherein:
reaction step A and Reaction Step B are carried out in a single pot without purification or isolation of the product of Step A prior to proceeding with Step B.

In another embodiment, the present invention is direct to a method of preparing a phosphodiesterase-4 inhibitor of Formula IX and IXa

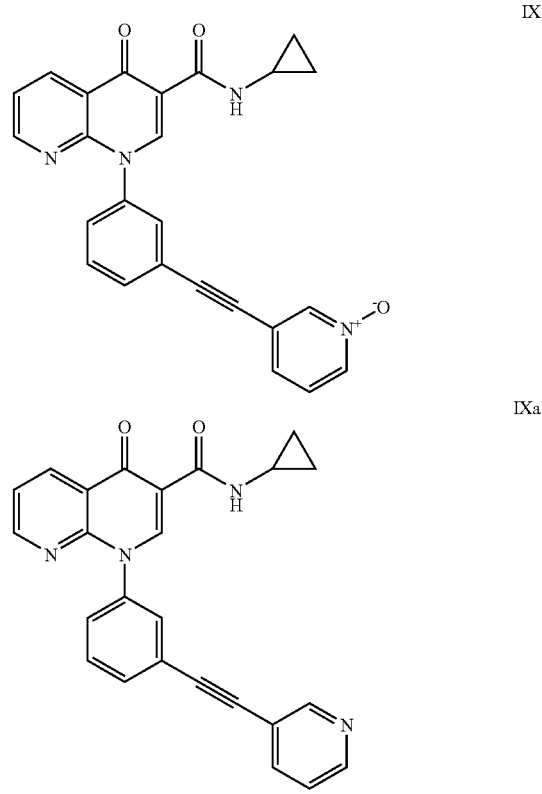

Comprising
Step C: reacting, in solvent A, a compound of Formula Va

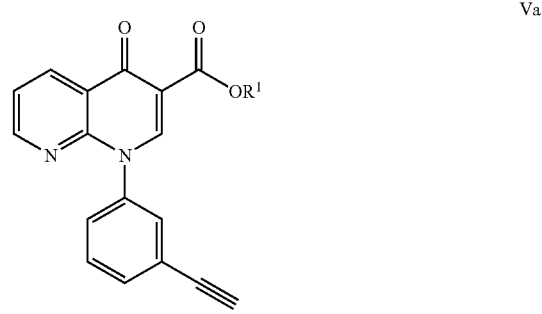

wherein
—OR¹ is a suitable leaving group such as those disclosed in standard texts, such as: Protective Groups in Organic Synthesis, 2$^{nd}$ edition, by Theodora W. Greene and Peter G M. Wuts (1991) and Protecting Groups, by Philip J, Kocienski (1994). For example, R$^1$ may be an optionally C$_{1-8}$alkyl, aryl, heteroaryl, wherein the substituents are selected from the group consisting of aryl, C$_{1-8}$ alkyl;

with a compound of Formula VII or VIIa

VII

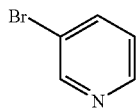

VIIa in the presence of a palladium catalyst and a phosphine ligand in the amine base to yield a compound of Formula VIII or VIIIa

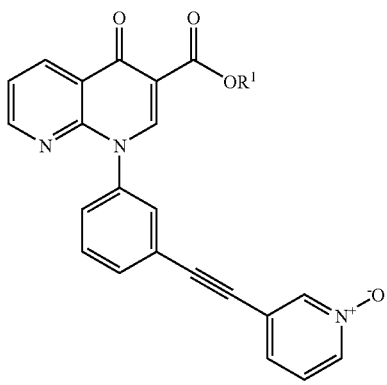

VIII

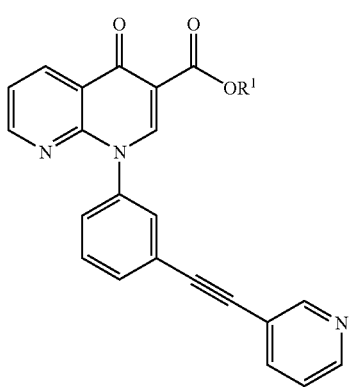

VIIIa

A preferred compound of Formula Va and Formula VIII and VIIIa, respectively, are as follows:

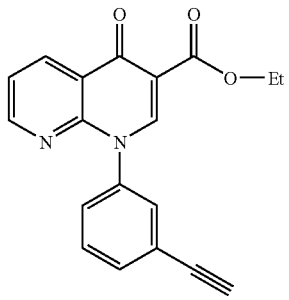

Va

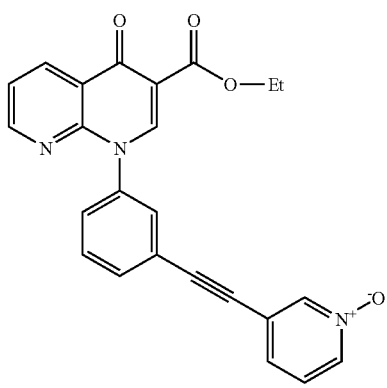

VIII

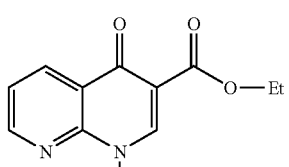

VIIIa

For purposes of this specification, solvent A is selected from the group consisting of dimethylaminoacetamide, dimethylformamide, acetonitrile, DMSO, methylacetamide, ethers or mixtures thereof. For purposes of this specification, the phosphine ligand is selected from the group consisting of P(C$_{1-6}$alkyl)$_3$, such as P(t-butyl)$_3$, P(Cy)$_3$, and P(t-butyl)$_2$ (biphenyl). For purposes of this specification, the palladium catalyst includes Fu's catalyst (i.e. P(t-butyl)$_3$-Pd—P(t-butyl)$_3$), [PdCl(allyl)]$_2$, Pd$_2$ (dba)$_3$, and [P(t-butyl)$_3$PdBr]$_2$ (Johnson-Matthey catalyst). For purposes of this specification, the amine base is a hindered amine base such as t-amylamine, t-butylamine, isopropylamine, or diisopropylamine.

In Step C, the molar ratio of the compound of Formula Va to Formula VII or VIIa may vary widely, but is optimally about 1:1.5 to 1.5:1 and is typically approximately 1:1. As a general principle, at least 1 molar equivalent of base per mole of Compound of Formula Va plus the 1 molar equivalent of base per molar equivalent of the compound of Formula VII or VIIa is desirable. Reducing this ratio reduces the yield. Thus, in the reaction above the ratio of amine base to compound of Formula Va can be 1.2:1 or greater, but is typically 2:1 to 3.5:1. The ratio molar of Palladium to compound of Formula V 0.05:1 to 0.10:1. In the instance [PdCl(allyl)]$_2$, for example, which possesses two mole of palladium per mole of catalyst, the ratio would be 0.025:1 to 0.05:1. The molar ratio of phosphine ligand to palladium is typically 3:1 to 5:1, often approximately 4:1. The reaction can be carried out a 25 to 125° C., more typically 40-70° C., and is allowed to proceed until the reaction is substantially complete. The presence of oxygen is minimized by purging the reaction vessel with nitrogen gas prior to addition of the reagents.

The product of Step C is cooled to 0 to about 5° C. Thereafter 3-6 volumes of anti-solvent per volume of solvent is added to the product of Step C to precipitate compound of Formula VIII or VIIIa. For purposes of this specification, the anti-solvent is defined as a non-reactive solvent in which compound of Formula VIII or VIIa will precipitate.

The slurry comprising the precipitated compound of Formula VIII or VIIIa is filtered or centrifuged. The filter or centrifuge cake comprising the compound of Formula VIII or VIIIa is re-slurried or directly washed with isobutanol or isopropanol to remove residual palladium. For example, the filter cake comprising compound of Formula VIII or VIIIa may be washed in situ (i.e. on the filter press) with 40 to 60 volumes of isobutanol unit weight of dry compound of Formula VIII or VIIIa.

As an alternative, residual palladium may be removed by re-dissolving compound of Formula I in an $C_{1-6}$alkanol solvent (such as methanol, ethanol or propanol) and subjecting the slurry comprising the compound of Formula IX or IXa to an activated carbon such as Darco G-60 or Ecosorb. The slurry is then filtered to remove the activated carbon. As may be appreciated, it is convenient to increase the solubility of the product in the alkanol solvent by warming the alkanol (such as to 25 to 70° C.) either before or after contact with the product. Typically, the slurry is kept warm for 1 to 6 hours, and filtered while still warm.

In function, the overall transformation achieved in step C is the same as that of a typical Sonogashira coupling reaction. As such, Step C is an efficient, one step method of coupling an alkyne to an aryl halide. On the other hand, step C differs from a Sonogashira coupling reaction in several important ways. For example, the Sonogashira coupling reaction typically requires the use of a copper, zinc, magnesium or zirconium reagent in addition to a palladium catalyst. Copper is preferred. However, applicants have found that Sonogashira coupling (Sonogashira, K. in Metal-Catalyzed Cross-Coupling Reactions; Diederich, F. and Stang, P. eds; Wiley-VCH: Weinheim, Germany, 1998, Chapter 5. See also, Littke, A. and Fu, G. Angew. Chem. Int. Ed. 1998,37, No. 24, pp 3387-3388; Wolfe, J. Singer, R., Yang, B and Buchwald, S., J. Am. Chem. Soc., 1999, 121, pp 9550-9561.) of compound of Formula Va and Formula VII results of the production of as much as 10% dimer of the compound of Formula Va in the product.

Hermann, et. al. (*Eur. J. Chem* 2000, 3679-3681), reported that if the palladium catalyst is judiciously chosen, the need for copper can be obviated. $P(Cy)_3$-Pd—$P(Cy)_3$ and $P(t\text{-butyl})_3$-Pd—$P(t\text{-butyl})_3$ (Fu's catalyst), are two of such catalysts. Such catalysts require special handling. In contrast, the catalysts of the present invention are prepared in situ upon reaction of a stable palladium source (such as [Pd(allyl)Cl]$_2$) with a stable commercially available, pre-packaged ligand (such a 10% by weight tri-(t-butyl)phosphine in hexane. Moreover, by the creation of the catalyst, in situ, the invention provides convenient access to ligand/Palladium ratio's generally unavailable through commercial sources.

Step D: reacting, in solvent B a compound of Formula VIII with cyclolpropylamine; optionally in the presence of a phosphite or other catalyst.

For purposes of this specification solvent B is defined to include an alkanol solvent such $C_{1-4}$alkanol solvents methanol, ethanol, propanols and butanols, and trifluoroethanol, or mixtures thereof. Acetonitrile may also be used. For purposes of this specification, the catalyst is defined to include Butyl phosphite $(BuO)_3P$), pyridine-N-oxides, tri-alkyl orthoacetate, zinc chloride, magnesium chloride, magnesium triflate, scandium triflate, lanthanum triflate, ytterbium triflate, titanocene dichloride, or zirconocene dichloride. Note that for purposes of this specification, the term catalyst is intended to indicate a reagent that accelerates the reaction, even if present in greater than classical "catalytic" amounts.

The molar ratio of cyclopropylamine to compound of Formula VIII or Via is typically greater than 1:1, and if often 1.1:1 or greater. Reducing this ratio reduces the yield. The ratio of catalyst to compound of Formula VIII or VIIIa is generally 0.025:1 to 0.075:1, often about 0.05:1 or possibly 0.10:1 to 1:1 or more. In the case of magnesium chloride a typical ratio of catalyst to compound of Formula VIII or VIIIa is 0.9:1 to 1:1.5. The reaction can be carried out at 40 to about 60° C., more typically 55-60° C., and is allowed to proceed until the reaction is substantially complete. The presence of oxygen is minimized by purging the reaction vessel with nitrogen gas prior to addition of the reagents. For optimal results, it desirable to perform Step D at or below a Kf of 3000 ppm.

The product of Step D is cooled to 0 to about 30° C., typically about room temperature. Thereafter, the solvent is replaced with an anti-solvent (anti-solvent B), such as by evaporation of the solvent, follow by the addition of excess anti-solvent. For purposes of this specification, anti-solvent B is defined as a solvent in product of the reaction (in this case the compound of Formula IX) 3-6 volumes of anti-solvent per volume of solvent is added to the product of Step C to precipitate compound of Formula VIII or VIIIa. For purposes of this specification, the anti-solvent is defined as a non-reactive solvent in which compound of Formula VIII or VIIIa will precipitate.

In order to remove impurities, the slurry comprising the precipitated compound of Formula VIII or VIIIa is washed a solvent, such as water, acetonitrile, isopropyl acetate, ethyl acetate, tetrahydrofuran, ethanol, propanols, and butanols. Thereafter, the solvent is removed, such as by filtration and vacuum drying. The filtered compound of Formula VIII or VIIIa can then be mixed with a conversion solvent, such as dry ethanol, methanol, trifluoroethanol, N-methylpyrrolidinone, methyl t-butyl ether or mixtures thereof, optionally heated to and held at 40 to 50° C. until at least 95% of the compound of Formula VIII or VIIa is in the desired form. The conversion solvent is then removed, such as by filtration or centrifugation and the resulting product is vacuum dried. The amount of conversion solvent required, is that sufficient to suspend or dissolve the compound of Formula VIII or VIIIa.

The term "aryl" unless specifically stated otherwise includes multiple ring systems as well as single ring systems such as, for example, phenyl or naphthyl.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and salts thereof.

The utility of the invention is illustrated by examples of phosphodiesterase-4 inhibitors that may be prepared by use of the invention.

Dosage levels from about 0.001 mg/kg to about 140 mg/kg of body weight per day are useful in the treatment of conditions such as asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues which are responsive to PDE4 inhibition, or alternatively about 0.05 mg to about 7 g per patient per day. For example, inflammation may be effectively treated by the administration of from about 0.01 mg to 50 mg of the compound per kilogram of body weight per day, or alternatively about 0.5 mg to about 2.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 0.01 mg to about 1000 mg of the active ingredient, typically 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The examples that follow are intended as an illustration of certain preferred embodiments of the invention and no limitation of the invention is implied.

Compounds of the present invention can be prepared according to the following methods. The substituents are the same as in Formula I except where defined otherwise.

Preparation of Intermediate compound of Formula V.

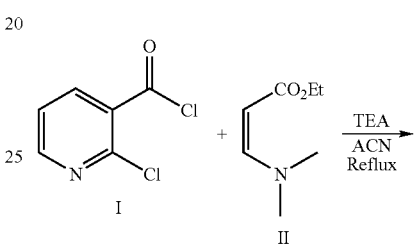

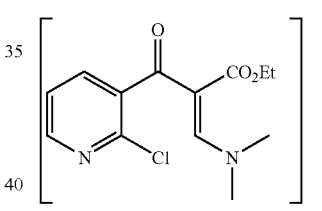

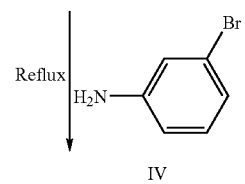

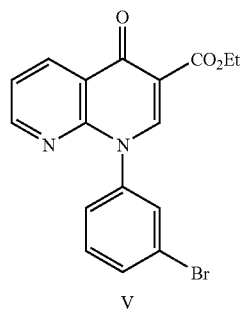

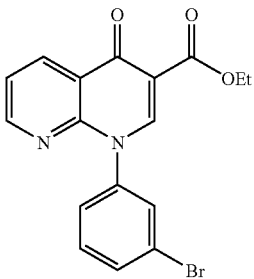

NAPHTHYRIDONE 1

Step 1: Ethyl 1-(3-bromophenyl)-1,4-dihydro[1,8]naphthyridin-4-one-3-carboxylate A mixture of ethyl 2-chloronicotinoyl acetate (purchased or prepared following a procedure described in J. Het. Chem. 30, 855, 1993) (1 eq), triethylamine (4 eq) and ethyl 3,3-dimethylaminoacrylate (1.5 eq) in acetonitrile (0.5M) was heated to reflux for 3 h, cooled to 40-50° C. and 3-bromoaniline (1 eq) was added. The reaction was heated to reflux overnight, cooled to rt, diluted with water (2 volume). The product was isolated by filtration and washed with water, ether or acetonitrile-water (1:1).

$^1$H NMR (Acetone-d$_6$) δ 1.32 (t, 3H), 4.29 (q, 2H), 7.54-7.63 (m, 2H), 7.69 (dd, 1H), 7.78 (dd, 1H), 7.93 (s, 1H), 8.66-8.71 (m, 3H).

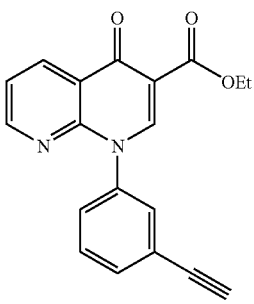

NAPHTHYRIDONE 2

Ethyl-1-(3-acetylenylphenyl)-1,4-dihydro[1,8]naphthyridin-4-one-3-carboxylate Following the procedure described for Naphthyridone 1, but substituting 3-acetylenylaniline for 3-bromoaniline results in the Title Naphthyridone 2.

$^1$H NMR (CDCl$_3$) δ 1.42 (t, 3H), 3.19 (s, 1H), 4.20 (q, 2H), 7.42-7.46 (m, 2H), 7.53-7.59 (m, 2H), 7.67 (dt, 1H), 8.64 (dd, 1 h), 8.68 (s, 1H), 8.83 (dd, 1H).

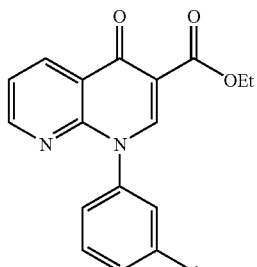

NAPHTHYRIDONE 3

Ethyl-1-(3-cyanophenyl)-1,4-dihydro[1,8]naphthyridin-one-3-carboxylate

Following the procedure described for Naphthyridone 1, but substituting 3-cyanoaniline for 3-bromoaniline results in the Title Naphthyridone 3.

$^1$H NMR (DMSO-d$_6$) δ 1.27 (t, 3H), 4.23 (q, 2H), 7.57 (dd, 1H), 7.80 (t, 1H), 7.96-8.04 (m, 2H), 8.20 (t, 1H), 8.61 (dd, 1H), 8.68 (dd, 1H), 8.70 (s, 1H).

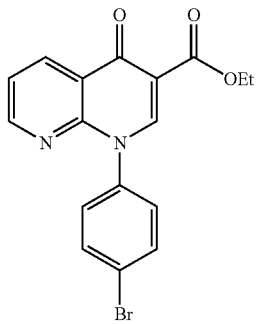

NAPHTHYRIDONE 4

Ethyl-1-(4-bromophenyl)-1,4-dihydro[1,8]naphthyridinone-3-carboxylate

Following the procedure described for Naphthyridone 1, but substituting 4-bromoaniline for 3-bromoaniline results in the Title Naphthyridone 4.

$^1$H NMR (DMSO-d$_6$) δ 1.26 (t, 3H), 4.22 (q, 2H), 7.54-7.59 (m, 3H), 7.78 (d, 2H), 8.61 (dd, 1H), 8.63 (s, 1H), 8.68 (dd, 1H).

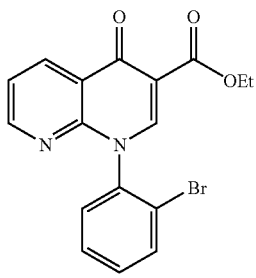

NAPHTHYRIDONE 5

Ethyl-1-(2-bromophenyl)-1,4-dihydro[1,8]naphthyridin-4-one-3-carboxylate

Following the procedure described for Naphthyridone 1, but substituting 2-bromoaniline for 3-bromoaniline results in the Title Naphthyridone 5.

$^1$H NMR (DMSO-d$_6$) δ 1.26 (t, 3H), 4.23 (q, 2H), 7.53-7.62 (m, 3H), 7.75 (dd, 1H), 7.88 (dd, 1H), 8.61 (s, 1H), 8.63 (dd, 1H), 8.68 (dd, 1H).

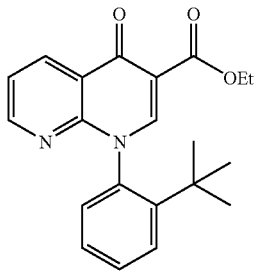

NAPHTHYRIDONE 6

Ethyl-1-(2-tert-butylphenyl)-1,4-dihydro[1,8]naphthyridin-4-one-3-carboxylate Following the procedure described for Naphthyridone 1, but substituting 1-bromo-2-tert-butylphenylaniline for 1-bromo-2-tert-butylaniline results in the Title Naphthyridone 6.

$^1$H NMR (DMSO-d$_6$) δ 1.08 (s, 9H), 1.25 (t, 3H), 4.22 (q, 2H), 7.30-7.40 (m, 2H), 7.50-7.56 (m, 2H), 7.73 (dd, 1H), 8.59 (s, 1H), 8.62 (dd, 1H), 8.70 (dd, 1H).

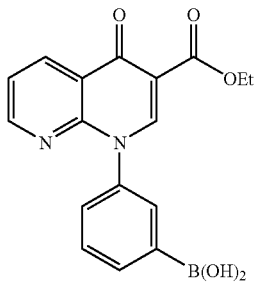

NAPHTHYRIDONE 7

Ethyl-1-(3-phenylboronic acid)-1,4-dihydro[1,8]naphthyridin-4-one-3-carboxylate Following the procedure described for Naphthyridone 1, but substituting 3-aminophenylboronic acid for 3-bromoaniline results in the Title Naphthyridone 7.

$^1$H NMR (DMSO-d$_6$) δ 1.26 (t, 3H), 4.22 (q, 2H), 7.56 (coincident triplets, 2H), 7.60 (d, 1H), 7.87 (s, 1H), 7.94 (d, 1H), 8.24 (s, 2H, exchangeable), 8.61 (d, 1H), 8.62 (s, 1H), 8.68 (d, 1H).

PDE-4 Inhibitor Compounds

The following are examples of PDE4 inhibitor compounds which can be made following the procedures as described herein. Note that the formula number used in the schemes 1 to 12 and the discussion of these schemes should not be confused with the formula numbers used elsewhere in this patent application. Examples 1 to 13 were prepared using Naphthyridone 1:

Scheme 1

In a first method outlined in Scheme 1 below, an appropriately substituted derivative of ethyl 2-chloronicotinoyl acetate of formula II is reacted with 1.5 equivalents of triethyl orthoformate and 5 equivalents of acetic anhydride at 130° C., and after removal of the volatile components, the crude 2-chloronicotinoyl acrylate of formula III is immediately reacted with 1.2 equivalents of an appropriately substituted haloaryl amine of formula IV, such as, for example 3-bromoaniline, in a halogenated hydrocarbon solvent such as methylene chloride at a temperature of 0° C. to room temperature. After an appropriate reaction time ranging from 2 to 24 hours the resulting 3-arylamino acrylate of formula V is obtained by evaporation of the solvent and may be further purified by chromatography on silica gel or crystallization from an appropriate solvent.

The compound of formula V may alternatively be used without further purification in the following step. Cyclization of the compound of formula V to the 1-haloaryl-1,4-dihydro[1,8]naphthyridin-4-one carboxylate of formula VI is effected by treatment with a small excess of a strong base such as an alkali metal hydride, for example sodium hydride, in an appropriate solvent such as tetrahydrofuran at a starting temperature of 0° C. with warming to room temperature if required to complete the process. The product of formula VI is isolated in crude form by dilution with a large volume of water followed by filtration or by extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

The product of formula VI thus obtained can be hydrolyzed to the corresponding carboxylic acid derivative under basic conditions, using an aqueous solution of an alkali base such as an alkali carbonate or preferably sodium or potassium hydroxide, with an organic cosolvent such as tetrahydrofuran or a primary, secondary or tertiary alkanol, such as methanol or ethanol, or a combination thereof at temperatures ranging from room temperature to reflux temperature for the appropriate time. The resultant carboxylic acid is isolated in crude form following acidification using an aqueous solution of an inorganic acid such as hydrochloric, sulfuric or a similar acid, and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

The carboxylic acid is then transformed into the appropriate primary, secondary or tertiary amide analog of formula VII by any general procedure well known to the organic chemist, preferably via initial transformation into a mixed anhydride by treatment with a small excess, such as 1.25 equivalents, of an appropriate alkyl chloroformate such as ethyl or isobutyl chloroformate, in the presence of a larger excess, such as 2.5 equivalents, of a tertiary organic amine such as triethylamine or N,N-diisopropylethylamine in an organic solvent such as tetrahydrofuran at low temperature, preferably 0° C., for a period of 30 minutes to 3 hours. An excess, usually 5 or more equivalents, of an appropriate primary or secondary amine or of an aqueous solution of ammonium hydroxide is then added and the resulting reaction is allowed to proceed at a temperature ranging from 0° C. to room temperature for an appropriate length of time, usually 1-24 hours.

The desired amide of formula VII is then isolated in crude form by precipitation with water and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration. In cases where the amide moiety is 2,6-dichloropyridin-4-yl, a different procedure is used in which the anion of 4-amino-3,5-dichloropyridine is generated at low temperature, preferably at 0° C., using a strong alkali hydride such as sodium hydride in a solvent such as tetrahydrofuran, and reacted with the acid chloride of a carboxylic acid (from hydrolysis of an ester of formula VI) generated by an appropriate known procedure, usually by the action of oxalyl chloride activated by a catalytic amount of N,N-dimethylformamide in a solvent such as tetrahydrofuran.

The amides of general formula VII are processed into the products of formula I by reaction with an appropriately substituted aryl or heteroaryl boronic acid or boronate ester of formula VIII under the catalysis of a transition metal species such as trans-dibromobis(triphenylphosphine)palladium (II) or [1,1'-bis(diphenylphosphino)ferrocene]dichloropalladium(II) in an appropriate solvent or solvent mixture, preferably a 1:1 mixture of toluene and ethanol in the presence of an excess of an aqueous solution of an alkali base such as sodium carbonate, at an appropriate temperature, preferably 50 to 100° C., for an appropriate length of time ranging from 0.5 to 48 hours.

The resulting reaction product is then isolated in crude form by precipitation with water and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

Compounds of formula I may also be obtained by reaction of a compound of formula VII with an appropriately substituted aryl or heteroaryl tributyl stannane of formula IX under the catalysis of a transition metal species such as trans-dibromobis (triphenylphosphine)palladium (II) or [1,1'-bis(diphenylphosphino)ferrocene]dichloropalladium (II) in the presence of a copper (I) species such as cuprous iodide an appropriate solvent such as N,N-dimethylformamide at a temperature range of 50-100° C. for a period of 2 to 24 hours. Isolation of the reaction product is effected as described above.

Alternatively, an ester of formula VI can be processed into an ester of formula X by reaction with an appropriately substituted boronic acid or boronate ester, or with an appropriately substituted stannane derivative under the conditions described above, and the ester can be hydrolyzed and transformed into an amide of formula I.

The boronic acids of formula VIII or corresponding boronate esters are usually obtained from commercial sources. Where required, they can be prepared readily from the corresponding halides via metallation with n-butyl-lithium followed by reaction with a trialkyl borate, or by using classical transition metal-catalyzed coupling procedures using diboron pinacol ester. The stannanes of formula IX are generated from the corresponding halides via initial metallation using n-butyllithium followed by addition of tributyltin chloride.

Scheme 1

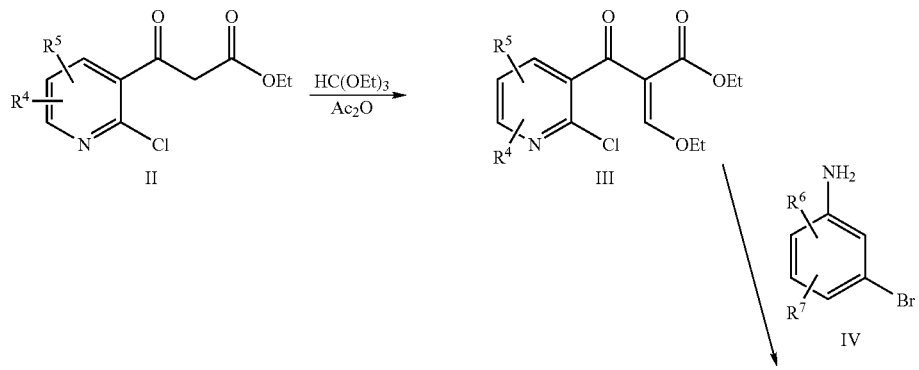

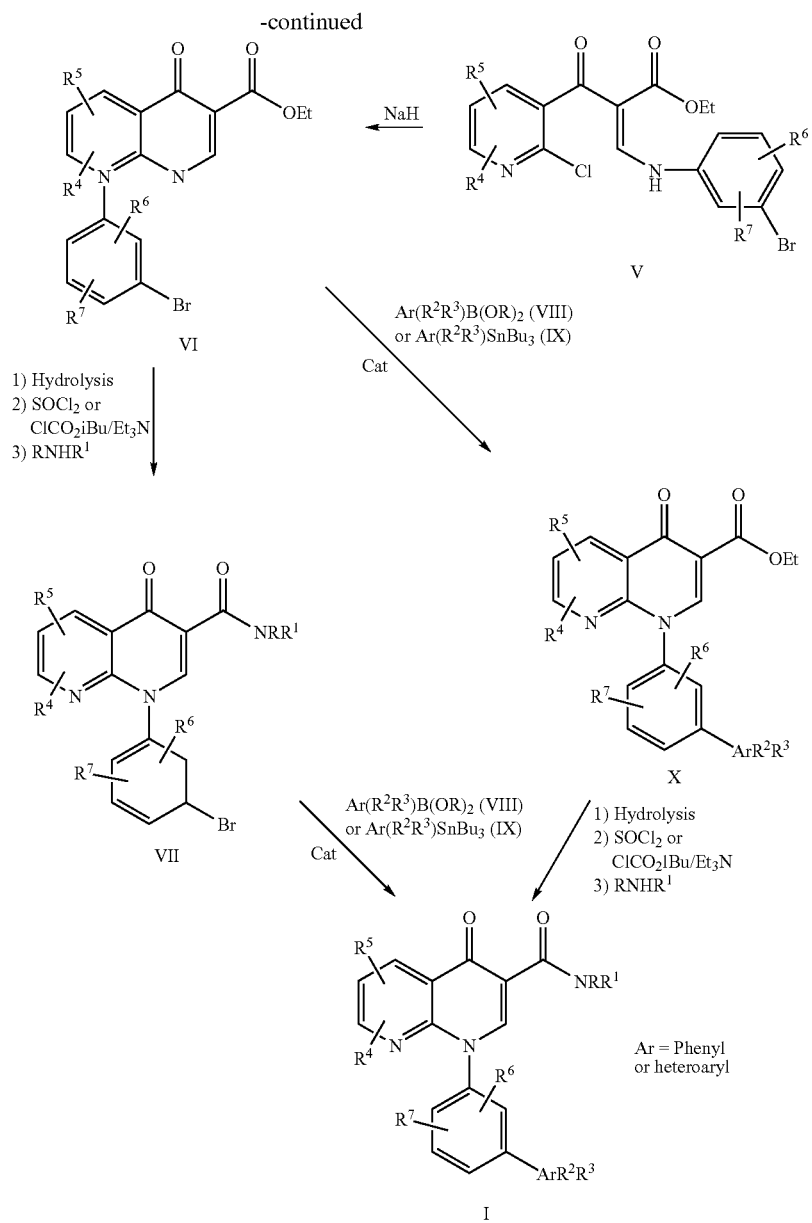

In an alternative method for the preparation of compounds of formula I, outlined in Scheme 2 below, an amide of formula VII can be transformed into a corresponding boronate ester of formula XI by treatment with an excess of diboron pinacol ester in the presence of an inorganic salt such as potassium acetate under the catalysis of a transition metal species such as trans-dibromobis(triphenylphosphine) palladium (II) or [1,1'-bis(diphenylphosphino)ferrocene] dichloropalladium(II) in a solvent such as N,N-dimethylformamide at temperatures ranging from 50 to 100° C. for a length of time ranging from 1 to 48 hours. The boronate of formula XI may be isolated by precipitation with water and filtration or extraction into an appropriate organic solvent such as diethyl ether, ethyl acetate, or a halogenated hydrocarbon solvent such as chloroform or methylene chloride. The resulting product can be further purified by chromatography on silica gel, crystallization or prolonged stirring in an appropriate solvent followed by filtration.

Alternatively, the boronate of formula XI can be used as generated in situ in the reaction medium without isolation, and reacted with a small excess of an appropriately substituted aryl or heteroaryl halide of formula XII under the catalysis of a transition metal species such as [1,1'-bis (diphenylphosphino)ferrocene]dichloropalladium(II) in an appropriate solvent or solvent mixture, preferably a 1:1 mixture of toluene and ethanol in the presence of an excess of an aqueous solution of an alkali base such as sodium carbonate, at an appropriate temperature, preferably 50 to 100° C. for an appropriate length of time ranging from 0.5 to 48 hours.

The reaction product of formula I is then isolated in crude form by precipitation with water and filtration or extraction into an appropriate organic solvent such as diethyl ether, ethyl acetate, or a halogenated hydrocarbon solvent such as chloroform or methylene chloride. The product can be further purified by chromatography on silica gel, crystallization or prolonged stirring in an appropriate solvent followed by filtration.

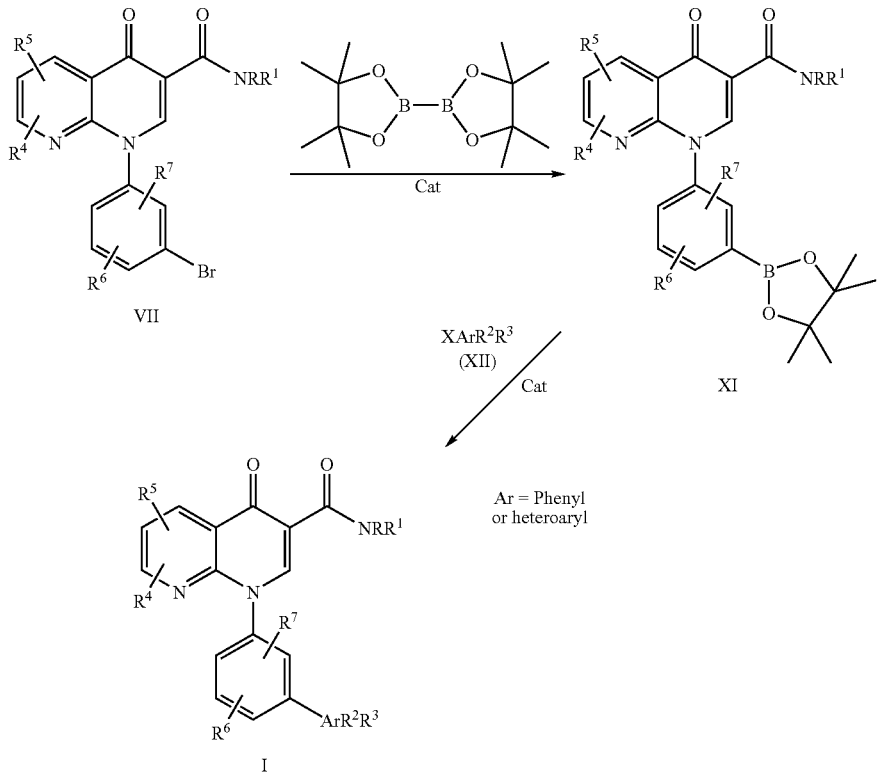

In a third method used for the synthesis of compounds of formula I of this invention (scheme 3), an intermediate nicotinoyl acrylate of formula III is reacted with an appropriately constructed diaryl or heteroarylaryl amine of formula XIII under the conditions described previously to afford a compound of formula XIV which is cyclized by the action of a strong base such as sodium hydride as described above to afford an ester of formula X which is processed into a compound of formula I via hydrolysis and amide formation as described above.

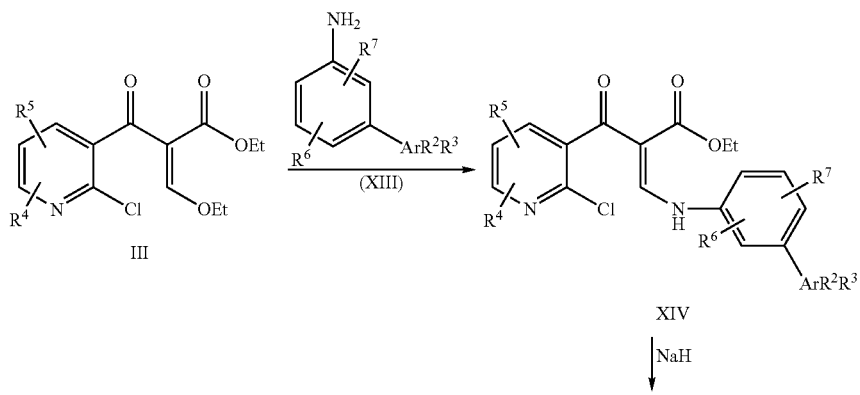

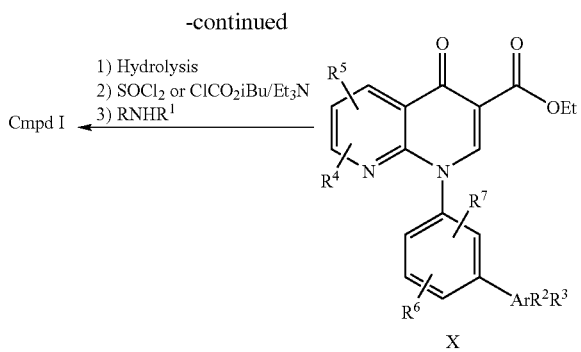

The diaryl or heteroarylarylamine intermediates of formula XIII were assembled as indicated in Scheme 4. An appropriately substituted aniline boronic acid of formula XV is coupled with an appropriately substituted aryl or heteroaryl halide of general formula XII under the catalysis of a transition metal species as described above to afford the formula XIII compounds used in Scheme 3.

Scheme 4

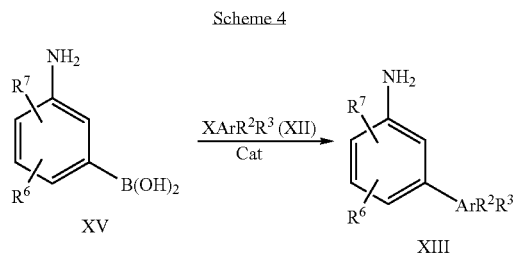

Bromopyridine intermediates substituted at the 2-position by carbon based nucleophiles of formula XVII, where $R^8$ is selected from $R^2$ moieties having a carbon-carbon link to the pyridine, are conveniently prepared as shown in Scheme 5. The bromopyridine intermediates are prepared from dihalides of formula XVI by treatment with an appropriate solution of a Grignard reagent under the catalysis of a transition metal species such as [1,1'-bis(diphenylphosphino)ferrocene]dichloronickel (II) in a solvent such as tetrahydrofuran at a temperature range of $-10°$ C. to room temperature and the resulting reaction mixture worked up by well known procedures to afford the desired product.

Scheme 5

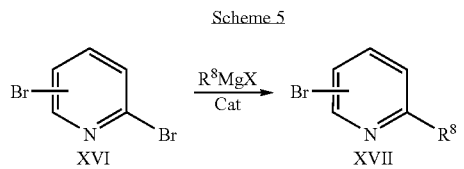

Halopyridine intermediates of type XVIII where the 2-substituent is an alkoxy group $OR^9$ are derived from dihalides of formula XVI by displacement with an appropriate alkali alkoxide as outlined in scheme 6. The reaction is effected in a solvent such as N,N-dimethylformamide at a temperature range of 0° C. to room temperature and, upon completion of the reaction, the products are isolated and purified following classical procedures.

Scheme 6

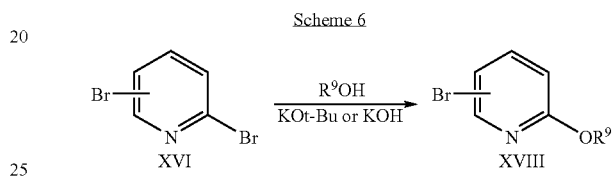

Where intermediates of formula XIX or XX in which the 2-substituent is sulfide, sulfoxide or sulfone were required, they were attained as described in Scheme 7. An appropriate dihalopyridine of type XVI is reacted with an appropriate thioalkoxide, usually generated from the corresponding thiol or disulfide through the action of a strong base such as an alkali hydride or n-butyllithium, in a solvent such as N,N-dimethylformamide or diethyl ether at a temperature range of $-78°$ C. to room temperature. Upon completion of the reaction the products of formula XIX are isolated and purified following classical procedures. The products thus obtained can be oxidized to the corresponding sulfoxides or sulfones of formula XX through the action of an oxidizing agent such as oxone or an organic peracid. In Scheme 7, $R^{10}$ is H or $C_{1-6}$alkyl.

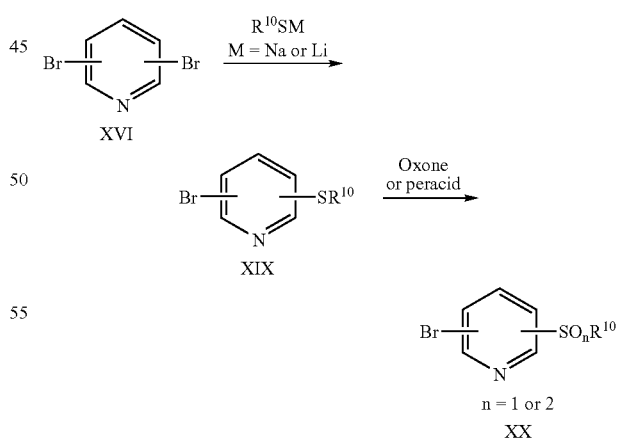

The preparation of haloacyl pyridine intermediates of formula XXII, presented in Scheme 8, requires treatment of a halopyridine ester of type XXI with a solution of an appropriate Grignard reagent in a solvent such as diethyl ether at a temperature range of 0° C. to room temperature. If the reaction is carried out for a longer period or under reflux a halopyridine carbinol of formula XXII is obtained. In Schemes 8 and 9, $R^7$ is $C_{1-6}$alkyl and $R^6$ is methyl or ethyl.

tributyl stannane of formula IX using one of the methods described above to afford the desired compound.

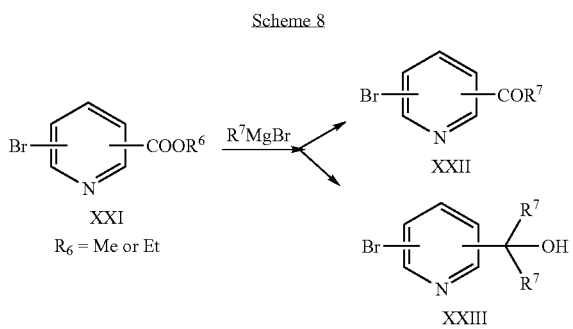

Scheme 8

XXI
$R_6$ = Me or Et

XXII

XXIII

Scheme 9 outlines an alternative sequence for the synthesis of certain halopyridine carbinols of type XXIII. When 2,5-dibromopyrine is treated with n-butyllithium in toluene at −78° C. followed by addition of an appropriate ketone or aldehyde and subsequent quenching at −78° C., a carbinol of type XXII results where the carbinol group occupies the 2-position of the pyridine ring. If the metallation step is performed in diethyl ether, the same process leads to an intermediate of formula XXIII in which the carbinol group occupies the 5-position of the pyridine ring.

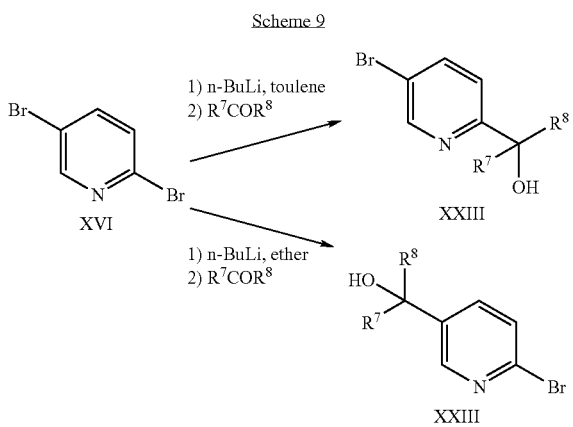

Scheme 9

XVI

XXIII

XXIII $R^7$ and $R^8$ can be the same or different either $R^7$ or $R^8$ can be hydrogen Scheme 10 demonstrates the methods of synthesis for compounds of formula I in which $R^2$ is a substituted phenyl or heteroaryl group. An intermediate compound of Type I where $R^2$ is a halogen is reacted with an appropriately substituted boronic acid or boronate ester of formula VII or

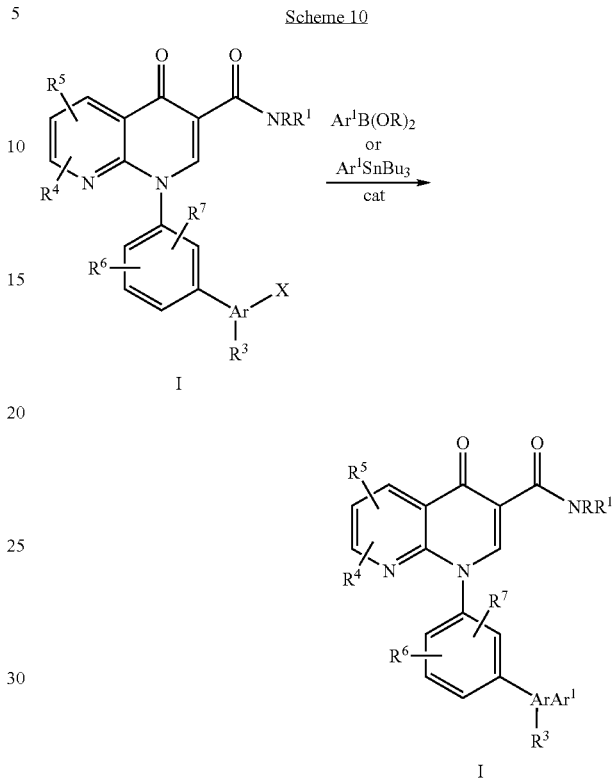

Scheme 10

I

I

Various further transformations on pre-assembled compounds of formula I are illustrated in Scheme 11. In cases where the Ar group is a pyridine or quinoline group it can be oxidized to the corresponding nitrogen oxide by the action of an appropriate oxidizing agent such as m-chloroperoxybenzoic acid or magnesium monoperoxyphthalate under commonly used conditions. In cases where one or more of the substituents on the Ar group is a ketone it is conveniently transformed into an oxime analog through the action of hydroxylamine in pyridine as solvent. A sulfide substituent is easily oxidized to the corresponding sulfoxide or sulfone derivative by using an appropriate quantity of an oxidant such as oxone or an organic peracid.

The transformation of a 2-benzyloxypyridine into the corresponding 2-pyridone was accomplished by treatment with trifluoroacetic acid in a solvent such as methylene chloride at room temperature or under slight warming. The removal of a tert-butyloxycarbonyl protecting group from a piperazine ring is effected by reaction with trifluoroacetic acid in a solvent such as 1,2-dichloroethane at reflux temperature. In examples where a substituent on Ar is a hydroxymethyl group it can be derivatized to the analogous halomethyl moiety using a tetrahalomethane in the presence of a trisubstituted phosphine such as triphenylphosphine or diphos in a solvent such as methylene chloride. The halide can be displaced by an appropriate sulfinic acid sodium salt to afford the alkyl or arylsulfonylmethyl analog.

Scheme 11

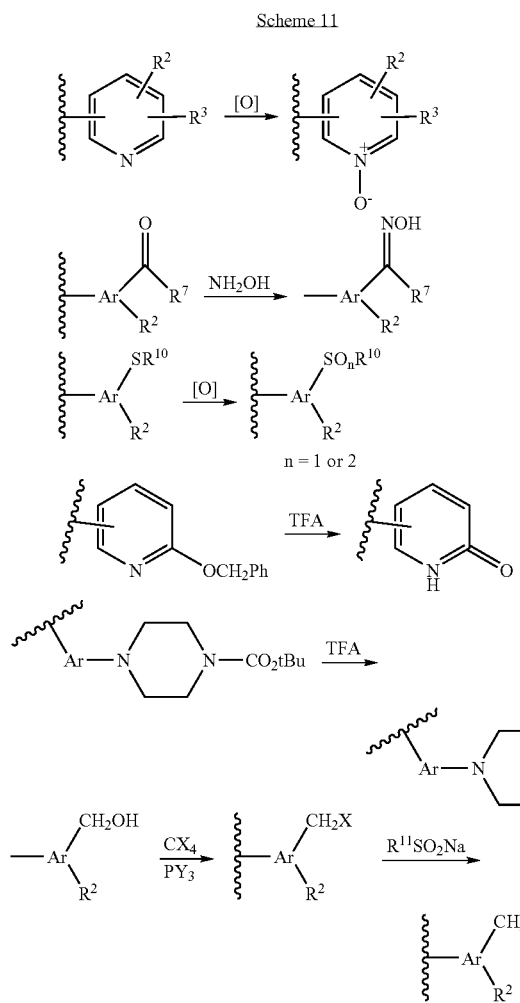

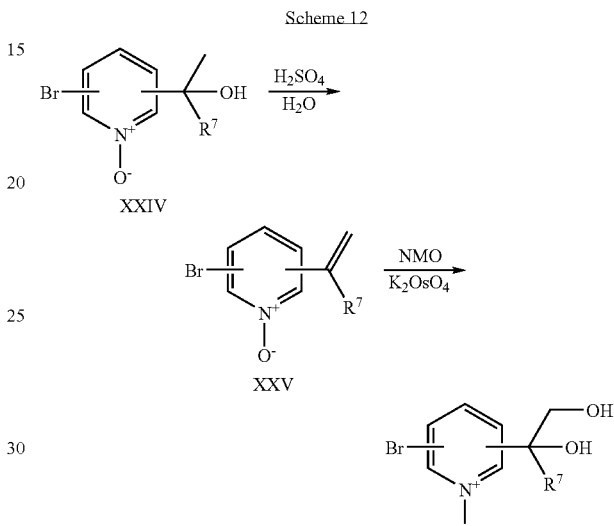

The transformation of a 1-hydroxy-1-methylalkyl derivative such as exemplified by compounds of type XXIV of scheme 12 into 1,2-dihydroxyalkyl analogs of type XXVI is effected via initial acid-catalyzed dehydration, for example by heating in aqueous sulfuric acid, to afford an intermediate 1-alkylvinyl species of type XXV which is transformed into the desired diol XXVI by a dihydroxylation process, using for example an oxidant such as 4 methylmorpholine N-oxide (NMO) in the presence of a catalytic quantity of potassium osmate dihydrate.

EXAMPLES

EXAMPLES of the present invention are summarized in the following table to Formula (I):

TABLE 1

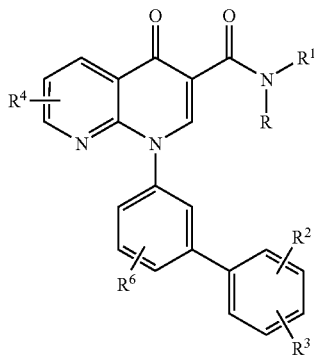

| EX. | R | $R^1$ | $R^2$ | $R^3$ | $R^4$ | $R^6$ |
|---|---|---|---|---|---|---|
| 1 | H | i-pr | 3-C(O)Me | | H | H | H |

TABLE 1-continued

Structure I: A 1,8-naphthyridin-4-one-3-carboxamide core with substituents R, R¹ on the amide nitrogen, R⁴ on the naphthyridine, and a biphenyl group at N1 bearing R², R³, R⁶.

| EX. | R | R¹ | R² | R³ | R⁴ | R⁶ |
|---|---|---|---|---|---|---|
| 2 | H | 3,5-dichloropyridin-4-yl | 3-C(O)Me | H | H | H |
| 3 | H | i-pr | 4-n-propyl | H | H | H |
| 4 | H | i-pr | 4-C(O)Me | H | H | H |
| 5 | H | i-pr | 2-Me | H | H | H |
| 6 | Me | i-pr | 4-C(O)Me | H | H | H |
| 9 | H | t-bu | 4-C(O)Me | H | H | H |
| 11 | H | i-pr | 4-(4-tert-butoxycarbonylpiperazin-1-yl) | H | H | H |
| 16 | H | c-pr | 4-CH₂OH | H | H | H |
| 18 | H | c-pr | 4-SEt | H | H | H |
| 20 | H | c-pr | 4-SO₂NH₂ | H | H | H |
| 21 | H | i-pr | 3-OEt | H | H | H |
| 22 | H | i-pr | 4-SMe | H | H | H |
| 23 | H | i-pr | 3-C(O)Me | 4-OH | H | H |
| 49 | H | i-pr | 4-SO₂Me | H | H | H |
| 52 | H | c-pr | 4-SO₂Et | H | H | H |
| 53 | H | c-pr | 4-S(O)Et | H | H | H |
| 54 | H | i-pr | 4-C(=NOH)Me | H | H | H |
| 55 | H | i-pr | 4-(piperazin-1-yl) | H | H | H |
| 56 | H | c-pr | 4-CH₂SO₂Me | H | H | H |

TABLE 2

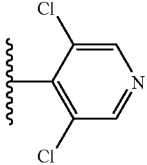

| EX. | R | R¹ | π Position | R² | R³ | R⁴ | R⁶ | n |
|---|---|---|---|---|---|---|---|---|
| 7 | H | i-pr | 3 | H | H | H | H | 0 |
| 10 | H | 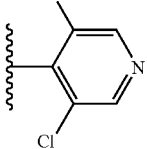 | 3 | H | H | H | H | 0 |
| 14 | H | c-pr | 3 | H | H | H | H | 0 |
| 15 | H | i-pr | 3 | 5-SMe | H | H | H | 0 |
| 17 | H | c-pr | 4 | H | H | H | H | 0 |
| 24 | H | i-pr | 3 | 5-COOEt | H | H | H | 0 |
| 25 | H | i-pr | 3 | 5-CMe₂OH | H | H | H | 0 |
| 26 | H | i-pr | 3 | 6-CH₂CHMe₂ | H | H | H | 0 |
| 27 | H | i-pr | 3 | 5-C(O)Me | H | H | H | 0 |
| 28 | H | i-pr | 3 | 6-Me | H | H | H | 0 |
| 30 | H | H | 3 | 6-CMe₂OH | H | H | H | 1 |
| 32 | H | c-pr | 3 | 5-SO₂Me | H | H | H | 0 |
| 33 | H | c-pr | 2 | 4-CMe₂OH | H | H | H | 1 |
| 34 | H | c-pr | 2 | 5-CMe₂OH | H | H | H | 0 |
| 35 | H | c-pr | 4 | 3-CMe₂OH | H | H | H | 0 |
| 36 | H | c-pr | 4 | 3-CMe₂OH | H | H | H | 1 |
| 37 | H | c-pr | 3 | 6-SO₂I-pr | H | H | H | 0 |
| 38 | H | c-pr | 3 | 6-OMe | H | H | H | 0 |
| 39 | H | c-pr | 3 | 6-Me | H | H | H | 0 |
| 40 | H | c-pr | 3 | 6-OCH₂CF₃ | H | H | H | 0 |
| 41 | H | c-pr | 3 | 5-Br | H | H | H | 0 |
| 42 | H | c-pr | 3 | 6-OCH₂Ph | H | H | H | 0 |
| 43 | H | c-pr | 3 | 6-C(c-pr)₂OH | H | H | H | 0 |
| 44 | H | c-pr | 2 | 5-CMe₂OH | H | H | H | 1 |
| 45 | H | c-pr | 3 | 6-CMe₂OH | H | H | H | 0 |
| 46 | H | i-butyl | 3 | 6-CMe₂OH | H | H | H | 0 |
| 47 | H | c-pr | 3 | 6-CMe₂OH | H | H | 5-Br | 0 |
| 48 | H | c-pr | 2 | 6-CMe₂OH | H | H | H | 0 |
| 50 | H | c-pr | 3 | 6-SO₂Me | H | H | H | 0 |
| 51 | H | i-pr | 3 | 5-SO₂Me | H | H | H | 0 |
| 59 | H | i-pr | 3 | H | H | H | H | 1 |
| 60 | H | 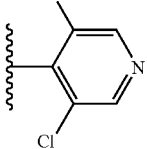 | 3 | H | H | H | H | 1 |

TABLE 2-continued

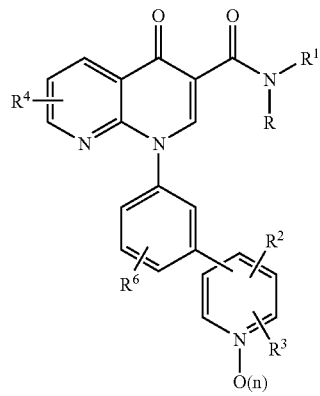

| EX. | R | R¹ | π Position | R² | R³ | R⁴ | R⁶ | n |
|---|---|---|---|---|---|---|---|---|
| 61 | H | i-pr | 3 | 5-COOEt | H | H | H | 1 |
| 62 | H | i-pr | 3 | 5-CMe₂OH | H | H | H | 1 |
| 63 | H | i-pr | 3 | 6-CH₂CHMe₂ | H | H | H | 1 |
| 64 | H | i-pr | 3 | 6-Me | H | H | H | 1 |
| 65 | H | c-pr | 3 | H | H | H | H | 1 |
| 66 | H | c-pr | 3 | 6-CMe₂OH | H | H | H | 1 |
| 67 | H | c-pr | 4 | H | H | H | H | 1 |
| 68 | H | c-pr | 3 | 5-Br | H | H | H | 1 |
| 73 | H | i-butyl | 3 | 6-CMe₂OH | H | H | H | 1 |
| 74 | H | c-pr | 3 | 6-Me | H | H | H | 1 |
| 75 | H | c-pr | 3 | 6-SO₂Me | H | H | H | 1 |
| 76 | H | c-pr | 3 | 6-CMe₂OH | H | H | 5-Br | 1 |
| 77 | H | c-pr | 3 | 6-CMe(CH2OH)OH | H | H | H | 1 |

TABLE 3

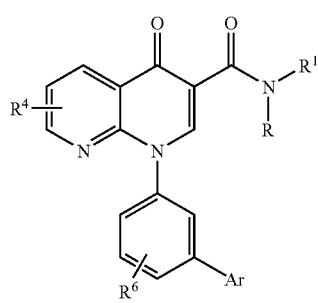

| Example | R | R¹ | Ar | R⁴ | R⁶ |
|---|---|---|---|---|---|
| 8 | H | i-pr | indol-5-yl | H | H |
| 12 | H | i-pr | guinolin-3-yl | H | H |
| 13 | H | i-pr | pyrimidin-5-yl | H | H |
| 19 | H | c-pr | 3-thienyl | H | H |
| 29 | H | c-pr | 1-oxidopyrimidin-5-yl | H | H |

TABLE 3-continued

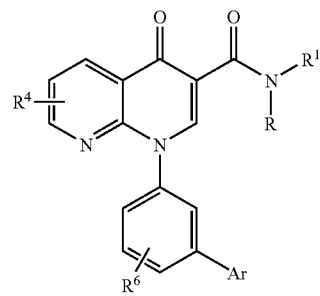

| Example | R | R¹ | Ar | R⁴ | R⁶ |
|---|---|---|---|---|---|
| 57 | H | c-pr | 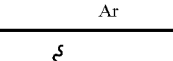 | H | H |
| 72 | H | i-pr | 1-oxidoquinolin-3-yl | H | H |

TABLE 4
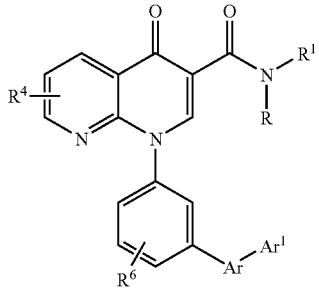
| Example | R | R¹ | Ar | Ar¹ | R⁴ | R⁶ |
|---|---|---|---|---|---|---|
| 31 | H | i-pr | Ph | 4-(pyridin-3-yl) | H | H |
| 58 | H | c-pr | Pyridin-3-yl | 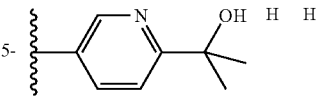 | H | H |
| 69 | H | c-pr | Pyridin-3-yl | 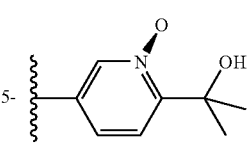 | H | H |
| 70 | H | c-pr | 1-oxidopyridin-3-yl | 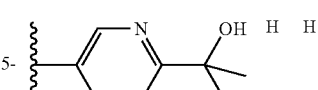 | H | H |
| 71 | H | c-pr | 1-oxidopyridin-3-yl | 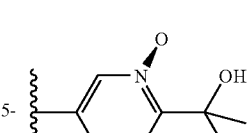 | H | H |
TABLE 5
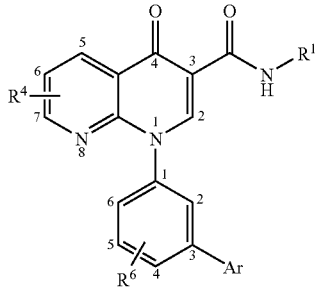
| R¹ | R⁴ | R⁶ | Ar |
|---|---|---|---|
| c-pr | H | H | 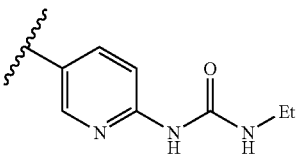 |

TABLE 5-continued
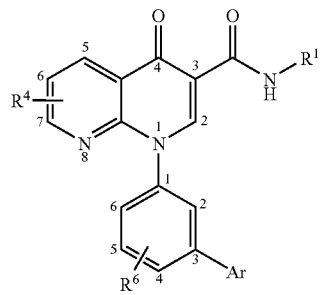
| R¹ | R⁴ | R⁶ | Ar |
|---|---|---|---|
| c-pr | H | H | 3-methyl-5-(5-methyl-1-oxidopyridin-3-yl)-1,2,4-oxadiazole |
| i-pr | 7-Me | H | 4-acetylphenyl |
| i-pr | H | 5-Me | 4-acetylphenyl |
| c-pr | H | H | 2-(1,1,1,3,3,3-hexafluoro-2-hydroxypropan-2-yl)thiazol-5-yl |
| c-pr | H | H | 5-phenylpyridin-3-yl |
| c-pr | H | H | 5-(thiophen-3-yl)pyridin-3-yl |

TABLE 5-continued
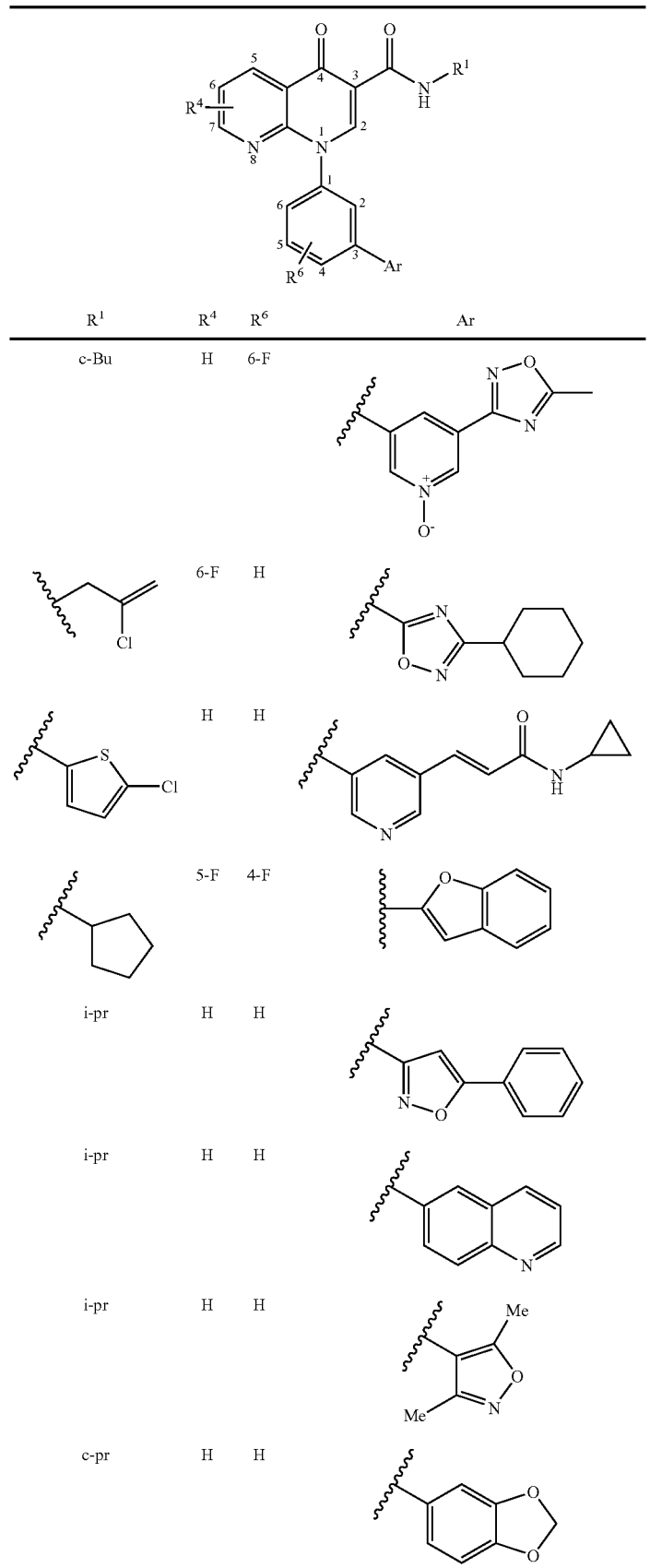
| R¹ | R⁴ | R⁶ | Ar |
|---|---|---|---|
| c-Bu | H | 6-F | 5-(5-methyl-1,2,4-oxadiazol-3-yl)pyridin-3-yl N-oxide |
| 2-chloroallyl | 6-F | H | 3-cyclohexyl-1,2,4-oxadiazol-5-yl |
| 5-chlorothien-2-yl | H | H | 5-[(E)-N-cyclopropylacrylamide]pyridin-3-yl |
| cyclopentylmethyl | 5-F | 4-F | benzofuran-2-yl |
| i-pr | H | H | 5-phenylisoxazol-3-yl |
| i-pr | H | H | quinolin-6-yl |
| i-pr | H | H | 3,5-dimethylisoxazol-4-yl |
| c-pr | H | H | benzo[d][1,3]dioxol-5-yl |

TABLE 5-continued
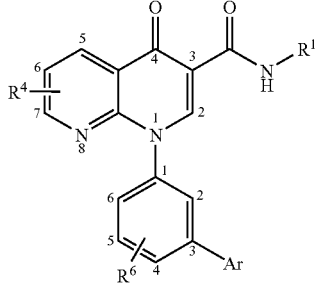
| R¹ | R⁴ | R⁶ | Ar |
|---|---|---|---|
| 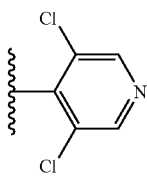 | H | H | 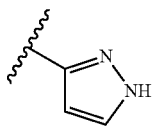 |
| c-pr | H | H | 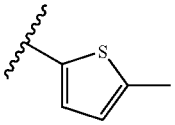 |
| c-Bu | H | H | 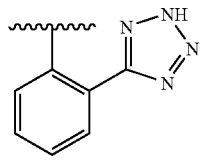 |
| 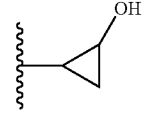 | H | H | 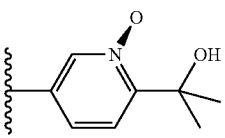 |
| 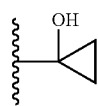 | H | H | 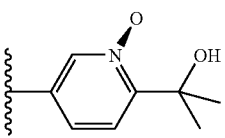 |

Example 1

N-Isopropyl-1-[3-(3-acetylphenyl)phenyl]-1,4-dihydro[1,8]naphthyridin-4-one-3-carboxamide

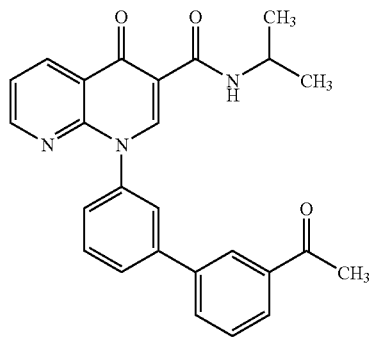

Step 1: Ethyl 3-(3-bromoanilino)-2-(2-chloronicotinoyl)acrylate

A mixture of ethyl 2-chloronicotinoyl acetate (41.1 g, 180.5 mmol), triethyl orthoformate (40.12 g, 271 mmol) and acetic anhydride (92.05 g, 902.5 mmol) was heated at 130° C. for 2.5 hours. The volatile components were distilled off and the residue was co-evaporated twice with xylene. The oily residue was dissolved in methylene chloride (250 mL) and 3-bromoaniline (37.25 g, 216.6 mmol) was added slowly. The resulting solution was stirred at room temperature for 18 hours, and the solvent evaporated away. The resulting crude compound was used as such in the next step.

Step 2: Ethyl 1-(3-bromophenyl)-1,4-dihydro[1,8]naphthyridin-4-one-3-carboxylate The crude compound from Step 1 was dissolved in tetrahydrofuran (500 mL), the solution was cooled to 0° C., and sodium hydride (as a 60% dispersion in oil, 9.4 g, 235 mmol) was added in portions. After stirring at 0° for 1 hour, the mixture was allowed to warm up to room temperature. After 2 hours, water (400 mL) was added to the suspension and and the insoluble solid was filtered and washed copiously with water. When dry, the solid was stirred in ether (150 mL) at room temperature for 24 hours and filtered to afford the title compound as a cream-colored solid.

$^1$H NMR (Acetone-d$_6$) δ 1.32 (t, 3H), 4.29 (q, 2H), 7.54-7.63 (m, 2H), 7.69 (dd, 1H), 7.78 (dd, 1H), 7.93 (s, 1H), 8.66-8.71 (m, 3H).

Step 3: 1-(3-Bromophenyl)-1,4-dihydro[1,8]naphthyridin-4-one-3-carboxylic acid A suspension of ethyl 1-(3-bromophenyl)-1,4-dihydro[1,8]naphthyridin-4-one-3-carboxylate from Step 2 (52.5 g, 140.7 mmol) in a mixture of tetrahydrofuran (400 mL), methanol (400 mL) and 1N aqueous sodium hydroxide (280 mL) was heated at ca 50° C. with stirring for 20 minutes. After cooling, the mixture was diluted with water (300 mL) and 1N aqueous HCl (325 mL) was added. After stirring for 45 minutes, the precipitate was filtered, washed well with water and dried to afford the title acid as a cream-colored solid.

$^1$H NMR (Acetone-d$_6$) δ 7.65 (t, 1H), 7.76 (m, 2H), 7.84 (d, 1H), 7.99 (s, 1H), 8.87 (m, 2H), 9.01 (s, 1H).

Step 4: N-Isopropyl-1-(3-bromophenyl)-1,4-dihydro[1,8]naphthyridin-4-one-3-carboxamide To a suspension of 1-(3-bromophenyl)-1,4-dihydro[1,8]naphthyridinone-3-carboxylic acid from Step 3 (26.3 g, 76 mmol) and triethylamine (23.2 g, 230 mmol) in tetrahydrofuran (1000 mL) at 0° C. was added isobutyl chloroformate (18.85 g, 138 mmol). After stirring at 0° C. for 2 hours, isopropylamine (23 g, 390 mmol) was added and the mixture was allowed to warm up to room temperature and stirred overnight. The mixture was then partitioned between ethyl acetate and water, the organic phase was dried and evaporated to a solid which was stirred in ether at room temperature for 3 hours and filtered to afford the N-Isopropyl-1-(3-bromophenyl)-1,4-dihydro[1,8]naphthyridin-4-one-3-carboxamide as a white solid.

$^1$H NMR (Acetone-d 6) δ 1.25 (d, 6H), 4.17 (m, 1H), 7.59-7.63 (m, 2H), 7.70 (d, 1H), 7.80 (d, 1H), 7.94 (s, 1H), 8.73 (m, 1H), 8.78 (d, 1H), 8.85 (s, 1H), 9.61 (br, NH).

Step 5: N-Isopropyl-1-[3-(3-acetylphenyl)phenyl]-1,4-dihydro[1,8]naphthyridinone-3-carboxamide A mixture of N-Isopropyl-1-(3-bromophenyl)-1,4-dihydro[1,8]naphthyridin-4-one-3-carboxamide from Step 4, 3-acetylphenylboronic acid (1.2 eq.), trans-dibromobis(triphenylphosphine)palladium (II) (0.05 eq.), toluene (6 mL/mmol), ethanol (2 mL/mmol) and 2M aqueous sodium carbonate (8 eq.) was refluxed for 1 hour under a nitrogen atmosphere. The mixture was diluted with ethyl acetate and the organic phase was washed with water and brine, dried and evaporated. The crude product was chromatographed on silica gel eluting with a gradient of 20-40% ether in methylene chloride to afford the N-Isopropyl-1-[3-(3-acetylphenyl)phenyl]-1,4-dihydro[1,8]naphthyridin-4-one-3-carboxamide product as a solid.

$^1$H NMR (CDCl$_3$) δ 1.29 (d, 6H), 2.65 (s, 3H), 4.28 (m, 1H), 7.47 (m, 2H), 7.55 (t, 1H), 7.65 (m, 2H), 7.80 (m, 2H), 7.95 (dd, 1H), 8.19 (brs, 1H), 8.70 (dd, 1H), 8.81 (dd, 1H), 9.05 (s, 1H), 9.65 (br, NH).

Example 2

N-(2,6-Dichloropyridin-4-yl)-1-[3-(3-acetylphenyl)phenyl]-1,4-dihydro[1,8]naphthyridin-4-one-3-carboxamide

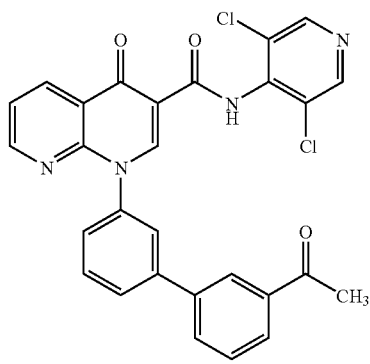

Step 1: Anion of 4-amino-3,5-dichloropyridine

A suspension of sodium hydride as 60% dispersion in oil (360 mg, 9 mmol) in tetrahydrofuran (15 mL) was cooled to 0° C. A solution of 4-amino-3,5-dichloropyridine (978 mg, 6 mmol) in tetrahydrofuran (15 mL) was added slowly. The resulting mixture was kept at 0° for 2.5 hours.

Step 2: Acid chloride of 1-(3-bromophenyl)-1,4-dihydro[1,8]naphthyridin-4-one-3-carboxylic acid A suspension of 1-(3-bromophenyl)-1,4-dihydro[1,8]naphthyridin-4-one-3-carboxylic acid from Step 3 of Example 1 (690 mg, 2 mmol) in tetrahydrofuran (12 mL) was cooled to 0° C., and oxalyl chloride (381 mg, 3 mmol) was added, followed by 2 drops of N,N-dimethylformamide. The resulting mixture was then stirred at room temperature for 1 hour then refluxed for 45 minutes and cooled to room temperature.

Step 3: N-(2,6-Dichloropyridin-4-yl)-1-(3-bromophenyl)-1,4-dihydro[1,8]naphthyridin-4-one-3-carboxamide The mixture from Step 2 above, as a brown suspension, was added via syringe to the cold suspension of Step 1. The resulting mixture was stirred at room temperature for 18 hours, quenched with aqueous saturated ammonium chloride solution and partitioned between ethyl acetate and water. The crude product from evaporation of the organic phase was triturated with ether (50 mL) and filtered, affording the N-(2,6-Dichloropyridin-4-yl)-1-(3-bromophenyl)-1,4-dihydro[1,8]naphthyridinone-3-carboxamide as a beige solid.

$^1$H NMR (Acetone-$d_6$) δ 7.61-7.70 (m, 2H), 7.76 (d, 1H), 7.81 (d, 1H), 8.00 (s, 1H), 8.62 (s, 2H), 8.80 (br s, 1H), 8.86 (d, 1H), 8.99 (s, 1H), 12.1 (br, NH).

Step 4: N-(2,6-Dichloropyridin-4-yl)-1-[3-(3-acetylphenyl)phenyl]-1,4-dihydro [1,8]naphthyridin-4-one-3-carboxamide Following the procedure of Step 5 of Example 1, but substituting N-(2,6-dichloropyridin-4-yl)-1-(3-bromophenyl)-1,4-dihydro[1,8]naphthyridin-4-one-3-carboxamide from step 3 for N-isopropyl 1-(3-bromophenyl)-1,4-dihydro [1,8]naphthyridin-4-one-3-carboxamide, the N-(2,6-Dichloropyridin-4-yl)-1-[3-(3-acetylphenyl)phenyl]-1,4-dihydro [1,8]naphthyridin-4-one-3-carboxamide compound was obtained as a solid.

$^1$H NMR (CDCl$_3$) δ 2.65 (s, 3H), 7.47 (d, 1H), 7.50-7.60 (m, 2H), 7.70 (m, 2H), 7.82 (d, 2H), 7.98 (d, 1H), 8.20 (s, 1H), 8.55 (s, 2H) 8.75 (brs, 1H), 8.92 (dd, 1H), 9.14 (s, 1H), 12.08 (br, NH).

Example 3

N-Isopropyl-1-[3-(4-n-propylphenyl)phenyl]-1,4-dihydro[1,8]naphthyridin-4-one-3-carboxamide

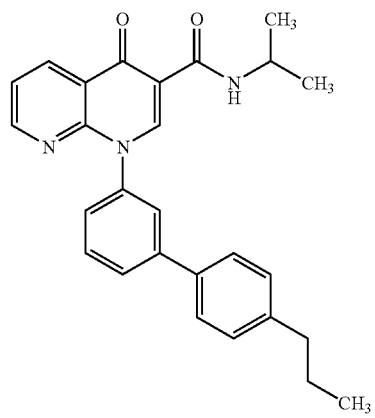

Following the procedure of Step 5 of Example 1, but substituting 4n-propylphenylboronic acid for 3-acetylphenylboronic acid the title compound was obtained as a white solid.

$^1$H NMR (Acetone-$d_6$) δ 0.93 (t, 3H), 1.24 (d, 6H), 1.65 (m, 2H), 2.62 (t, 2H), 4.18 (m, 1H), 7.31 (d, 2H), 7.58-7.61 (m, 2), 7.68-7.72 (m, 3H), 7.87 (d, 1H), 7.95 (s, 1), 8.72 (m, 1H), 8.78 (dd, 1H), 8.92 (s, 1H), 9.66 (br, NH).

Example 4

N-Isopropyl-1-[3-(4-acetylphenyl)phenyl]-1,4-dihydro[1,8]naphthyridin-4-one-3-carboxamide

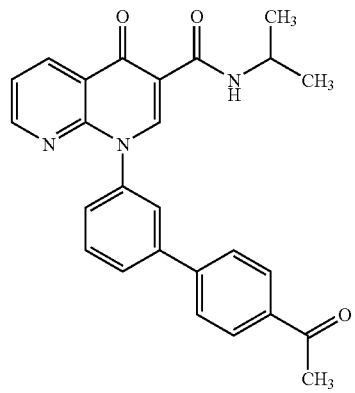

Following the procedure of Step 5 of Example 1, but substituting 4-acetylphenylboronic acid for 3-acetylphenylboronic acid the title compound was obtained as a solid.

$^1$H NMR (Acetone-$d_6$) δ 1.25 (d, 6H), 2.61 (s, 3H), 4.17 (m, 1H), 7.59 (m, 1H), 7.70 (d, 1H), 7.76 (t, 1H), 7.92 (d, 2H), 7.97 (d, 1H), 8.07-8.10 (m, 3H), 8.72 (brs, 1H), 8.78 (dd, 1H), 8.92 (s, 1H), 9.65 (br, NH).

Example 5

N-Isopropyl-1-[3-(2-methylphenyl)phenyl]-1,4-dihydro[1,8]naphthyridin-4-one-3-carboxamide

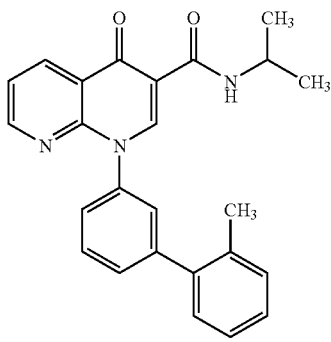

Following the procedure of Step 5 of Example 1, but substituting 2-methylphenylboronic acid for 3-acetylphenylboronic acid the title compound was obtained as a solid.

$^1$H NMR (Acetone-d$_6$) δ.1.24 (d, 6H), 2.35 (s, 3H), 4.17 (m, 1H), 7.27-7.34 (m, 4H), 7.56-7.60 (m, 2H), 7.65 (m, 2H), 7.70 (t, 1H), 8.74 (m, 1H), 8.78 (dd, 1H), 8.92 (s, 1H), 9.64 (br, NH).

Example 6

N-Isopropyl-N-methyl-1-[3-(4-acetylphenyl)phenyl]-1,4-dihydro[1,8]naphthyridin-4-one-3-carboxamide

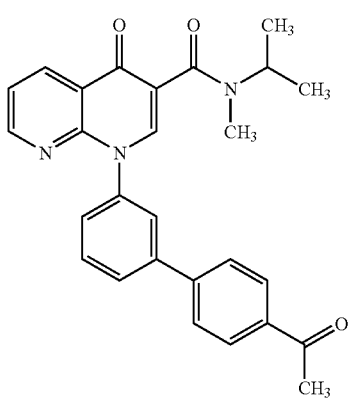

Step 1: N-Isopropyl-N-methyl-1-(3-bromophenyl)-1,4-dihydro[1,8]naphthyridin-4-one-3-carboxamide Following the procedure of Example 1, Step 4, but substituting N-isopropyl-N-methylamine for isopropylamine the N-Isopropyl-N-methyl-1-(3-bromophenyl)-1,4-dihydro[1,8]naphthyridin-4-one-3-carboxamide was obtained in as a yellow solid.

$^1$H NMR (Acetone-d$_6$) (Appears as two rotamers of the amide) δ 1.18 (m, 6H), 2.85 (s, 3H), 4.05 (m, 0.5H), 4.84 (m, 0.5H), 7.49-7.64 (m, 3H), 7.72 (d, 1H), 7.86 (s, 1H), 8.14 (s, 1H), 8.65 (d, 2H).

Step 2: N-Isopropyl-N-methyl-1-[3-(4-acetylphenyl)phenyl]-1,4-dihydro[1,8]naphthyridin-4-one-3-carboxamide Following the procedure of Step 5 of Example 1, but substituting N-isopropyl-N-methyl-1-(3-bromophenyl)-1,4-dihydro[1,8]naphthyridin-4-one-3-carboxamide from step 1 for N-isopropyl 1-(3-bromophenyl)-1,4-dihydro[1,8]naphthyridin-4-one-3-carboxamide and 4-acetylphenylboronic acid for 3-acetylphenylboronic acid the N-Isopropyl-N-methyl-1-[3-(4-acetylphenyl)phenyl]-1,4-dihydro[1,8]naphthyridin-4-one-3-carboxamide compound was obtained as a white solid.

$^1$H NMR (CDCl$_3$) (Appears as two rotamers of the amide) δ 1.23 (m, 6H), 2.62 (s, 3H), 4.00 (m, 0.5H), 4.92 (m, 0.5H), 7.38-7.55 (m, 2H), 7.63-7.77 (m, 5H), 8.03 (d, 2H), 8.14 (s, 0.5H), 8.21 (s, 0.5H), 8.65 (m, 1H), 8.75-8.80 (m, 1H).

Example 7

N-Isopropyl-1-[3-(pyridin-3-yl)phenyl]-1,4-dihydro[1,8]naphthyridin-4-one-3-carboxamide

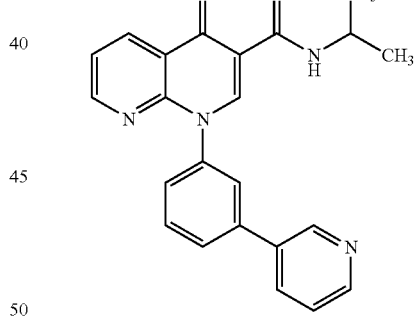

Following the procedure of Step 5 of Example 1, but substituting pyridine-3-boronic acid 1,3-propanediol cyclic ester for 3-acetylphenylboronic acid and [1,1'-bis (diphenylphosphino)ferrocene]dichloropalladium(II) for trans-dibromobis(triphenylphosphine)palladium (II) the title compound was obtained as a beige solid.

$^1$H NMR (Acetone-d$_6$) δ 1.24 (d, 6H), 4.17 (m, 1H), 7.48 (m, 1H), 7.60 (m, 1H), 7.71 (dd, 1H), 7.78 (t, 1H), 7.95 (dd, 1H), 8.05 (brs, 1H), 8.15 (m, 1H), 8.60 (m, 1H), 8.72 (m, 1H), 8.78 (dd, 1H), 8.92 (s, 1H), 8.99 (brs, 1H), 9.65 (br, NH).

Example 8

N-Isopropyl-1-[3-(indol-5-yl)phenyl]-1,4-dihydro[1,8]naphthyridin-4-one-3-carboxamide

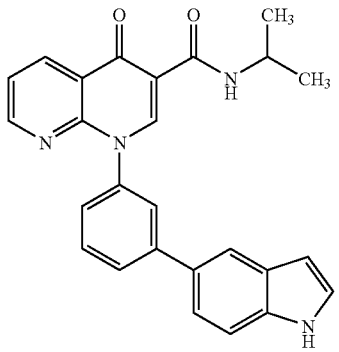

Following the procedure of Step 5 of Example 1, but substituting 5-indolylboronic acid for 3-acetylphenylboronic acid the title compound was obtained as an off-white solid.

$^1$H NMR ((DMSO-$d_6$) δ 1.20 (d, 6H), 4.10 (m, 1H), 6.47 (s, 1H), 7.38 (brs, 1H), 7.46-7.52 (m, 3H), 7.59-7.66 (m, 2H), 7.87-7.93 (m, 3H), 8.72-8.81 (m, 3H), 9.67 (br, NH), 11.2 (br, NH).

Example 9

N-tert-Butyl-1-[3-(4-acetylphenyl)phenyl]1,4-dihydro[1,8]naphthyridin-4-one-3-carboxamide

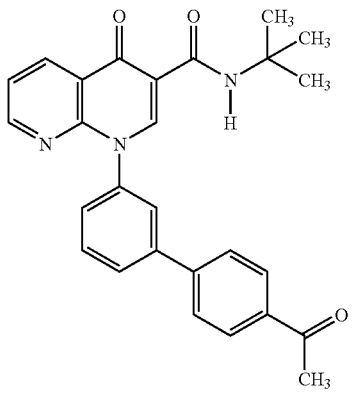

Step 1: N-tert-Butyl-1-(3-bromophenyl)-1,4-dihydro[1,8]naphthyridin-4-one-3-carboxamide Following the procedure of Example 1, Step 4, but substituting tert-butylamine for isopropylamine the N-tert-Butyl-1-(3-bromophenyl)-1,4-dihydro[1,8]naphthyridinone-3-carboxamide was obtained as a yellow solid.

$^1$H NMR (Acetone-$d_6$) δ 1.44 (s, 9H), 7.58-7.62 (m, 2H), 7.70 (dd, 1H), 7.78 (dd, 1H), 7.93 (br s, 1H), 8.72 (m, 1H), 8.77 (dd, 1H), 8.81 (s, 1H), 9.73 (br, NH).

Step 2: N-tert-Butyl-1-[3-(4-acetylphenyl)phenyl]-1,4-dihydro[1,8]naphthyridin-4-one-3-carboxamide Following the procedure of Step 5 of Example 1, but substituting N-tert butyl-1-(3-bromophenyl)-1,4-dihydro[1,8]naphthyridin-4-one-3-carboxamide from step 1 for N-isopropyl 1-(3-bromophenyl)-1,4-dihydro[1,8]naphthyridin-4-one-3-carboxamide and 4-acetylphenylboronic acid for 3-acetylphenylboronic acid the N-tert-Butyl-1-[3-(4-acetylphenyl)phenyl]-1,4-dihydro[1,8]naphthyridin-4-one-3-carboxamide compound was obtained in 93% yield as a white solid.

$^1$H NMR (Acetone-$d_6$) δ 1.45 (s, 9H), 2.61 (s, 3H), 7.59 (m, 1H), 7.69-7.72 (m, 1H), 7.77 (t, 1H), 7.92-7.99 (m, 3H), 8.07-8.11 (m, 3H), 8.72 (m, 1H), 8.78 (dd, 1H), 8.91 (s, 1H), 9.79 (br, NH).

Example 10

N-(2,6-Dichloropyridin-4-yl)-1-[3-(pyridin-3-yl)phenyl]-1,4-dihydro[1,1]naphthyridin-4-one-3-carboxamide

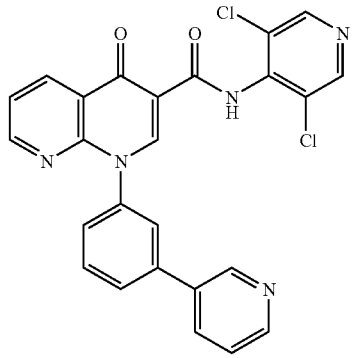

Following the procedure of Step 4 of Example 2 but substituting [1,1'-bis (diphenylphosphino)ferrocene]dichloropalladium(II) for trans-dibromobis(triphenylphosphine) palladium (II) and pyridine-3-boronic acid 1,3-propanediol cyclic ester for 3-acetylphenylboronic acid the title compound was obtained as a glassy solid.

$^1$H NMR (Acetone-$d_6$) δ 7.48 (m, 1H), 7.68 (m, 1H), 7.77-7.82 (m, 2H), 7.98 (m, 1H), 8.12-8.17 (m, 2H), 8.61 (m, 1H), 8.62 (s, 2H), 8.80 (m, 1H), 8.88 (dd, 1H), 8.99 (brs, 1H), 9.06 (s, 1H), 12.2 (br, NH).

Example 11

N-Isopropyl-1-{3-[4-(4-tertbutyloxycarbonylpiperazin-1-yl)phenyl]-phenyl}-1,4-dihydro[1,8]naphthyridin-4-one-3-carboxamide

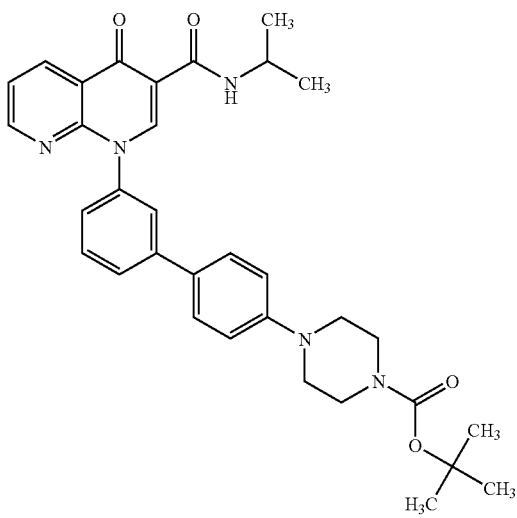

Step 1: 4-tert-Butyloxycarbonyl-1-(3-bromophenyl)piperazine

To a suspension of 1-(4-bromophenyl)piperazine hydrochloride (103.15 g, 371.59 mmol) in acetonitrile (1.5 L) at 0° C. under a nitrogen atmosphere was added a catalytic amount of 4-dimethylaminopyridine (4.54 g, 37.159 mmol) followed by triethylamine (155 mL, 1114.77 mmol) and di-tert-butyl dicarbonate (121.65 g, 557.385 mmol, dissolved in a minimum amount of acetonitrile) and the resulting reaction mixture was warmed to room temperature and stirred for 5.5 hours. The reaction mixture was filtered, ethyl acetate was added and the organic phase was washed with 10% aqueous citric acid, water (2×) and brine, then dried and evaporated to afford the crude 4-tert-Butyloxycarbonyl-1-(3-bromophenyl)piperazine product which was used as such in the next step.

Step 2: 3-(4-tert-Butyloxycarbonylpiperazin-1-yl)phenylboronic acid

To the 4-tert-Butyloxycarbonyl-1-(3-bromophenyl)piperazine from Step 1 (118.30 g, 346.9 mmol) in tetrahydrofuran/toluene (1/1, 1.5 L) at −78° C. under nitrogen was added n-butyllithium (2.5M, 160 mL, 398.9 mmol) dropwise and the resulting reaction mixture was stirred at −78° C. for 20 minutes. Triisopropyl borate (96.4 mL, 416.3 mmol) was added dropwise and the reaction was warmed to 0° C. and stirred for 2 hours. Aqueous saturated ammonium chloride (400 mL), water (100 mL) and 1 equivalent of H$_3$PO$_4$ (20 mL) were added and the mixture was stirred for 15 minutes and then concentrated to a volume of approximately 200 mL (at which stage the mixture became bluish and a precipitate formed). The mixture was slowly diluted with heptane (800 mL) and the resulting suspension was stirred overnight. The suspension was filtered, the solid was washed with heptane and dried to afford the title boronic acid.

Step 3: N-Isopropyl-1-{3-[4-(4-tertbutloxycarbonylpiperazin-1-yl)phenyl]-phenyl}-1,4-dihydro[1,8]naphthyridin-4-one-3-carboxamide Following the procedure of Step 5 of Example 1 but substituting [1,1'-bis (diphenylphosphino)ferrocene]dichloropalladium(II) for trans-dibromobis(triphenylphosphine)palladium (II) and the boronic acid from Step 2 above for 3-acetylphenylboronic acid the 4-tert-Butyloxycarbonyl-1-(3-bromophenyl)piperazine compound was obtained as a solid.

$^1$H NMR (CDCl$_3$) δ 1.30 (d, 6H), 1.49 (s, 9H), 3.18 (m, 4H), 3.58 (m, 4H), 4.29 (m, 1H), 6.98 (d, 2H), 7.32 (d, 1H), 7.45 (m, 1H), 7.53 (d, 2H), 7.55-7.62 (m, 2H), 7.72 (d, 1H), 8.70 (m, 1H), 8.82 (d, 1H), 9.07 (s, 1H), 9.68 (br, NH).

Example 12

N-Isopropyl-1-[3-(quinolin-3-yl)phenyl]-1,4-dihydro[1,8]naphthyridin-4-one-carboxamide

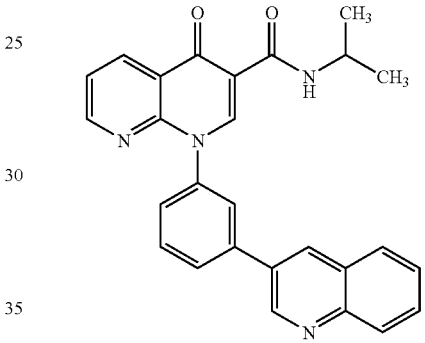

Following the procedure of Step 5 of Example 1, but substituting 3-quinolineboronic acid for 3-acetylphenylboronic acid the title compound was obtained as a solid.

$^1$H NMR (CDCl$_3$) δ 1.29 (d, 6H), 4.29 (m, 1H), 7.49 (m, 2H), 7.61 (t, 1H), 7.70-7.78 (m, 3H), 7.86-7.92 (m, 2H), 8.14 (d, 1H), 8.36 (s, 1H), 8.71 (m, 1H), 8.84 (dd, 1H), 9.10 (s, 1H), 9.19 (s, 1H), 9.67 (br, NH).

Example 13

N-Isopropyl-1-[3-(pyrimidin-5-yl)phenyl]-1,4-dihydro[1,8]naphthyridin-4-one-carboxamide

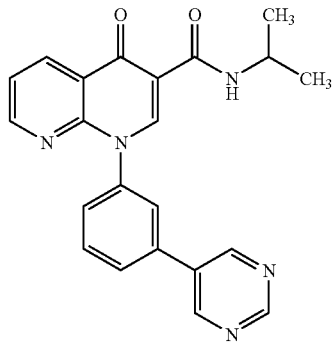

Following the procedure of Step 5 of Example 1, but substituting 5-pyrimidineboronic acid for 3-acetylboronic acid the title compound was obtained as a solid.

$^1$H NMR (CDCl$_3$) δ 1.28 (d, 6H), 4.27 (m, 1H), 7.48 (dd, 1H), 7.52 (m, 1H), 7.65 (s, 1H), 7.74 (m, 2H), 8.68 (m, 1H), 8.72 (d, 1H), 8.98 (s, 2H) 9.03 (s, 1H), 9.22 (s, 1H), 9.62 (br, NH).

Example 14

N-Cyclopropyl-1-[3-(pyridin-3-yl)phenyl]-1,4-dihydro[1,8]naphthyridin-4-one-3-carboxamide

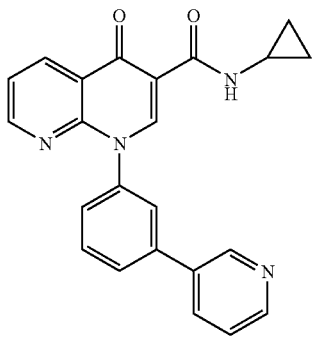

Step 1: N-Cyclopropyl-1-(3-bromophenyl)-1,4-dihydro[1,8]naphthyridin-4-one-3-carboxamide Following the procedure of Example 1, Step 4, but substituting cyclopropylamine for isopropylamine the N-Cyclopropyl-1-(3-bromophenyl)-1,4-dihydro[1,8]naphthyridin-one-3-carboxamide was obtained as a fluffy white solid.

$^1$H NMR (Acetone-d$_6$) δ 0.59 (m, 2H), 0.80 (m, 2h), 2.96 (m, 1H), 7.59-7.68 (m, 2H), 7.72 (dd, 1H), 7.82 (dd, 1H), 7.97 (s, 1H), 8.72-8.81 (m, 2H), 8.89 (s, 1H), 9.70 (br, NH).

Step 2: N-Cyclopropyl-1-[3-(pyridin-3-yl)phenyl]-1,4-dihydro[1,8]naphthyridin-4-one-3-carboxamide Following the procedure of Example 7 but substituting N-cyclopropyl-1-(3-bromophenyl)-1,4-dihydro[1,8]naphthyridin-4-one-3-carboxamide from step 1 for N-isopropyl-1-(3-bromophenyl)-1,4-dihydro[1,8]naphthyridin-4-one-3-carboxamide, the N-Cyclopropyl-1-[3-(pyridin-3-yl)phenyl]-1,4-dihydro[1,8]naphthyridin-4-one-3-carboxamide compound was obtained as a cream-coloured solid.

$^1$H NMR (DMSO-d$_6$) δ 0.57 (m, 2H), 0.78 (m, 2H), 2.91 (m, 1H), 7.52 (m, 1H), 7.63-7.69 (m, 2H), 7.74 (t, 1H), 7.97 (d, 1H), 8.07 (brs, 1H), 8.17 (d, 1H), 8.61 (m, 1H), 8.73 (dd, 1H), 8.79 (m, 1H), 8.85 (s, 1H), 8.99 (brs, 1H), 9.74 (br, NH).

Example 15

N-Isopropyl-1-[3-(5-methylthiopyridin-3-yl)phenyl]-1,4-dihydro[1,8]naphthyridin-4-one-3-carboxamide

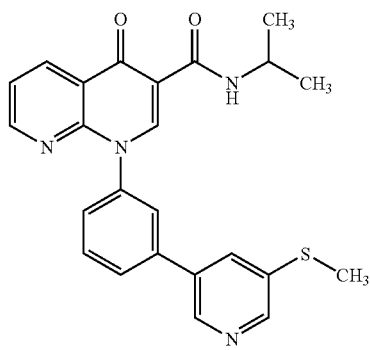

Following the procedure of Step 5 of Example 1 but substituting 5-methylthiopyridine-3-boronic acid for 3-acetylphenylboronic acid and [1,1'-bis (diphenylphosphino)ferrocene]dichloropalladium(II) for trans-dibromobis(triphenylphosphine)palladium (1) the title compound was obtained as a solid.

$^1$H NMR (CDCl$_3$) δ 1.33 (d, 6H) 2.60 (s, 3H), 4.33 (m, 1H), 7.48-7.54 (m, 2H), 7.66 (m, 1H), 7.73 (t, 1H), 7.78-7.81 (m, 2H), 8.55 (s, 1H), 8.66 (s, 1H), 8.74 (m, 1H), 8.87 (d, 1H), 9.09 (s, 1H), 9.69 (br, NH).

Example 16

N-Cyclopropyl-1-[3-(4-hydroxymethylphenyl)phenyl]-1,4-dihydro[1,8]naphthyridin-4-one-3-carboxamide

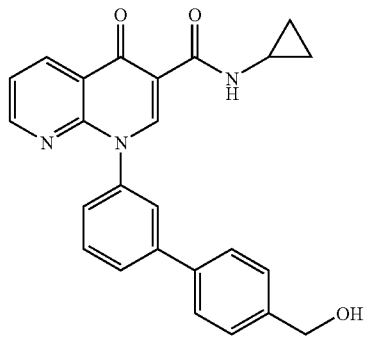

Following the procedure of Step 2 of Example 14 but substituting 4-hydroxymethylphenyl boronic acid for pyridine-3-boronic acid 1,3-propanediol cyclic ester the title compound was obtained as a solid.

$^1$H NMR (CDCl$_3$) δ 0.71 (m, 2H), 0.89 (m, 2H), 1.88 (t, 1H), 3.03 (m, 1H), 4.78 (d, 2H), 7.43 (d, 1H), 7.46-7.52 (m, 3H), 7.61-7.69 (m, 4H), 7.80 (d, 1H), 8.73 (dd, 1H), 8.83 (dd, 1H), 9.10 (s, 1H), 9.82 (br, NH).

Example 17

N-Cyclopropyl-1-[3-(pyridin-4-yl)phenyl]-1,4-dihydro[1,8]naphthyridin-4-one-3-carboxamide

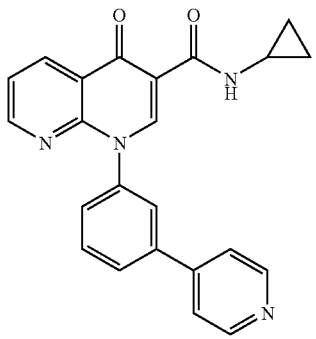

Following the procedure of Step 5 of Example 1 but substituting N-cyclopropyl-1-(3-bromophenyl)-1,4-dihydro[1,8]naphthyridin-4-one-3-carboxamide for N-isopropyl-1-(3-bromophenyl)-1,4-dihydro[1,8]naphthyridinone-3-carboxamide and 4-pyridineboronic acid for 3-acetylphenylboronic acid the title compound was obtained as a white solid.

$^1$H NMR ((DMSO-$d_6$) δ 0.57 (m, 2H), 0.77 (m, 2H), 2.90 (m, 1H), 7.64 (m, 1H), 7.72-7.89 (m, 4H), 8.03 (d, 1H), 8.13 (s, 1H), 8.66-8.78 (m, 4H), 8.84 (s, 1H), 9.72 (br, NH).

Example 18

N-Cyclopropyl-1-[3-(4-ethylthiophenyl)phenyl]-1,4-dihydro[0.8]naphthyridin-4-one-3-carboxamide

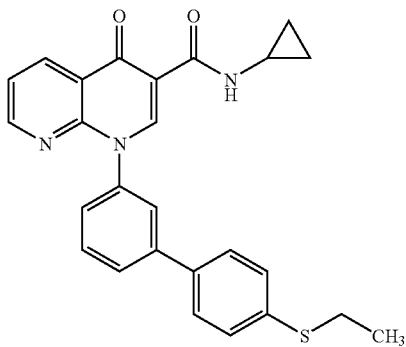

Following the procedure of Step 2 of Example 14 but substituting 4-ethylthiobenzeneboronic acid for pyridine-3-boronic acid 1,3-propanediol cyclic ester the title compound was obtained as a solid.

$^1$H NMR (CDCl$_3$) δ 0.72 (m, 2H), 0.90 (m, 2H), 1.48 (t, 3H), 3.03 (m, 3H), 7.42 (d, 3H), 7.50 (m, 1H), 7.57 (d, 2H), 7.64 (s, 1H), 7.68 (t, 1H), 7.78 (d, 1H), 8.75 (m, 1H); 8.85 (d, 1H), 9.10 (s, 1H), 9.83 (br, NH).

Example 19

N-Cyclopropyl-1-[3-(3-thienyl)phenyl]-1,4-dihydro[1,8]naphthyridin-4-one-3-carboxamide

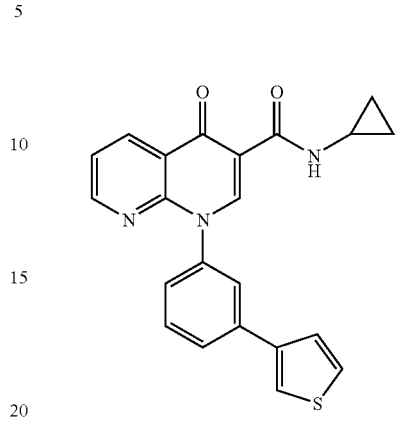

Following the procedure of Step 2 of Example 14 but substituting 3-thiopheneboronic acid for pyridine-3-boronic acid 1,3-propanediol cyclic ester the title compound was obtained as a white solid.

$^1$H NMR (Acetone-$d_6$) δ0.60 (m, 2H), 0.79 (m, 2H), 2.96 (m, 1H), 7.57-7.72 (m, 5H), 7.92-7.98 (m, 2H), 8.05 (s, 1H), 8.74 (s, 1H), 8.78 (d, 1H), 8.93 (s, 1H), 9.74 (br, NH).

Example 20

N-Cyclopropyl-1-[3-(4-sulfamoylphenyl)phenyl]-1,4-dihydro[1,8]naphthyridin-4-one-3-carboxamide

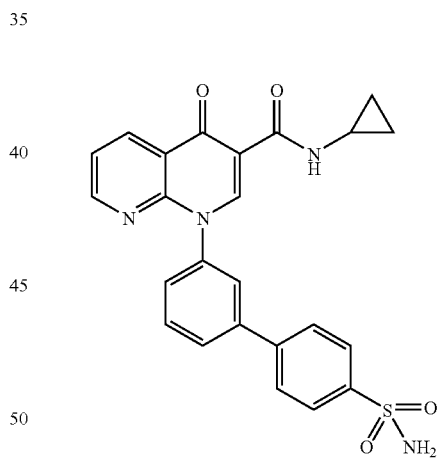

Step 1: 4-Sulfamoylbenzeneboronic acid pinacol ester

A mixture of 4-bromobenzenesulfonamide, diboron pinacol ester (1.1 eq), potassium acetate (3.5 eq) and 1,1'-bis(diphenylphosphino)ferrocene]dichloropalladium(II) (0.05 eq) im N,N-dimethylformamide (4 ml/mmol) was heated at 85° C. for 18 hours. After quenching with saturated aqueous ammonium chloride solution the mixture was partitioned between ethyl acetate and water and the product from the organic phase was chromatographed on silica gel eluting with a 1:1 mixture of ethyl acetate and hexane to afford the 4-Sulfamoylbenzeneboronic acid pinacol ester as a solid.

Step 2: N-Cyclopropyl-1-[3-(4-sulfamoylphenyl)phenyl]-1,4-dihydro[1,8]naphthyridin-4-one-3-carboxamide A mixture of N-cyclopropyl-1-(3-bromophenyl)-1,4-dihydro[1,8]naphthyridin-4-one-3-carboxamide, boronate from Step 1 (1.2 eq), palladium acetate (0.1 eq), triphenylphosphine (0.35 eq) and 2M aqueous sodium carbonate (3.5 eq) in n-propanol (10 ml/mmol) was stirred at 85° C. for 1 hour. After cooling, the mixture was quenched with saturated aqueous ammonium chloride solution and partitioned between ethyl acetate and water, and the product from the organic phase was chromatographed on silica gel eluting with a 1:5:4 mixture of ethanol, ethyl acetate and methylene chloride to afford the N-Cyclopropyl-1-[3-(4-sulfamoylphenyl)phenyl]-1,4-dihydro[1,8]naphthyridinone-3-carboxamide compound as a solid.

$^1$H NMR (Acetone-$d_6$) δ 0.62 (m, 2H), 0.82 (m, 2H), 2.98 (m, 1H), 6.66 (br, NH$_2$), 7.64 (m, 1H), 7.74 (m, 1H), 7.80 (t, 1H), 7.97-8.05 (m, 5H), 8.10 (m, 1H), 8.76 (m, 1H), 8.81 (dd, 1H), 8.97 (s, 1H), 9.77 (br, NH).

Example 21

N-Isopropyl-1-[3-(3-ethoxyphenyl)phenyl]-1,4-dihydro[1,8]naphthyridin-4-one-3-carboxamide

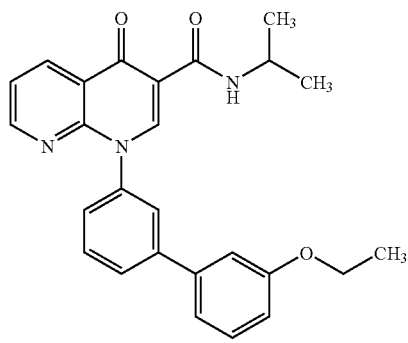

Step 1: Ethel 1-[3-(3-ethoxyphenyl)phenyl]-1,4-dihydro[1,8]naphthyridin one-3-carboxylate Following the procedure of Step 5 of Example 1, but substituting ethyl 1-(3-bromophenyl)-1,4-dihydro[1,8]naphthyridinone-3-carboxylate from Step 2 of Example 1 for N-isopropyl-1-(3-bromophenyl)-1,4-dihydro[1,8]naphthyridin-4-one-3-carboxamide, and 3-ethoxybenzeneboronic acid for 3-acetylbenzeneboronic acid, the Ethyl 1-[3-(3-ethoxyphenyl)phenyl)-1,4-dihydro[1,8]naphthyridin-4-one-3-carboxylate compound was obtained as a solid.

Step 2: 1-[3-(3-Ethoxyphenyl)phenyl]-1,4-dihydro[1,8]naphthyridin-4-one-3-carboxylic acid Following the procedure of Step 3 of Example 1 but substituting ethyl 1-[3-(3-ethoxyphenyl)phenyl]-1,4-dihydro[1,8]naphthyridin-4-one-3-carboxylate from step 1 for ethyl 1-(3-bromophenyl)-1,4-dihydro[1,8]naphthyridin-4-one-3-carboxylate the 1-[3-(3-Ethoxyphenyl)phenyl]-1,4-dihydro[1,8]naphthyridinone-carboxylic acid compound was obtained and used without purification in the next step.

Step 3: N-Isopropyl-1-[3-(3-ethoxyphenyl)phenyl]-1,4-dihydro[1,8]naphthyridin-4-one-3-carboxamide A mixture of 1-[3-(3-ethoxyphenyl)phenyl]-1,4-dihydro(1,8]naphthyridin-4-one-3-carboxylic acid from Step 2 and thionyl chloride (4 eq) in tetrahydrofuran (10 ml/mmol) was refluxed for 45 minutes, then evaporated. The residue was dissolved in the same volume of tetrahydrofuran, isopropylamine (5 eq) was added and the mixture was stirred at room temperature for 18 hours. After quenching with saturated aqueous ammonium chloride solution, the resulting mixture was partitioned between ethyl acetate and water, and the product from the organic phase was chromatographed on silica gel eluting with 10% ether in methylene chloride to afford the N-Isopropyl-1-[3-(3-ethoxyphenyl)phenyl]-1,4-dihydro[1,8]naphthyridin-4-one-3-carboxamide compound as a solid.

$^1$H NMR (CDCl$_3$) δ 1.29 (d, 6H), 1.42 (t, 3H), 4.08 (q, 2H), 4.28 (m, 1H), 6.91 (d, 1H), 7.12 (s, 1H), 7.18 (d, 1H), 7.34 (t, 1H), 7.40 (d, 1H), 7.46 (m, 1H), 7.60-7.65 (m, 2H), 7.75 (d, 1H), 8.71 (brs, 1H), 8.82 (dd, 1H), 9.08 (s, 1H), 9.70 (br, NH).

Example 22

N-Isopropyl-1-[3-(4-methylthiophenyl)phenyl]-1,4-dihydro[1,8]naphthyridin-4-one-3-carboxamide

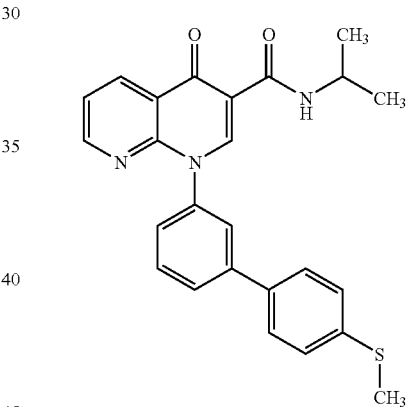

Step 1: Ethyl 1-[3-(4-methylthiophenyl)phenyl]-1,4-dihydro[1,8]naphthyridin-4-one-3-carboxylate Following the procedure of Step 5 of Example 1, but substituting ethyl 1-(3-bromophenyl)-1,4-dihydro[1,8]naphthyridin-4-one-3-carboxylate from step 2 of example 1 for N-isopropyl-1-(3-bromophenyl)-1,4-dihydro[1,8]naphthyridin-4-one-3-carboxamide, and 4-methylthiobenzeneboronic acid for 3-acetylbenzeneboronic acid, the Ethyl 1-[3-(4-methylthiophenyl)phenyl]-1,4-dihydro[1,8]naphthyridin-4-one-3-carboxylate compound was obtained as a solid.

Step 2: 1-[3-(4-methylthiophenyl)phenyl]-1,4-dihydro[1,8]naphthyridin-4-one-3-carboxylic acid Following the procedure of Step 3 of Example 1 but substituting ethyl 1-[3-(4-methylthiophenyl)phenyl]-1,4-dihydro[1,8]naphthyridin-4-one-3-carboxylate from Step 1 for ethyl 1-(3-bromophenyl)-1,4-dihydro[1,8]naphthyridin-4-one-3-carboxylate the 1-[3-(4-methylthiophenyl)phenyl]-1, 4-dihydro[1,8]naphthyridin-4-one-3-carboxylic acid compound was obtained as a solid.

Step 3: N-Isopropyl-1-[3-(4-methylthiophenyl)phenyl]-1,4-dihydro[1,8]naphthyridin-4-one-3-carboxamide Following the procedure of Step 3 of Example 21 but substituting 1-[3-(4-methylthiophenyl)phenyl]-1,4-dihydro[1,8]naphthyridin-4-one-3-carboxylic acid for 1-[3-(3-ethoxyphenyl)phenyl]-1,4-dihydro[1,8]naphthyridin-4-one-3-carboxylic acid the N-Isopropyl-1-[3-(4-methylthiophenyl)phenyl]-1,4-dihydro[1,8]naphthyridin-4-one-3-carboxamide compound was obtained as a white solid.

$^1$H NMR (Acetone-$d_6$) δ1.24 (d, 6H), 2.52 (s, 3H), 4.18 (m, 1H), 7.37 (d, 2H), 7.58-7.62 (m, 2H), 7.69-7.73 (m, 3H), 7.87 (d, 1H), 7.96 (s, 1H), 8.72 (m, 1H), 8.78 (dd, 1H), 8.91 (s, 1H), 9.65 (br, NH).

Example 23

N-Isopropyl-1-[3-(3-acetyl-4-hydroxyphenyl)phenyl]-1,4-dihydro[1,8]naphthyridin-4-one-3-carboxamide

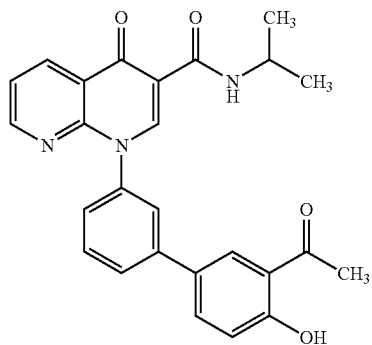

A mixture of 5'-bromo-2'-hydroxyacetophenone, diboron pinacol ester (1.25 eq), potassium acetate (3 eq) and [1,1'-bis(diphenylphosphino)ferrocene]dichloropalladium(II) (0.05 eq) in N,N-dimethylformamide (10 mmol) was stirred at 80° C. for 3 hours and cooled down. A solution of N-Isopropyl-1-(3-bromophenyl)-1,4-dihydro[1,8]naphthyridin-4-one-3-carboxamide from Example 1, Step 4 (0.75 eq) in N,N-dimethylformamide (7 ml/mmol), [1,1'-bis(diphenylphosphino)ferrocene]dichloropalladium(1) (0.05 eq) and 2M aqueous sodium carbonate (8.5 eq) were added and the resulting mixture was stirred at 80° C. for 2.5 hours. The cooled mixture was partitioned between ethyl acetate and water and the product from the organic phase was chromatographed on silica gel eluting with 60% ethyl acetate in hexane to afford the title compound as a light yellow solid.

$^1$H NMR (Acetone-$d_6$) δ 1.24 (d, 6H), 2.75 (s, 3H), 4.19 (m, 1H), 7.06 (d, 1H), 7.59-7.63 (m, 2H), 7.72 (t, 1H), 7.92 (d, 1H), 7.97 (d, 1H), 8.02 (s, 1H), 8.33 (s, 1H), 8.73 (m, 1H), 8.78 (dd, 1H), 8.90(s, 1H), 9.65 (br, NH).

Example 24

N-Isopropyl-1-[3-(5-carboethoxypyridin-3-yl)phenyl]-1,4-dihydro[1,8]naphthyridin-4-one-3-carboxamide

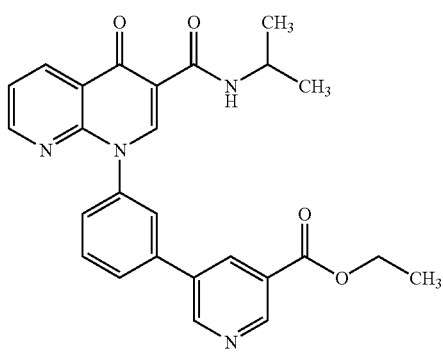

Following the procedure of Example 23 but substituting N-isopropyl-1-(3-bromophenyl)-1,4-dihydro[1,8]naphthyridin-4-one-3-carboxamide for 5'-bromo-2'-hydroxyacetophenone and ethyl 5-bromonicotinate for N-isopropyl-1-(3-bromophenyl)-1,4-dihydro[1,8]naphthyridin-4-one-3-carboxamide the title compound was obtained as a beige solid.

$^1$H NMR (CDCl$_3$) δ 1.29 (d, 6H), 1.40 (t, 3H), 4.28 (m, 1H), 4.42 (q, 2H), 7.45-7.51 (m, 2), 7.68 (s, 1H), 7.71 (t, 1H), 7.80 (d, 1H), 8.49 (s, 1H), 8.59 (m, 1H), 8.82 (d, 1H), 9.03 (s, 1H), 9.07 (s, 1H), 9.23 (s, 1H), 9.64 (br, NH).

Example 25

N-Isopropyl-1-{3-[5-(1-hydroxy-1-methylethyl)pyridin-3-yl]phenyl}-1,4-dihydro[1,8]naphthyridin-4-one-3-carboxamide

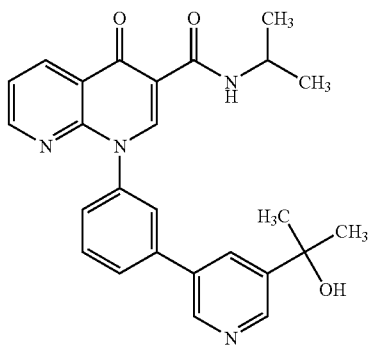

Step 1:
3-Bromo-5-(1-hydroxy-1-methylethyl)pyridine

To a solution of ethyl 5-bromonicotinate (1.02 g, 4.4 mmol) in diethyl ether (15 ml) at −30° C. was added a 3M solution of methyl magnesium bromide (4 ml, 12 mmol) in ether. The resulting slurry was then refluxed for 2 hours then cooled and quenched with an excess of 0.5M aqueous monobasic sodium phosphate and partitioned between ether and water. The product from the organic phase was chromatographed on silica gel eluting with a 2:1:2 mixture of ether, pentane and ammonia-saturated methylene chloride to afford the 3-Bromo-5-(1-hydroxy-1-methylethyl)pyridine compound as a yellow oil.

Step 2: N-Isopropyl-1-{3-[5-(1-hydroxy-1-methylethyl)pyridin-3-yl]phenyl}-1,4-dihydro[1,8]naphthyridin-4-one-3-carboxamide Following the procedure of Example 24, but substituting the 3-bromo-5-(1-hydroxy-1-methylethyl)pyridine from Step 1 for ethyl 5-bromonicotinate, the title compound was obtained as a yellow foam.

$^1$H NMR (CDCl$_3$) δ 1.28 (d, 6H), 1.62 (s, 6H), 2.52 (brs, 1H), 4.25 (m, 1H), 7.41-7.48 (m, 2H), 7.60-7.68 (m, 2H), 7.75 (d, 1H), 8.05 (s, 1H), 8.67-8.71 (m, 3H), 8.80 (dd, 1H), 9.03 (s, 1H), 9.66 (br, NH).

Example 26

N-Isopropyl-1-{3-[6-(2-methylpropyl)pyridin-3-yl]phenyl}-1,4-dihydro[1,8]naphthyridin-4-one-3-carboxamide

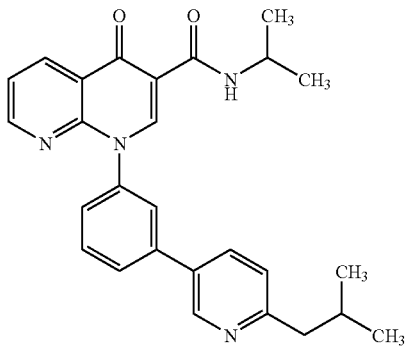

Step 1: 5-Bromo-2-(2-methylpropyl)pyridine

To a solution of 2,5-dibromopyridine (4.5 g, 19 mmol) in tetrahydrofuran (50 ml) was added [1,1'-bis (diphenylphosphino)ferrocene]dichloronickel (II) (103 mg, 0.19 mmol) and the resulting mixture was cooled to −10° C. A 2M solution of isobutylmagnesium bromide in ether (12.4 ml, 24.7 mmol) was added slowly and the mixture was stirred at −10 to 10° C. for 3.5 hours. After quenching with saturated aqueous ammonium chloride solution, the mixture was partitioned between ether and water and the product from the organic phase was chromatographed on silica gel eluting with 10% ether in pentane to afford the 5-Bromo-2-(2-methylpropyl)pyridine compound as a volatile oil.

Step 2: N-Isopropyl-1-{3-[6-(2-methylpropyl)pyridin-3-yl]phenyl}-1,4-dihydro[1,8]naphthyridin-4-one-3-carboxamide Following the procedure of Example 24 but substituting 5-bromo-2-(2-methylpropyl)pyridine from Step 1 for ethyl 5-bromonicotinate the N-Isopropyl-1-{3-[6-(2-methylpropyl)pyridin-3-yl]phenyl}-1,4-dihydro[1,8]naphthyridin-4-one-3-carboxamide compound was obtained as a white solid.

$^1$H NMR (CDCl$_3$) δ 0.92 (d, 6H), 1.28 (d, 6H), 2.10 (m, 1H), 2.69 (d, 2H), 4.28 (m, 1H), 7.19 (d, 1H), 7.40-7.47 (m, 2H), 7.60 (s, 1H), 7.64 (t, 1H), 7.73 (d, 1H), 7.79 (dd, 1H), 8.68 (m, 1H), 8.77-8.83 (m, 2H), 9.05 (s, 1H), 9.66 (br, NH).

Example 27

N-Isopropyl-1-[3-(5-acetylpyridin-3-yl)phenyl]-1,4-dihydro[1,8]naphthyridin-4-one-3-carboxamide

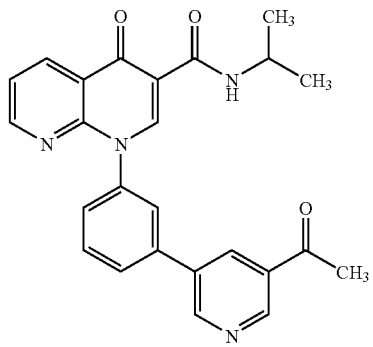

Step 1: 3-Acetyl-5-bromopyridine

To a solution of ethyl 5-bromonicotinate (3.9 g, 16.9 mmol) in ether (50 ml) at 0° C. was added a 3M solution of methylmagnesium bromide (16.9 ml, 50.8 mmol). The resulting thick slurry was warmed slowly to room temperature and after 1.5 hours it was poured slowly into an excess of 1M aqueous monobasic sodium phosphate. The mixture was partitioned between ether and water and the product from the organic phase was chromatographed on silica gel, eluting with a 1:1:2 mixture of ether, pentane and ammonia-saturated methylene chloride to afford the 3-acetyl-5-bromopyridine compound. This preparation also afforded 3-bromo-5-(1-hydroxy-1-methylethyl)pyridine described in Example 25.

Step 2: N-Isopropyl-1-[3-(5-acetyl pyridin-3-yl)phenyl]-1,4-dihydro[1,8]naphthyridin-4-one-3-carboxamide Following the procedure of Example 23 but substituting 3-acetyl-5-bromopyridine from Step 1 for ethyl 5-bromonicotinate the N-isopropyl-1-[3-(5-acetylpyridin-3-yl)phenyl]-1,4-dihydro[1,8]naphthyridin-4-one-3-carboxamide compound was obtained as a white solid.

$^1$H NMR (CDCl$_3$) δ 1.29 (d, 6H), 2.69 (s, 3H), 4.28 (m, 1H), 7.48 (dd, 1H), 7.51 (d, 1H), 7.69 (s, 1H), 7.72 (t, 1H), 7.80 (d, 1H), 8.42 (s, 1H), 8.69 (m, 1H), 8.82 (d, 1H), 9.05 (s, 2H) 9.17 (s, 1H), 9.63 (br, NH).

Example 28

N-Isopropyl-1-[3-(6-methylpyridin-3-yl)phenyl]-1,4-dihydro[1,8]naphthyridin-4-one-3-carboxamide

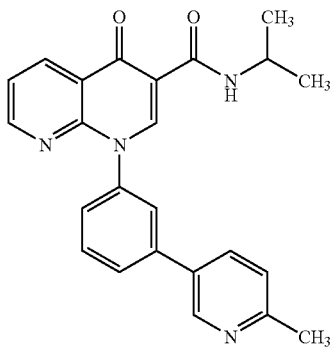

Step 1: 5-Bromo-2-methylpyridine

Following the procedure of Step 1 of Example 26 but substituting methylmagnesium chloride for isobutylmagnesium bromide the 5-bromo-2-methylpyridine compound was obtained as a solid.

Step 2: N-Isopropyl-1-[3-(6-methylpyridin-3-yl)phenyl]-1,4-dihydro[1,8]naphthyridin-4-one-3-carboxamide Following the procedure of Example 24 but substituting 5-bromo-2-methylpyridine from Step 1 for ethyl 5-bromonicotinate the N-Isopropyl-1-[3-(6-methylpyridin-3-yl)phenyl)-1,4-dihydro[1,8]naphthyridinone-3-carboxamide compound was obtained as a solid.

$^1$H NMR (CDCl$_3$) δ 1.32 (d, 6H), 2.63 (m, 3H), 4.30 (m, 1H), 7.25 (d, 1H), 7.45-7.51 (m, 2H), 7.63 (s, 1H), 7.69 (t, 1H), 7.77 (d, 1H), 7.82 (dd, 1H), 8.72 (m, 1H), 8.78 (s, 1H), 8.85 (d, 1H), 9.08 (s, 1H), 9.68 (br, NH).

Example 29

N-Cyclopropyl-1-[3-(1-oxidopyrimidin-5-yl)phenyl]-1,4-dihydro[1,8]naphthyridin-4-one-3-carboxamide

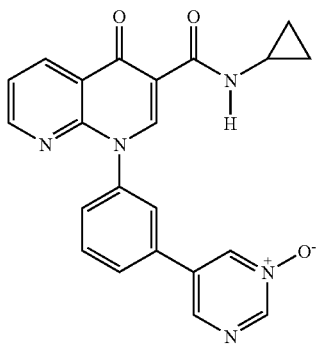

Step 1: 5-Bromo-1-oxidopyrimidine

To 5-bromopyrimidine (2.05 g, 12.9 mmol) in methylene chloride (25 ml) was added m-chloroperoxybenzoic acid (ca 70% pure, 3.17 g, 12.9 mmol) and the resulting mixture was stirred at room temperature for 5 days. Calcium hydroxide (1 g) was added and after 10 minutes the mixture was filtered through celite. The product from evaporation of the filtrate was chromatographed on silica gel eluting with ethyl acetate to afford the 5-bromo-1-oxidopyrimidine compound as a white solid.

Step 2: N-Cyclopropyl-1-[3-(1-oxidopyrimidinyl-5-yl)phenyl]-1,4-dihydro[1,8]naphthyridin-4-one-3-carboxamide Following the procedure of Example 24 but substituting 5-bromo-1-oxidopyrimidine from Step 1 for ethyl 5-bromonicotinate and N-cyclopropyl-1-(3-bromophenyl)-1,4-dihydro[1,8]naphthyridin-4-one-3-carboxamide for N-isopropyl-1-(3-bromophenyl)-1,4-dihydro[1,8]naphthyridin-4-one-3-carboxamide, the N-Cyclopropyl-1-[3-(1-oxidopyrimidinyl-5-yl)phenyl]-1,4-dihydro[1,8]naphthyridin-4-one-3-carboxamide compound was obtained as a white solid.

$^1$H NMR (CDCl$_3$) δ 0.66 (m, 2H), 0.84 (m, 2H), 2.97 (m, 1H), 7.48 (m, 1H), 7.58 (d, 1H), 7.65 (s, 1H), 7.71 (d, 1H), 7.77 (t, 1H), 8.46 (s, 1H), 8.60 (s, 1H), 8.68 (brs, 1H), 8.81 (dd, 1H), 8.98 (s, 1H), 9.02 (s, 1H), 9.72 (br, NH).

Example 30

1{-3-[6-(1-Hydroxy-1-methylethyl)-1-oxidopyridin-3-yl]phenyl}-1,4-dihydro[1,8]naphthyridin-4-one-3-carboxamide

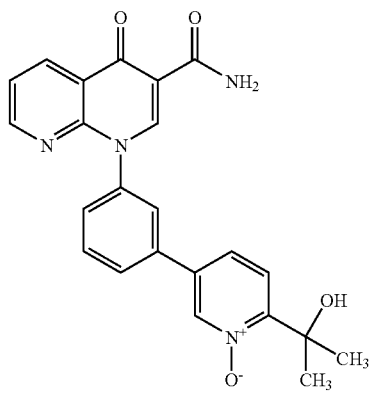

Step 1: 5-Bromo-2-(1-hydroxy-1-methylethyl)pyridine

To a suspension of 2,5-dibromopyridine in toluene (12 ml/mmol) cooled to −78° C. was added n-butyllithium 2.5M in hexanes (1.05 eq) and the resulting mixture was stirred in the cold for 2.5 hours. Acetone (2 eq) was added and stirring was continued for 1.5 h. After quenching with saturated aqueous ammonium chloride solution, the mixture was warmed to room temperature and partitioned between ethyl acetate and water. The product from the organic phase was chromatographed on silica gel eluting with 20% ethyl acetate in hexane to afford the 5-Bromo-2-(1-hydroxy-1-methylethyl)pyridine compound as a syrup.

Step 2: 5-Bromo-2-(1-hydroxy-1-methylethyl)pyridine N-oxide

To a solution of 5-bromo-2-(1-hydroxy-1-methylethyl) pyridine from Step 1 in methylene chloride (5 ml/mmol) at room temperature was added m-chloroperoxybenzoic acid 70% (1.1 eq) and the resulting mixture was stirred at room temperature for 18 hours. An excess of calcium hydroxide was added and after 5 minutes the mixture was filtered through a bed of celite. The crude product from evaporation of the filtrate was chromatographed on silica gel eluting with 80% ethyl acetate in hexane and the 5-bromo-2-(1-hydroxy-1-methylethyl)pyridine N-oxide compound was obtained as a white solid.

Step 3: 1-(3-bromophenyl)-1,4-dihydro[1,8]naphthyridin-4-one-3-carboxamide

Following the procedure of Step 4 of Example 1 but substituting 28% aqueous ammonium hydroxide for isopropylamine the 1-(3-bromophenyl)-1,4-dihydro[1,8]naphthyridin-4-one-3-carboxamide compound was obtained as a solid.

Step 4: 1-{3-[6-(1-hydroxy-1-methylethyl)-1-oxidopyridin-3-yl]phenyl}-1,4-dihydro[1,8]naphthyridin-4-one-3-carboxamide Following the procedure of Example 24 but substituting 5-bromo-2-(1-hydroxy-1-methylethyl)pyridine N-oxide from Step 2 above for ethyl 5-bromonicotinate and 1-(3-bromophenyl)-1,4-dihydro[1,8]naphthyridin-4-one-3-carboxamide for N-isopropyl-1-(3-bromophenyl)-1,4-dihydro [1,8]naphthyridin-4-one-3-carboxamide, the 1-{3-[6-(1-hydroxy-1-methylethyl)-1-oxidopyridin-3-yl]phenyl}-1,4-dihydro[1,8]naphthyridin-4-one-3-carboxamide compound was obtained as a solid.

$^1$H NMR (CDCl$_3$) δ 1.76 (s, 6H), 5.83 (br, 1H, NH). 7.50 (d, 1H), 7.55 (m, 1H), 7.57-7.62 (m, 2H), 7.65 (m, 2M), 7.72-7.78 (m, 2H), 8.55 (s, 1H, OH), 8.75 (m, 1H), 8.90 (dd, 1H), 9.08 (s, 1H), 9.52 (br, 1H, NH).

Example 31

N-Isopropyl-1-{3-[4-(pyridin-3-yl)phenyl]phenyl}-1,4-dihydro[1,8]naphthyridin-4-one-3-carboxamide

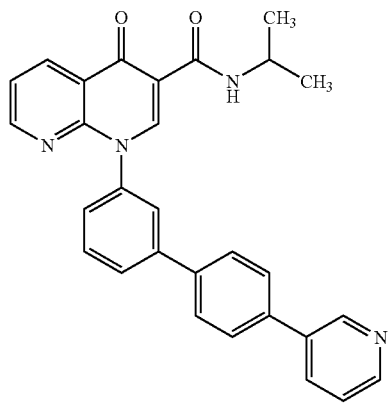

Step 1: N-Isopropyl-1-[3-(4,4,5,5,-tetramethyl-1,3,2-dioxaborolan-2-yl)phenyl]-1,4-dihydro[1,8]naphthyridin-4-one-3-carboxamide A mixture of N-isopropyl-1-(3-bromophenyl)-1,4-dihydro[1,8]naphthyridin-4-one-3-carboxamide from Step 4 of Example 1, diboron pinacol ester (1.1 eq), potassium acetate (3.5 eq) and [1,1'-bis (diphenylphosphino)ferrocene]dichloropalladium(II) (0.05 eq) in N,N-dimethylformamide (5 ml/mmol) was stirred at 85° C. for 18 hours. A further amount of diboron pinacol ester (0.4 eq) and palladium catalyst (0.05 eq) were added and heating and stirring were continued for a further 24 hours. After cooling, the mixture was partitioned between ethyl acetate and water, and the crude product from the organic phase was chromatographed on silica gel eluting with a 1:1 mixture of ethyl acetate and hexane. The product was then stirred in hexane at room temperature for several hours and filtered to afford the N-Isopropyl-1-[3-(4,4,5,5,-tetramethyl-1,3,2-dioxaborolan-2-yl)phenyl]-1,4-dihydro[1,8]naphthyridinone-3-carboxamide compound as a white solid.

Step 2: 3-(4-Bromophenyl)pyridine

A mixture of pyridine-3-boronic acid 1,3-propanediol cyclic ester, 4-bromoiodobenzene (1.1 eq), [1,1'-bis (diphenylphosphino)ferrocene]dichloropalladium(II) (0.05 eq) and 2M aqueous sodium carbonate (5 eq) in N,N-dimethylformamide (2 ml/mmol) was stirred at 85° C. for 4 hours. After quenching with saturated aqueous ammonium chloride solution, the mixture was partitioned between ethyl acetate and water, and the crude product from the organic phase was chromatographed on silica gel eluting with a 1:9 mixture of ethyl acetate and hexane to afford the 3-(4-Bromophenyl) pyridine compound as a solid.

Step 3: N-Isopropyl-1-{3-[4-(pyridin-3-yl)phenyl]phenyl}-1,4-dihydro[1,8]naphthyridin-4-one-3-carboxamide A mixture of the boronate from Step 1,3-(4-bromophenyl) pyridine from Step 2 (1.5 eq), [1,1'-bis (diphenylphosphino) ferrocene]dichloropalladium(II) (0.05 eq) and 2M aqueous sodium carbonate (5 eq) in N,N-dimethylformamide (7 ml/mmol) was stirred at 85° C. for 1 hour. After cooling, the mixture was partitioned between ethyl acetate and water. The crude product from the organic phase was chromatographed on silica gel eluting with a 7:3 mixture of ethyl acetate and methylene chloride to afford the N-Isopropyl-1-{3-[4-(pyridin-3-yl)phenyl]phenyl}-1,4-dihydro[1,8] naphthyridin-4-one-3-carboxamide compound as a solid.

$^1$H NMR (CDCl$_3$) δ 1.30 (d, 6H), 4.25 (m, 1H), 7.35 (m, 1H), 7.39-7.48 (m, 2H), 7.60-7.75 (m, 6H), 7.80 (d, 1H), 7.90 (d, 1H), 8.58 (d, 1H), 8.70 (m, 1H), 8.82 (d, 1H), 8.88 (s, 1H), 9.08 (s, 1H), 9.68 (br, NH).

Example 32

N-Cyclopropyl-1-[3-(5-methylsulfonylpyridin-3-yl)phenyl]-1,4-dihydro[1,8]naphthyridin-4-one-3-carboxamide

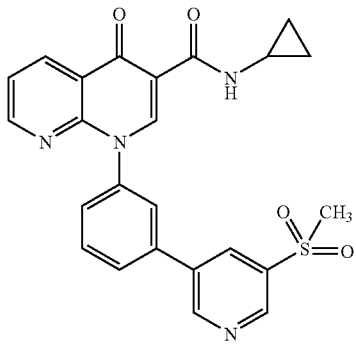

Step 1: N-Cyclopropyl-1-[3-(4,4,5,5,-tetramethyl-1,3,2-dioxaborolan-2-yl)phenyl]-1,4-dihydro[1,8]naphthyridin-4-one-3-carboxamide Following the procedure of Step 1 of Example 31 but substituting N-cyclopropyl-1-(3-bromophenyl)-1,4-dihydro[1,8]naphthyridin-4-one-3-carboxamide from step 1 of example 14 for N-isopropyl-1-(3-bromophenyl)-1,4-dihydro[1,8]naphthyridin-4-one-3-carboxamide the N-Cyclopropyl-1-[3-(4,4,5,5,-tetramethyl-1,3,2-dioxaborolan-2-yl)phenyl]-1,4-dihydro[1,8]naphthyridin-4-one-3-carboxamide compound was obtained as a white solid.

Step 2: 3-Bromo-5-methylsulfonylpyridine

To 3,5-dibromopyridine (2.96 g, 12.5 mmol) in diethyl ether (70 ml) at −78° C. was added n-butyllithium 1.6M in hexanes (8.6 ml, 13.7 mmol) and the resulting mixture was stirred in the cold for 3 hours. Dimethyl disulfide (1.12 ml, 12.5 mmol) was added and the mixture was warmed to room temperature, then partitioned between ether and water. To the crude product from evaporation of the organic phase was added tetrahydrofuran (80 ml), methanol (20 ml), oxone (17 g) and enough saturated aqueous sodium bicarbonate to afford a slightly basic medium. After stirring for 4 hours at room temperature, an excess of 1M aqueous sodium metabisulfite was added, the organic solvents were evaporated, and the residue was partitioned between ethyl acetate and water. The crude product from the organic phase was stirred in a small volume of ethyl acetate and filtered to afford the 3-Bromo-5-methylsulfonylpyridine compound as a solid.

Step 3: N-Cyclopropyl-1-[3-(5-methylsulfonylpyridin-3-yl)]phenyl]-1,4-dihydro[1,8]naphthyridin-4-one-3-carboxamide Following the procedure of Step 3 of Example 31 but substituting 3-bromo-5-methylsulfonylpyridine from Step 2 above for 3-(4-bromophenyl)pyridine, and N-cyclopropyl-1-[3-(4,4,5,5,-tetramethyl-1,3,2-dioxaborolan-2-yl)phenyl]-1,4-dihydro[1,8]naphthyridin-4-one-3-carboxamide from Step 1 for N-isopropyl-1-[3-(4,4,5,5,-tetramethyl-1,3,2-dioxaborolan-2-yl)phenyl]-1,4-dihydro[1,8]naphthyridin-4-one-3-carboxamide, the N-Cyclopropyl-1-[3-(5-methylsulfonylpyridin-3-yl)]phenyl]-1,4-dihydro[1,8]naphthyridin-4-one-3-carboxamide compound was obtained as a solid.

$^1$H NMR (CDCl$_3$) δ 0.71 (m, 2H), 0.90 (m, 2H), 3.03 (m, 1H), 3.21 (s, 3H), 7.53 (m, 1H), 7.60 (d, 1H), 7.74 (s, 1H), 7.80 (t, 1H), 7.86 (d, 1H), 8.45 (m, 1H), 8.74 (m, 1H), 8.86 (d, 1H), 9.09 (s, 1H), 9.20 (d, 2H), 9.78 (br, NH).

Example 33

N-Cyclopropyl-1-{3-[((1-hydroxy-1-methylethyl)-1-oxidopyridin-2-yl]phenyl}-1,4-dihydro[1,8]naphthyridin-4-one-3-carboxamide

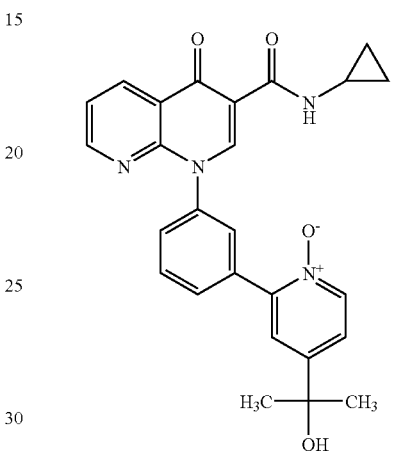

Step 1: Methyl 2-bromoisonicotinate

To a solution of 2-bromoisonicotinic acid (*Chem. Pharm. Bull.*, 38:2446(1990)) (2.0 g) in tetrahydrofuran (100 ml) was added excess ethereal diazomethane and the resulting mixture was stirred at room temperature for 1 hour. The mixture was evaporated and the product chromatographed on silica gel eluting with a 1:3 mixture of ethyl acetate and hexane to afford the Methyl 2-bromoisonicotinate ester as a colorless liquid.

Step 2: 2-Bromo-4-(1-hydroxy-1-methylethyl)pyridine

Following the procedure of Step 1 of Example 25, but substituting methyl 2-bromoisonicotinate from Step 1 for ethyl 5-bromonicotinate, the 2-Bromo-4-(1-hydroxy-1-methylethyl)pyridine compound was obtained as a white solid.

Step 3: 2-Bromo-4-(1-hydroxy-1-methylethyl)pyridine-N-oxide

Following the procedure of Step 2 of Example 30 but substituting 2-bromo-4-(1-hydroxy-1-methylethyl)pyridine from Step 2 for 5-bromo-2-(1-hydroxy-1-methylethyl)pyridine the 2-Bromo-4-(1-hydroxy-1-methylethyl)pyridine-N-oxide compound was obtained as a white solid.

Step 4: N-Cyclopropyl-1-{3-[4-(1-hydroxy-1-methylethyl)-1-oxidopyridin-2-yl]phenyl}-1,4-dihydro[1,8]naphthyridin-4-one-3-carboxamide Following the procedure of Step 3 of Example 32, but substituting 2-bromo-4-(1-hydroxy-1-methylethyl)pyridine- N-oxide from Step 3 for 3-bromo-5-methylsulfonylpyridine, the N-Cyclopropyl-1-{3-[4-(1-hydroxy-1-methylethyl)-1-oxidopyridin-2-yl]phenyl}-1,4-dihydro[1,8]naphthyridinone-3-carboxamide compound was obtained as a beige solid.

$^1$H NMR (DMSO-d$_6$) δ 0.57 (m, 2H), 0.79 (m, 2H), 1.45 (s, 6H), 2.90 (m, 1H), 5.35 (s, 1H, OH), 7.48 (m, 1H), 7.64 (m, 1H), 7.72 (m, 3H), 8.11 (m, 2H), 8.30 (d, 1H), 8.72 (dd, 1H), 8.78 (m, 1H), 8.82 (s, 1H), 9.72 (br, NH).

Example 34

N-Cyclopropyl-1-{3-[5-(1-hydroxy-1-methylethyl)pyridin-2-yl]phenyl}1,4-dihydro[1,8]naphthyridin-4-one-3-carboxamide

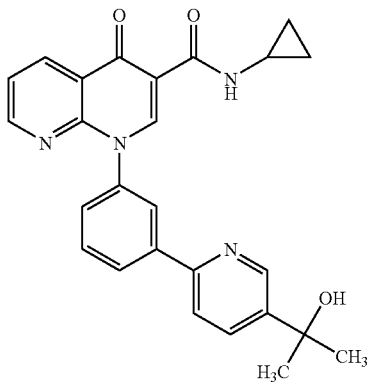

Step 1:
2-Bromo-5-(1-hydroxy-1-methylethyl)pyridine

A solution of 2,5-dibromopyridine in diethyl ether (5 ml/mmol) was cooled to −78° C., and n-butyllithium 2.5M in hexanes (1.05 eq) was added slowly. After 2 h in the cold, acetone (1.3 eq) was added and stirring was continued for 1 hour. The resulting mixture was quenched with saturated aqueous ammonium chloride solution, warmed to room temperature, and partitioned between ether and water. The crude product from the organic phase was triturated with 1:1 ether-hexane and filtered to afford the 2-Bromo-5-(1-hydroxy-1-methylethyl)pyridine compound as a solid.

Step 2: N-Cyclopropyl-1-{3-[5-(1-hydroxy-1-methylethyl)pyridin-2-yl]phenyl}-1,4-dihydro[1,8]naphthyridin-4-one-3-carboxamide Following the procedure of Step 3 of Example 32, but substituting 2-bromo-5-(1-hydroxy-1-methylethyl)pyridine from Step 1 for 3-bromo-5-methylsulfonylpyridine, the N-Cyclopropyl-1-{3-[5-(1-hydroxy-1-methylethyl)pyridin-2-yl]phenyl}-1,4-dihydro[1,8]naphthyridin-4-one-3-carboxamide compound was obtained as a solid.

$^1$H NMR (CDCl$_3$) δ 0.71 (m, 2H), 0.90 (m, 2H), 1.68 (s, 6H), 1.85 (s, 1H, OH), 3.04 (m, 1H), 7.45-7.52 (m, 2H), 7.71 (t, 1H), 7.79 (d, 1H), 7.95 (dd, 1H), 8.16 (s, 1H), 8.20 (d, 1H), 8.72 (m, 1H), 8.80-8.87 (m, 2H), 9.12 (s, 1H), 9.82 (br, NH).

Example 35

N-Cyclopropyl-1-{3-[3-(1-hydroxy-1-methylethyl)pyridin-4-yl]phenyl}-1,4-dihydro[1,8]naphthyridin-4-one-3-carboxamide

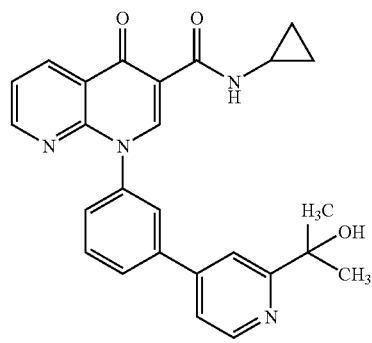

Step 1:
4-Bromo-2-(1-hydroxy-1-methylethyl)pyridine

Following the sequence described in Steps 1-2 of Example 33, but substituting 4-bromopicolinic acid (*Aust. J. Chem.* 24:390(1971)) for 2-bromoisonicotinic acid in Step 1, the 4-Bromo-2-(1-hydroxy-1-methylethyl)pyridine compound was obtained as a white solid.

Step 2: N-Cyclopropyl-1-{3-[3-(1-hydroxy-1-methylethyl)pyridin-4-yl]phenyl}-1,4-dihydro[1,8]naphthyridin-4-one-3-carboxamide Following the procedure of Step 3 of Example 32, but substituting 4-bromo-2-(1-hydroxy-1-methylethyl)pyridine from Step 1 for 3-bromo-5-methylsulfonylpyridine, the N-Cyclopropyl-1-{3-[3-(1-hydroxy-1-methylethyl)pyridin-4-yl]phenyl}-1,4-dihydro[1,8]naphthyridin-4-one-3-carboxamide compound was obtained as a beige solid.

$^1$H NMR (DMSO-d$_6$) δ 0.57 (m, 2H), 0.78 (m, 2H), 1.48 (s, 6H), 2.91 (m, 1H), 5.27 (s, 1H, OH), 7.62-7.66 (m, 2H), 7.72 7.79 (m, 2H), 8.01 (m, 1H), 8.10 (s, 1H), 8.58 (d, 1H), 8.73-8.79 (m, 2H), 8.84 (s, 1H), 9.73 (br, NH).

Example 36

Synthesis of N-Cyclopropyl-1-{3-[3-(1-hydroxy-1-methylethyl)-1-oxidopyridin-4-yl]phenyl}-1,4-dihydro[1,8]naphthyridin-4-one-3-carboxamide

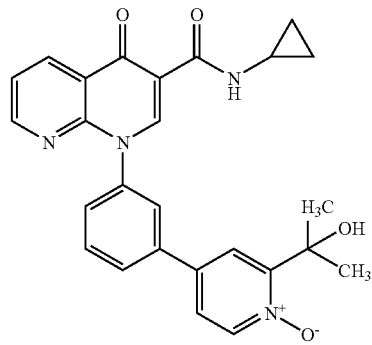

Step 1:
4-Bromo-2-(1-hydroxy-1-methylethyl)pyridine N-oxide

Following the procedure of Step 2 of Example 30, but substituting 4-bromo-2-(1-hydroxy-1-methylethyl)pyridine from Step 1 of Example 35 for 5-bromo-2-(1-hydroxy-1-methylethyl)pyridine, the 4-Bromo-2-(1-hydroxy-1-methylethyl)pyridine N-oxide compound was obtained as a white solid.

Step 2: N-Cyclopropyl-1-{3-[3-(1-hydroxy-1-methylethyl)-1-oxidopyridin-4-yl]phenyl}-1,4-dihydro[1,8]naphthyridin-4-one-3-carboxamide Following the procedure of Step 3 of Example 32, but substituting 4-bromo-2-(1-hydroxy-1-methylethyl)pyridine-N-oxide from Step 1 for 3-bromo-5-methylsulfonylpyridine, the N-Cyclopropyl-1-{3-[3-(1-hydroxy-1-methylethyl)-1-oxidopyridin-4-yl]phenyl}-1,4-dihydro[1,8]naphthyridin-4-one-3-carboxamide compound was obtained as a beige solid.

$^1$H NMR (DMSO-$d_6$) δ 0.57 (m, 2H), 0.78 (m, 2H), 1.62 (s, 6H), 2.90 (m, 1H), 6.99 (s, 1H, OH), 7.65-7.84 (m, 4H), 7.94 (s, 1H), 8.03 (dd, 1H), 8.15 (s, 1H), 8.38 (d, 1H), 8.73-8.78 (m, 2H), 8.83 (s, 1H), 9.73 (br, NH).

Example 37

N-Cyclopropyl-1-[3-(6-isopropylsulfonylpyridin-3-yl)]phenyl-1,4-dihydro[1,8]naphthyridin-4-one-3-carboxamide

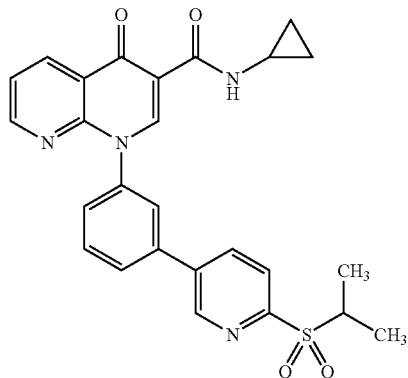

Step 1: 5-Bromo-2-isopropylthiopyridine

To a mixture of 2,5-dibromopyridine (2.07 g, 8.73 mmol) and 2-propanethiol (0.97 ml, 10.4 mmol) in N,N-dimethylformamide (20 ml) at 0° C. was added portionwise sodium hydride 60% dispersed in oil (450 mg, 11.3 mmol). The resulting mixture was stirred at room temperature for 1 hour, then partitioned between ether and water. The crude product from the organic phase was chromatographed on silica gel eluting with 10% ethyl acetate in hexane to afford the 5-Bromo-2-isopropylthiopyridine compound as a solid.

Step 2: 5-Bromo-2-isopropylsulfonylpyridine

To a solution of 5-bromo-2-isopropylthiopyridine from Step 1 (2.03 g, 8.75 mmol) in tetrahydrofuran (50 ml) and methanol (25 ml) at 0° C. was added oxone (15.8 g, 25.8 mmol) and then saturated aqueous sodium bicarbonate (25 ml). The resulting mixture was stirred at room temperature for 6 hours. The mixture was quenched with aqueous sodium bicarbonate and partitioned between ethyl acetate and water. The crude product from the organic phase was chromatographed on silica gel eluting with 20% ethyl acetate in hexane to afford the 5-Bromo-2-isopropylsulfonylpyridine compound as a white solid.

Step 3: N-Cyclopropyl-1-[3-(6-isopropylsulfonylpyridin-3-yl)]phenyl]-1,4-dihydro[1,8]naphthyridin-4-one-3-carboxamide Following the procedure of Step 3 of Example 32, but substituting 5-bromo-2-isopropylsulfonylpyridine from Step 2 for 3-bromo-5-methylsulfonylpyridine, the N-Cyclopropyl-1-[3-(6-isopropylsulfonylpyridin-3-yl)]phenyl]-1,4-dihydro[1,8]naphthyridin-4-one-3-carboxamide compound was obtained as a solid.

$^1$H NMR (CDCl$_3$) δ0.70 (m, 2H), 0.89 (m, 2H), 1.39 (d, 6H), 3.00 (m; 1H), 3.82 (m, 1H), 7.51 (m, 1H), 7.60 (d, 1H), 7.72 (s, 1H), 7.80 (t, 1H), 7.83 (d, 1H), 8.15-8.24 (m, 2H), 8.72 (m, 1H), 8.86 (dd, 1H), 9.03 (s, 1H), 9.10 (s, 1H), 9.77 (br, NH).

Example 38

N-Cyclopropyl-1-[3-(6-methoxypyridin-3-yl)phenyl]-1,4-dihydro[1,8]naphthyridin-4-one-3-carboxamide

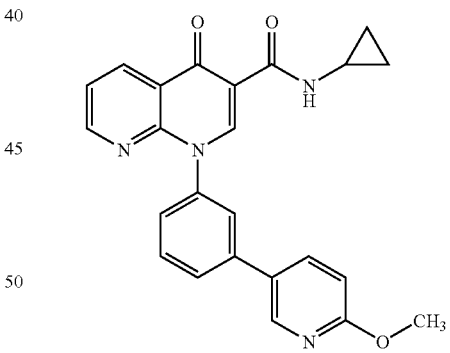

Step 1: 5-Bromo-2-methoxypyridine

To a solution of 2,5-dibromopyridine (6.95 g, 29 mmol) in N,N-dimethylformamide (5 ml) was added methanol (3.56 ml) and 1M potassium tert-butoxide (32.3 ml) and the resulting mixture was stirred at room temperature for 18 hours. The resulting slurry was quenched with saturated aqueous ammonium chloride solution and partitioned between ethyl acetate and water. The crude product from the organic phase was chromatographed on silica gel eluting with a 1:9 mixture of ether and hexane to afford the 5-Bromo-2-methoxypyridine compound as an oil.

Step 2: N-Cyclopropyl-1-[3-(6-methoxypyridin-3-yl)phenyl]-1,4-dihydro[1,8]naphthyridin-4-one-3-carboxamide Following the procedure of Step 3 of Example 32, but substituting 5-bromo-2-methoxypyridine from Step 1 for 3-bromo-5-methylsulfonylpyridine, the N-cyclopropyl-1-[3-(6-methoxypyridin-3-yl)phenyl]-1,4-dihydro[1,8]naphthyridin-4-one-3-carboxamide compound was obtained as a solid.

$^1$H NMR (CDCl$_3$) δ 0.71 (m, 2H), 0.89 (m, 2H), 3.00 (m, 1H), 4.00 (s, 3H), 6.85 (d, 1H), 7.44 (d, 1H), 7.50 (m, 1H), 7.62 (s, 1H), 7.68 (t, 1H), 7.73 (d, 1H), 7.83 (dd, 1H), 8.44 (s, 1H), 8.73 (m, 1H), 8.85 (dd, 1H), 9.10 (s, 1H), 9.82 (br, NH).

Example 39

N-Cyclopropyl-1-[3-(6-methylpyridin-3-yl)phenyl]-1,4-dihydro[1,8]naphthyridin-4-one-3-carboxamide

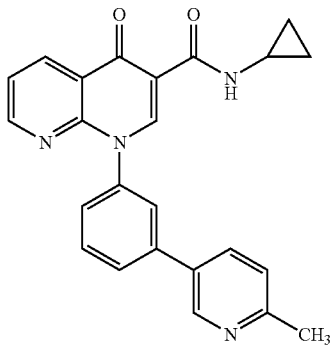

Following the procedure of Step 3 of Example 32, but substituting 5-bromo-2-methylpyridine from Step 1 of Example 28 for 3-bromo-5-methylsulfonylpyridine, the title compound was obtained as a solid.

$^1$H NMR (CDCl$_3$) δ 0.72 (m, 2H), 0.90 (m, 2H), 2.65 (s, 3H), 3.03 (m, 1H), 7.28 (d, 1H), 7.45-7.53 (m, 2H), 7.66 (s, 1H), 7.72 (t, 1H), 7.80 (d, 1H), 7.84 (dd, 1H), 8.73 (m, 1H), 8.80 (s, 1H), 8.86 (dd, 1H); 9.11 (s, 1H), 9.82 (br, NH).

Example 40

N-Cyclopropyl-1-{3-[6-(2,2,2-trifluoroethoxy)pyridin-3-yl]phenyl}-1,4-dihydro[1,8]naphthyridin-4-one-3-carboxamide

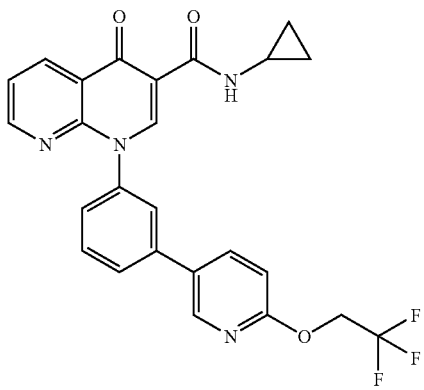

Step 1: 5-Bromo-2-(2,2,2-trifluoroethoxypyridine

Following the procedure of Step 1 of Example 38, but substituting 2,2,2-trifluoroethanol for methanol, with heating at 70° C. for 18 hours, the 5-Bromo-2-(2,2,2-trifluoroethoxy)pyridine compound was obtained as an oil.

Step 2: N-Cyclopropyl-1-{3-[6-(2,2,2-trifluoroethoxy)pyridin-3-yl]phenyl}-1,4-dihydro[1,8]naphthyridin-4-one-3-carboxamide Following the procedure of Step 3 of Example 32, but substituting 5-bromo-2-(2,2,2-trifluoroethoxy)pyridine from Step 1 for 3-bromo-5-methylsulfonylpyridine, the N-Cyclopropyl-1-{3-[6-(2,2,2-trifluoroethoxy)pyridin-3-yl]phenyl}-1,4-dihydro[1,8]naphthyridin-4-one-3-carboxamide compound was obtained as a solid.

$^1$H NMR (CDCl$_3$) δ 0.72 (m, 2H), 0.90 (m, 2H), 3.03 (m, 1H), 4.85 (q, 2H), 7.00 (d, 1H), 7.43-7.53 (m, 2H), 7.62 (s, 1H), 7.69-7.78 (m, 2H), 7.92 (dd, 1H), 8.42 (s, 1H), 8.73 (m, 1H), 8.85 (dd, 1H), 9.10 (s, 1H), 9.80 (br, NH).

Example 41

N-Cyclopropyl-1-[3-(5-bromopyridin-3-yl)phenyl]-1,4-dihydro[1,8]naphthyridin-4-one-3-carboxamide

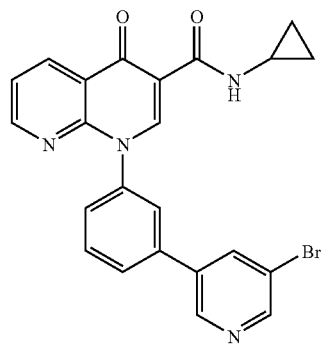

Following the procedure of Step 3 of Example 32, but substituting 3,5-dibromopyridine for 3-bromo-5-methylsulfonylpyridine, the title compound was obtained as a white solid.

$^1$H NMR (DMSO-d$_6$) δ 0.58 (m, 2H), 0.79 (m, 21), 2.90 (m, 1 µl), 7.65 (m, 1H), 7.71-7.77 (m, 2H), 8.03 (d, 1H), 8.14 (s, 1H), 8.49 (s, 1H), 8.74 (brs, 1H), 8.79 (brs, 1H), 8.86 (s, 1H), 9.01 (s, 1H), 9.73 (br, NH).

Example 42

N-Cyclopropyl-1-[3-(6-benzyloxypyridin-3-yl)phenyl]-1,4-dihydro[1,8]naphthyridin-4-one-3-carboxamide

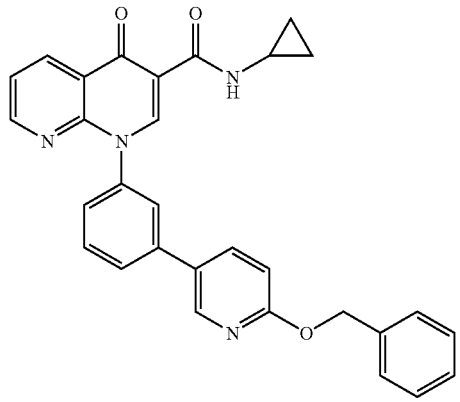

Step 1: 2-Benzyloxy-5-bromopyridine

A mixture of 2,5-dibromopyridine, benzyl alcohol (1.3 eq), potassium hydroxide pellets (2.4 eq) and dibenzo-18-crown-6 (0.05 eq) in toluene (4 ml/mmol) was refluxed with azeotropic removal of water for 3 hours. After evaporation of the toluene, the resulting mixture was partitioned between chloroform and water. The crude product from the organic phase was recrystallized from ether-hexane to afford the 2-Benzyloxy-5-bromopyridine compound as a solid.

Step 2: N-Cyclopropyl-1-[3-(6-benzyloxypyridin-3-yl)phenyl]-1,4-dihydro[1,4]naphthyridin-4-one-3-carboxamide Following the procedure of Step 3 of Example 32, but substituting 2-benzyloxy-5-bromopyridine from Step 1 for 3-bromo-5-methylsulfonylpyridine, the N-Cyclopropyl-1-[3-(6-benzyloxypyridin-3-yl)phenyl]-1,4-dihydro[1,8]naphthyridin-4-one-3-carboxamide compound was obtained as a white solid.

$^1$H NMR (DMSO-$d_6$) δ 0.57 (m, 2H), 0.79 (m, 2H), 2.91 (m, 1H), 5.42 (s, 2H) 7.00 (d, 1H), 7.32-7.48 (m, 5H), 7.61-7.72 (m, 3H), 7.90 (d, 1H), 7.99 (s, 1H), 8.14 (d, 1H), 8.59 (s, 1H), 8.73-8.84 (m, 3H), 9.73 (br, NH).

Example 43

N-Cyclopropyl-1-{3-[6-dicyclopropyl(hydroxy)methyl-1-oxidopyridin-3-yl]phenyl}-1,4-dihydro[1,8]naphthyridin-4-one-3-carboxamide

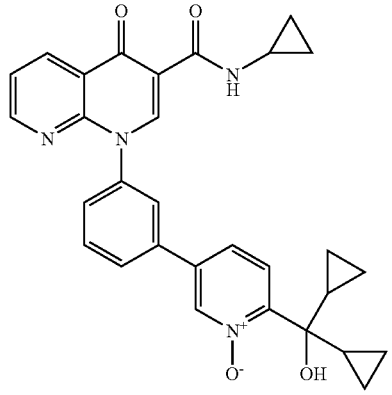

Step 1: 5-Bromo-2-dicyclopropyl)hydroxy)methylpyridine N-oxide

Following the procedure of Steps 1 and 2 of Example 30, but substituting dicyclopropyl ketone for acetone in Step 1, the 5-Bromo-2-dicyclopropyl(hydroxy)methylpyridine N-oxide compound was obtained as a solid.

Step 2: N-Cyclopropyl-1-{3-[6-dicyclopropyl(hydroxy)methyl-1-oxidopyridin-3-yl]phenyl}-1,4-dihydro[1,8]naphthyridin-4-one-3-carboxamide Following the procedure of Step 3 of Example 32, but substituting 5-bromo-2-dicyclopropyl(hydroxy)methylpyridine N-oxide from Step 1 for 3-bromo-5-methylsulfonylpyridine, the N-Cyclopropyl-1-{3-[6-dicyclopropyl(hydroxy)methyl-1-oxidopyridin-3-yl]phenyl}-1,4-dihydro[1,8]naphthyridin-4-one-3-carboxamide compound was obtained as a white solid.

$^1$H NMR (CDCl$_3$) δ 0.52 (m, 4H), 0.70 (m, 4H), 0.76 (m, 2H), 0.89 (m, 2H), 1.35 (m, 2H), 3.02 (m, 1H), 7.52 (m, 1H), 7.58 (m, 1H), 7.62 (dd, 1H), 7.68 (s, 1H), 7.73-7.80 (m, 3H), 8.15 (br, 1H, OH), 8.49 (s, 1H), 8.72 (m, 1H), 8.85 (dd, 1H), 9.09 (s, 1H), 9.78 (br, NH).

Example 44

N-Cyclopropyl-1-{3-[5-(1-hydroxy-1-methylethyl)-1-oxidopyridin-2-yl]phenyl}-1,4-dihydro[1,8]naphthyridin-4-one-3-carboxamide

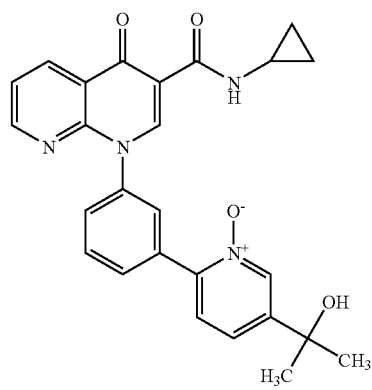

Step 1: 2-Bromo-5-(1-hydroxy-1-methylethyl)pyridine N-oxide

Following the procedure of Step 2 of Example 30, but substituting 2-bromo-5-(1-hydroxy-1-methylethyl)pyridine from Step 1 of Example 34 for 5-bromo-2-(1-hydroxy-1-methylethyl)pyridine, the 2-Bromo-5-(1-hydroxy-1-methylethyl)pyridine N-oxide compound was obtained as a white solid.

Step 2: N-Cyclopropyl-1-{3-[5-(1-hydroxy-1-methylethyl)-1-oxidopyridin-2-yl]phenyl}-1,4-dihydro[1,8]naphthyridin-4-one-3-carboxamide Following the procedure of Step 3 of Example 32, but substituting 2-bromo-5-(1-hydroxy-1-methylethyl)pyridine N-oxide from Step 1 for 3-bromo-5-methylsulfonylpyridine, the N-Cyclopropyl-1-{3-[5-(1-hydroxy-1-methylethyl)-1-oxidopyridin-2-yl]phenyl}-1,4-dihydro[1,8]naphthyridin-4-one-3-carboxamide compound was obtained as a solid.

$^1$H NMR (CDCl$_3$) δ 0.69 (m, 2H), 0.88 (m, 2H), 1.63 (s, 6H), 2.20 (s, 1H, OH), 2.98 (m, 1H), 7.38-7.49 (m, 3H), 7.52 (d, 1H), 7.70 (t, 1H), 7.98-8.04 (m, 2H), 8.50 (s, 1H), 8.69 (m, 1H), 8.80 (dd, 1H), 9.08 (s, 1H), 9.75 (br, NH).

Example 45

N-Cyclopropyl-1-{3-[6-(1-hydroxy-1-methylethyl)pyridin-3-yl]phenyl}-1,4-dihydro[1,8]naphthyridin-4-one-3-carboxamide

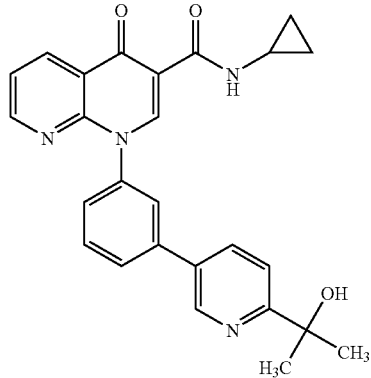

Following the procedure of Step 3 of Example 32, but substituting 5-bromo-2-(1-hydroxy-1-methylethyl)pyridine from Step 1 of Example 30 for 3-bromo-5-methylsulfonylpyridine, the title compound was obtained as a solid.

$^1$H NMR (CDCl$_3$) δ 0.72 (m, 2H), 090 (m, 2H), 1.62 (s, 6H), 3.02 (m, 1H), 4.85 (s, 1H, OH), 7.48-7.53 (m, 3H), 7.68 (s, 1H), 7.73 (t, 1H), 7.80 (d, 1H), 7.95 (dd, 1H), 8.72 (m, 1H), 8.81 (s, 1H), 8.86 (dd, 1H), 9.10 (s, 1H), 9.78 (br, NH).

Example 46

N-Isobutyl-1-{3-[6-(1-hydroxy-1-methylethyl)pyridin-3-yl]phenyl}-1,4-dihydro[1,8]naphthyridin-4-one-3-carboxamide

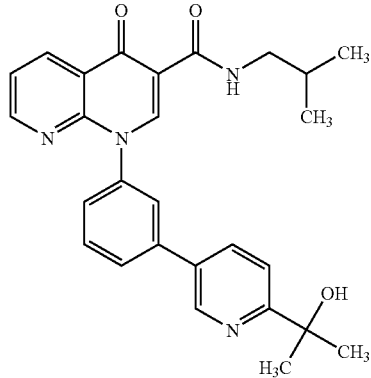

Step 1: 5-(3-Aminophenyl)-2-(1-hydroxy-1-methylethyl)pyridine

Following the procedure of Step 5 of Example 1, but substituting 3-aminophenylboronic acid for 3-acetyl phenylboronic acid and 5-bromo-2-(1-hydroxy-1-methylethyl)pyridine from Step 1 of Example 30 for N-isopropyl-1-(3-bromophenyl)-1,4-dihydro[1,8]naphthyridin-4-one-3-carboxamide, the 5-(3-Aminophenyl)-2-(1-hydroxy-1-methylethyl)pyridine compound was obtained as a solid.

Step 2: 1-{3-[6-(1-Hydroxy-1-methylethyl)pyridin-3-yl]phenyl}-1,4-dihydro[1,8]naphthyridin-4-one-3-carboxylic acid Following the procedures of Steps 1-3 of Example 1, but substituting 5-(3-aminophenyl)-2-(1-hydroxy-1-methylethyl)pyridine for 3-bromoaniline from Step 1 in the First Step, the 1-{3-[6-(1-Hydroxy-1-methylethyl)pyridin-3-yl]phenyl}-1,4-dihydro[1,8]naphthyridin-4-one-3-carboxylic acid compound was obtained as a solid.

Step 3: N-Isobutyl-1-{3-[6-(1-hydroxy-1-methylethyl)pyridin-3-yl]phenyl}-1,4-dihydro[1,8]naphthyridinone-3-carboxamide Following the procedure of Step 4 of Example 1, but substituting the acid from Step 2 for 1-(3-bromophenyl)-1,4-dihydro[1,8]naphthyridin-4-one-3-carboxylic acid, and isobutylamine for isopropylamine, the N-Isobutyl-1-{3-[6-(1-hydroxy-1-methylethyl)pyridin-3-yl]phenyl}-1,4-dihydro[1,8]naphthyridin-4-one-3-carboxamide compound was obtained as a cream-colored solid.

$^1$H NMR (Acetone-d$_6$) δ 0.98 (d, 6H), 1.53 (s, 6H), 1.88 (m, 1H), 3.26 (t, 2H), 4.66 (s, 1H, OH), 7.60 (m, 1H)., 7.69 (d, 1H), 7.76-7.79 (m, 2H), 7.95 (d, 1H), 8.05 (s, 1H), 8.16 (dd, 1H), 8.73 (m, 1H), 8.79 (dd, 1H), 8.90 (s, 1H), 8.94 (s, 1H), 9.83 (br, NH).

Example 47

N-Cyclopropyl-1-{5-bromo-3-[6-(1-hydroxy-1-methylethyl)pyridin-3-yl]phenyl}-1,4-dihydro[1,8]naphthyridin-4-one-3-carboxamide

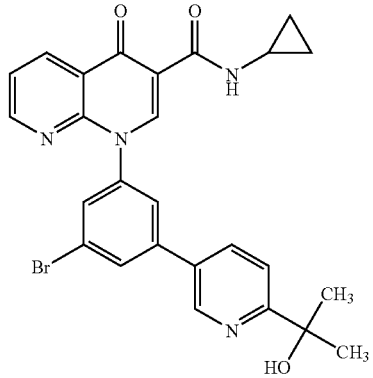

Step 1: 1-(3,5-Dibromophenyl)-1,4-dihydro[1,8]naphthyridin-4-one-3-carboxylic acid Following the procedures of Steps 1-3 of Example 1, but substituting 3,5-dibromoaniline for 3-bromoaniline in Step 1, the 1-(3,5-Dibromophenyl)-1,4-dihydro[1,8]naphthyridin-4-one-3-carboxylic acid compound was obtained as a beige solid.

Step 2: N-Cyclopropyl-1-(3,5-dibromophenyl)-1,4-dihydro[1,8]naphthyridin-4-one-3-carboxamide Following the procedure of Step 4 of Example 1, but substituting the 1-(3,5-Dibromophenyl)-1,4-dihydro[1,8]naphthyridin-4-one-3-carboxylic acid from Step 1 for 1-(3-bromophenyl)-1,4-dihydro[1,8]naphthyridin-4-one-3-carboxylic acid, and cyclopropylamine for isopropylamine, the N-Cyclopropyl-1-(3,5-dibromophenyl)-1,4-dihydro[1,8]naphthyridinone-3-carboxamide compound was obtained as a solid.

Step 3: 2-(1-Hydroxy-1-methylethyl)-5-tributylstannylpyridine

To a suspension of 2,5-dibromopyridine in toluene (5 ml/mmol) at −78° C., was added n-butyllithium 2.5M in hexanes (1 eq) and the resulting mixture was stirred in the cold for 2.5 hours. Acetone (1 eq) was added, and the mixture was warmed to −50° C. and became a brown solution. After cooling down to −78° C., more n-butyllithium (1 eq) was added along with ether (2 ml/mmol). After stirring in the cold for a further hour, tributyltin chloride (1.1 eq) was added and the mixture was warmed to room temperature and stirred for 2 hours. The mixture was quenched with saturated aqueous ammonium chloride solution and partitioned between ethyl acetate and water. The crude product from the organic phase was chromatographed on silica gel eluting with a 1:9 mixture of ethyl acetate and hexane to afford the 2-(1-Hydroxy-1-methylethyl)-5-tributylstannylpyridine compound as a colorless liquid.

Step 4: N-Cyclopropyl-1-{5-bromo-3-[6-(1-hydroxy-1-methylethyl)pyridin-3-yl]phenyl}-1,4-dihydro[1,8]naphthyridinone-3-carboxamide A mixture of N-cyclopropyl-1-(3,5-dibromophenyl)-1,4-dihydro[1,8]naphthyridin-4-one-3-carboxamide from Step 2, 2-(1-hydroxy-1-methylethyl)-5-tributylstannylpyridine from Step 3 (1.4 eq), 1,1'-bis (diphenylphosphino)ferrocene] dichloropalladium(II) (0.05 eq), and cuprous iodide (0.05 eq) in N,N-dimethylformamide (15 ml/mmol) was stirred at 85° C. for 5 hours. After cooling the resulting mixture was partitioned between ethyl acetate and water. The crude product from the organic phase was chromatographed on silica gel eluting with a 1:6:3 mixture of ethanol, ethyl acetate and methylene chloride to afford the N-Cyclopropyl-1-{5-bromo-3-[6-(1-hydroxy-1-methylethyl)pyridin-3-yl]phenyl}-1,4-dihydro[1,8]naphthyridin-4-one-3-carboxamide compound as a solid.

$^1$H NMR (CDCl$_3$) δ 0.72 (m, 2H), 0.90 (m, 2H), 1.62 (s, 6), 3.02 (m, 1H), 4.76 (s, 1H, OH), 7.50-7.56 (m, 2H), 7.62 (s, 1H), 7.69 (s, 1H), 7.90-7.96 (m, 2H), 8.74 (m, 1H), 8.79 (s, 1H), 8.86 (dd, 1H), 9.07 (s, 1H), 9.74 (br, NH).

Example 48

N-Cyclopropyl-1-{3-[6-(1-hydroxy-1-methylethyl)pyridin-2-yl]phenyl}1-1,4-dihydro[1,8]naphthyridin-4-one-3-carboxamide

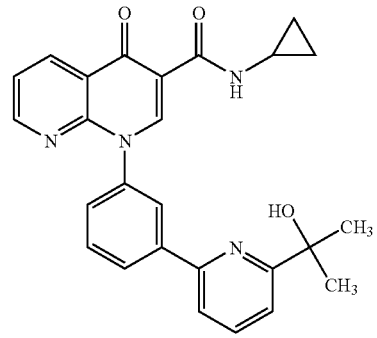

Step 1: 2-(1-Hydroxy-1-methylethyl)-6-tributylstannylpyridine

Following the procedure of Step 3 of Example 47, but substituting 2,6-dibromopyridine for 2,5-dibromopyridine, the 2-(1-Hydroxy-1-methylethyl)-6-tributylstannylpyridine compound was obtained.

Step 2: N-Cyclopropyl-1-{3-[6-(1-hydroxy-1-methylethyl)pyridin-2-yl]phenyl}-1,4-dihydro[1,8]naphthyridin-4-one-3-carboxamide Following the procedure of Step 4 of Example 47, but substituting 2-(1-hydroxy-1-methylethyl)-6 tributylstannyl pyridine from Step 1 for 2-(1-hydroxy-1-methylethyl)-5-tributylstannylpyridine, the N-Cyclopropyl-1-{3-[6-(1-hydroxy-1-methylethyl)pyridin-2-yl]phenyl}-1,4-dihydro[1,8]naphthyridinone-3-carboxamide compound was obtained as a solid.

$^1$H NMR (CDCl$_3$) δ 0.72 (m, 2H), 0.90 (m, 2H), 1.61 (s, 6H), 3.04 (m, 1H), 5.13 (s, 1H, OH), 7.40 (d, 1H), 7.46-7.53 (m, 2H), 7.70-7.76 (m, 2H), 7.85 (t, 1H), 8.13 (s, 1H), 8.22 (d, 1H), 8.73 (m, 1H), 8.87 (d, 1H), 9.12 (s, 1H), 9.83 (br, NH).

Example 49

N-Isopropyl-1-[3-(4-methylsulfonylphenyl)phenyl]-1,4-dihydro[1,8]naphthyridin-4-one-3-carboxamide

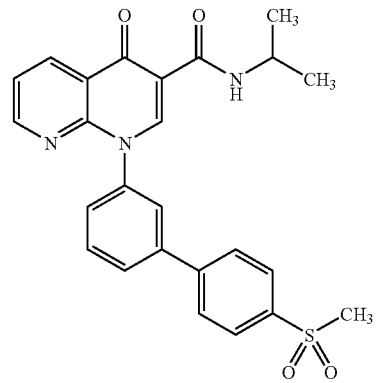

To a mixture of N-isopropyl-1-[3-(4-methylthiophenyl)phenyl]-1,4-dihydro[1,8]naphthyridin-4-one-3-carboxamide from Example 22 in tetrahydrofuran (24 ml/mmol), methanol (12 ml/mmol), and water (12 ml/mmol), was added oxone (2.24 eq) and the resulting mixture was stirred at room temperature for 2 hours. The mixture was quenched with saturated aqueous sodium bicarbonate and partitioned between ethyl acetate and water. The crude product from the organic phase was chromatographed on silica gel eluting with 30% ether in methylene chloride to afford the title compound as a white solid.

$^1$H NMR (Acetone-$d_6$) δ 1.25 (d, 6H), 3.16 (s, 3H), 4.18 (m, 1H), 7.60 (m, 1H), 7.74 (d, 1H), 7.79 (t, 1H), 7.99 (d, 1H), 8.05 (s, 4H), 8.09 (s, 1H), 8.72 (m, 1H), 8.78 (dd, 1H), 8.93 (s, 1H), 9.64 (br, NH).

Example 50

N-Cyclopropyl-1-[3-(6-methylsulfonylpyridin-3-yl)phenyl]-1,4-dihydro[1,8]naphthyridin-4-one-3-carboxamide

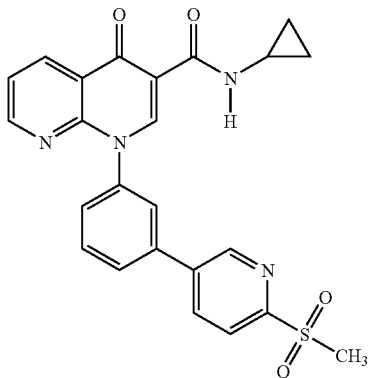

Step 1: 5-Bromo-2-methylthiopyridine

A mixture of 2,5-dibromopyridine and sodium thiomethoxide (1.3 eq) in N,N-dimethylformamide (2 ml/mmol) was stirred at room temperature for 20 minutes then cooled to 0° C. After diluting with cold water the precipitate was filtered to afford the 5-Bromo-2-methylthiopyridine compound as a solid.

Step 2: N-Cyclopropyl-1-[3-(6-methylthiopyridin-3-yl)phenyl]-1,4-dihydro[1,8]naphthyridin-4-one-3-carboxamide Following the procedure of Step 3 of Example 32, but substituting 5-bromo-2-methylthiopyridine from Step 1 for 3-bromo-5-methylsulfonylpyridine, the N-Cyclopropyl-1-[3-(6-methylthiopyridin-3-yl)phenyl]-1,4-dihydro[1,8]naphthyridin-4-one-3-carboxamide compound was obtained as a solid.

Step 3: N-Cyclopropyl-1-[3-(6-methylsulfonylpyridin-3-yl)phenyl]-1,4-dihydro[1,8]naphthyridin-4-one-3-carboxamide Following the procedure of Example 49, but substituting N-cyclopropyl-1-[3-(6-methylthiopyridin-3-yl)phenyl]-1,4-dihydro[1,8]naphthyridin-4-one-3-carboxamide from Step 2 for N-isopropyl-1-[3-(4-methylthiophenyl)phenyl]-1,4-dihydro[1,8]naphthyridin-4-one-3-carboxamide, the N-Cyclopropyl-1-[3-(6-methylsulfonylpyridin-3-yl)phenyl]-1,4-dihydro[1,8]naphthyridin-4-one-3-carboxamide compound was obtained as a solid.

$^1$H NMR (CDCl$_3$) δ 0.66 (m, 2H), 0.84 (m, 2H), 2.97 (m, 1H), 3.26 (s, 3H), 7.48 (m, 1H), 7.55 (d, 1H), 7.67 (s, 1H), 7.74-7.80 (m, 2H), 8.14-8.19 (m, 2H), 8.68 (m, 1H), 8.81 (dd, 1H), 8.96 (s, 1H), 9.05 (s, 1H), 9.73 (br, NH).

Example 51

N-Isopropyl-1-[3-(5-methylsulfonylpyridin-3-yl)phenyl]-1,4-dihydro[1,8]naphthyridin-4-one-3-carboxamide

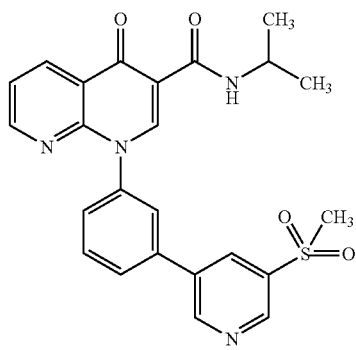

Following the procedure of Example 49, but substituting N-isopropyl-1-[3-(5-methylthiopyridin-3-yl)phenyl]-1,4-dihydro[1,8]naphthyridin-4-one-3-carboxamide from Example 15 for N-isopropyl-1-[3-(4-methylthiophenyl)phenyl]-1,4-dihydro[1,8]naphthyridin-4-one-3-carboxamide, the title compound was obtained as a solid.

$^1$H NMR (CDCl$_3$) δ 1.33 (d, 6H), 3.20 (s, 3H), 4.31 (m, 1H), 7.52 (m, 1H), 7.60 (d, 1H), 7.73 (s, 1H), 7.79 (t, 1H), 7.86 (d, 1H), 8.48 (m, 1H), 8.73 (m, 1H), 8.88 (d, 1H), 9.08 (s, 1H), 9.19 (d, 2H), 9.68 (br, NH).

Example 52

N-Cyclopropyl-1-[3-(4-ethylsulfonylphenyl)phenyl]-1,4-dihydro[1,8]naphthyridin-4-one-3-carboxamide

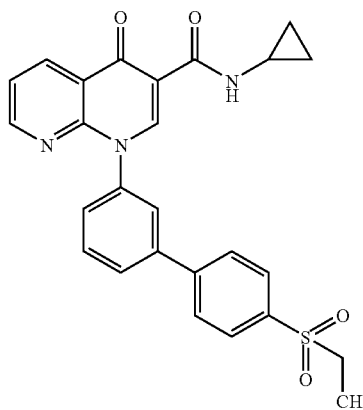

Following the procedure of Example 49, but substituting N-cyclopropyl-1-[3-(4-ethylthiophenyl)phenyl]-1,4-dihydro[1,8]naphthyridin-4-one-3-carboxamide from Example 18 for N-isopropyl-1-[3-(4-methylthiophenyl)phenyl]-1,4-dihydro[1,8]naphthyridin-4-one-3-carboxamide, the title compound was obtained as a solid.

$^1$H NMR (CDCl$_3$) δ 0.72 (m, 2H), 0.90 (m, 2H), 1.35 (t, 3H), 3.02 (m, 1H), 3.18 (q, 2H), 7.48-7.56 (m, 2H), 7.70 (s, 1H), 7.75 (t, 1H), 7.84 (m, 3H), 8.03 (d, 2H), 8.73 (m, 1H), 8.85 (dd, 1H), 9.10 (s, 1H), 9.80 (br, NH).

Example 53

N-Cyclopropyl-1-[3-(4-ethylsulfinylphenyl)phenyl]-1,4-dihydro[1,8]naphthyridin-4-one-3-carboxamide

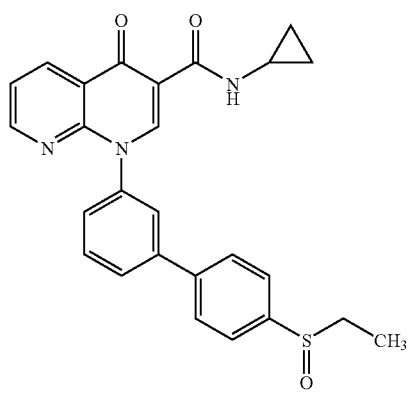

To a solution of N-cyclopropyl-1-[3-(4-ethylthiophenyl)phenyl]-1,4-dihydro[1,8]naphthyridinone-3-carboxamide from Example 18, in a 1:1 mixture of methylene chloride and methanol (9 ml/mmol), was added at 0° C. magnesium monoperoxyphthalate hexahydrate (MMPP, 0.5 molareq) and the resulting mixture was stirred in the cold for 2 hours. The mixture was quenched with saturated aqueous sodium bicarbonate and partitioned between methylene chloride and water. The crude product from the organic phase was chromatographed on silica gel eluting with a 90:9:1 mixture of methylene chloride, ethanol and 28% aqueous ammonium hydroxide to afford the title compound as a solid.

$^1$H NMR (CDCl$_3$) δ 0.68 (m, 2H), 0.85 (m, 2H), 1.15 (m, 3H), 2.80 (m, 1H), 2.94 (m, 1H), 2.98 (m, 1H), 7.45-7.50 (m, 2H), 7.65-7.73 (m, 4H), 7.76-7.82 (m, 3H), 8.71 (m, 1H), 8.83 (dd, 1H), 9.06 (s, 1H), 9.78 (br, NH).

Example 54

N-Isopropyl-1-{3-[4-(1-oximidoethyl)phenyl]phenyl}-1,4-dihydro[1,8]naphthyridin-2-one-3-carboxamide

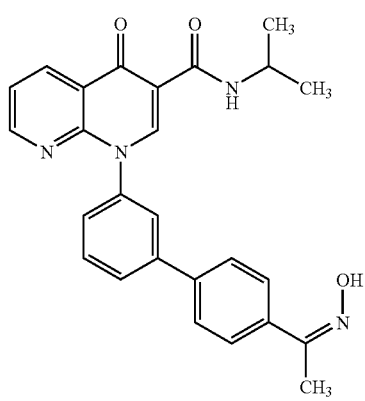

To a solution of N-isopropyl-1-[3-(4-acetylphenyl)phenyl]-1,4-dihydro[1,8]naphthyridin-4-one-3-carboxamide from Example 4 in pyridine (1 ml/mmol) at room temperature was added hydroxylamine hydrochloride (2.1 eq) and the resulting mixture was stirred for 16 hours. The mixture was filtered through celite and the filtrate evaporated. The residue was dissolved in ethyl acetate, washed with saturated aqueous sodium carbonate and then water, dried and evaporated. The residue was stirred in a small volume of acetone and filtered to afford the title compound as a solid.

$^1$H NMR (CDCl$_3$) δ 1.29 (d, 6H), 2.27 (s, 3H), 4.30 (m, 1H), 7.39 (d, 1H), 7.46 (m, 1H), 7.56 (d, 2H), 7.59-7.63 (m, 2H), 7.66 (d, 2H), 7.72 (d, 1H), 8.17 (s, 1H, OH), 8.69 (brs, 1H), 8.82 (d, 1H), 9.10 (s, 1H), 9.71 (br, NH).

Example 55

N-Isopropyl-1-{3-[4-(piperazin-1-yl)phenyl]-phenyl}-1,4-dihydro[1,8]naphthyridin-4-one-3-carboxamide

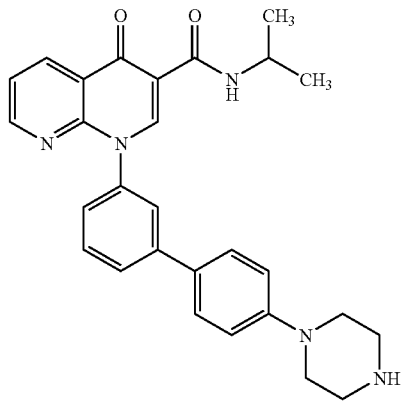

To a solution of N-isopropyl-1-{3-[4-(4-tertbutyloxycarbonylpiperazin-1-yl)phenyl]-phenyl}-1,4-dihydro[1,8] naphthyridin-4-one-3-carboxamide from Example 11 in methylene chloride (10 ml/mmol) was added trifluororacetic acid (6 ml/mmol) and the resulting mixture was stirred at room temperature for 2 hours, then warmed gently for 15 minutes. The mixture was evaporated and the crude product was chromatographed on silica gel eluting with a 9:0.9:0.1 mixture of methylene chloride, methanol and 28% aqueous ammonium hydroxide to afford the title compound as a solid.

$^1$H NMR (CDCl$_3$) δ 1.29 (d, 6H), 2.99 (m, 4H), 3.16 (m, 4H), 4.25 (m, 1H), 6.94 (d, 2H), 7.29 (d, 1H), 7.42 (m, 1H), 7.50 (d, 2H), 7.52-7.58 (m, 2H), 7.69 (d, 1H), 8.66 (m, 1H), 8.78 (dd, 1H), 9.04 (s, 1H), 9.69 (br, NH).

Example 56

N-Cyclopropyl-1-[3-(4-methylsulfonylmethylphenyl)phenyl]-1,4-dihydro[1,8]naphthyridin-4-one-3-carboxamide

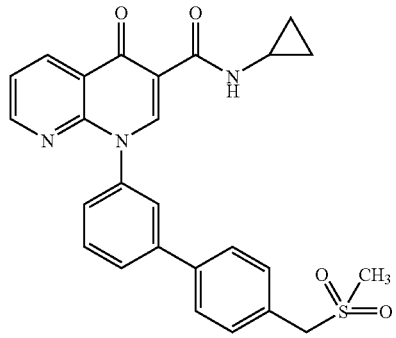

Step 1: N-Cyclopropyl-1-[3-(4-bromomethylphenyl)phenyl]-1,4-dihydro[1,8]naphthyridin-4-one-3-carboxamide A mixture of N-cyclopropyl-1-[3-(4-hydroxymethylphenyl)phenyl]-1,4-dihydro[1,8]naphthyridin-4-one-3-carboxamide from Example 16, carbon tetrabromide (2 eq), and diphos (0.6 molareq) in methylene chloride (15 ml/mmol) was stirred at room temperature for 3 hours. The mixture was concentrated at room temperature and chromatographed on silica gel eluting with a 1:1 mixture of ethyl acetate and methylene chloride to afford the N-Cyclopropyl-1-[3-(4-bromomethylphenyl)phenyl]-1,4-dihydro[1,8]naphthyridin-4-one-3-carboxamide compound.

Step 2: N-Cyclopropyl-1-[3-(4-methylsulfonylmethylphenyl)phenyl]-1,4-dihydro [1,8]naphthyridin-4-one-3-carboxamide To a solution of N-Cyclopropyl-1-[3-(4-bromomethylphenyl)phenyl]-1,4-dihydro[1,8]naphthyridin-4-one-3-carboxaride from Step 1 in N,N-dimethylformamide (20 ml/mmol) was added methanesulfinic acid sodium salt (1.3 eq) and the resulting mixture was stirred at room temperature for 18 hours. To the mixture was added saturated aqueous ammonium chloride solution and ethyl acetate, and the insoluble solid was filtered and washed well with water, hexane, ether and ethyl acetate to afford the title compound as a solid.

$^1$H NMR (CDCl$_3$) δ 0.72 (m, 2H), 0.89 (m, 2H), 2.85 (s, 3H), 3.04 (m, 1H), 4.34 (s, 2H) 7.46-7.52 (m, 2H), 7.55 (d, 21H), 7.65-7.73 (m, 4H), 7.80 (d, 1H), 8.76 (m, 1H), 8.85 (d, 1H), 9.12 (s, 1H), 9.82 (br, NH).

Example 57

N-Cyclopropyl-1-[3-(1,6-dihydro-6-oxopyridin-3-yl)phenyl]-1,4-dihydro[1,8]naphthyridin-4-one-3-carboxamide

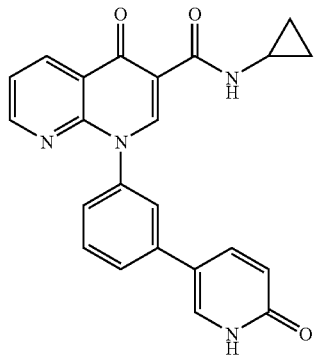

To a solution of N-cyclopropyl-1-[3-(6-benzyloxypyridin-3-yl)phenyl]-1,4-dihydro[1,8]naphthyridin-4-one-3-carboxamide from Example 42 in 1,2-dichloroethane (25 ml/mmol) was added trifluoroacetic acid (1.5 ml/mmol) and the resulting mixture was stirred at 60° C. for 18 hours. More trifluoroacetic acid was added (0.75 ml/mmol) and heating was continued for a further 24 hours. The cooled mixture was diluted with methylene chloride and saturated aqueous sodium bicarbonate was added, resulting in precipitation of a solid which was filtered. From the filtrate the organic phase was collected and evaporated to a solid which was combined with the previous filtered solid. This mixture was chromatographed on silica gel eluting with 10% methanol in methylene chloride to afford the title compound as a white fluffy solid.

$^1$H NMR (DMSO-d$_6$) δ 0.57 (m, 2H), 0.78 (m, 2H), 2.90 (m, 1H), 6.45 (d, 1H), 7.52 (m, 1H), 7.61-7.65 (m, 2H), 7.78 (d, 1H), 7.85 (s, 1H), 7.89-7.93 (m, 2H), 8.74 (d, 1H), 8.78-8.81 (m, 2H), 9.73 (br, NH), other NH>11 ppm.

Example 58

N-Cyclopropyl-1-[[3-{5-(6-(1-hydroxy-1-methylethyl)pyridin-3-yl]pyridin-3-yl}phenyl]]-1,4-dihydro[1,8]naphthyridin-4-one-3-carboxamide

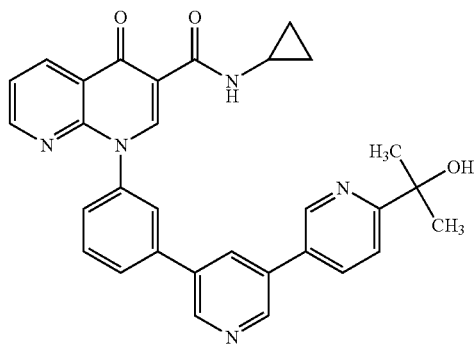

Following the procedure of Step 4 of Example 47, but substituting N-cyclopropyl-1-[3-(5-bromopyridin-3-yl)phenyl]-1,4-dihydro[1,8]naphthyridinone-3-carboxamide from Example 41 for N-cyclopropyl-1-(3,5-dibromophenyl)-1,4-dihydro[1,8]naphthyridin-4-one-3-carboxamide, the title compound was obtained as a white solid.

¹H NMR (DMSO-d₆) δ 0.58 (m, 2H), 0.79 (m, 2H), 2.91 (m, 1H), 5.30 (s, 1H, OH), 7.65 (m, 1H), 7.71-7.79 (m, 3H), 8.12 (d, 1H), 8.23-8.26 (m, 2H), 8.49 (s, 1H), 8.75 (dd, 1H), 8.80 (m, 1H), 8.87 (s, 1H), 8.97 (m, 2H), 9.04 (s, 1H), 9.74 (br, NH).

Example 59

N-Isopropyl-1-[3-(1-oxidopyridin-3-yl)phenyl]-1,4-dihydro[1,8]naphthyridin-4-one-3-carboxamide

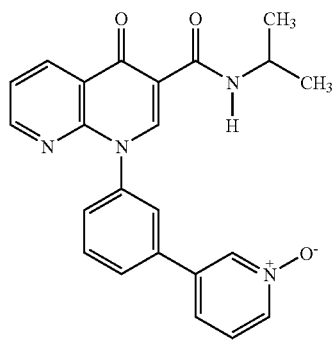

Following the procedure of Step 2 of Example 30, but substituting N-isopropyl-1-[3-(pyridin-3-yl)phenyl]-1,4-dihydro[1,8]naphthyridin-4-one-3-carboxamide from Example 7 for 5-bromo-2-(1-hydroxy-1-methylethyl)pyridine, the title compound was obtained as a white solid.

¹H NMR (DMSO-d₆) δ 1.21 (d, 6H), 4.10 (m, 1H), 7.51 (t, 1H), 7.64 (m, 1H), 7.71-7.75 (m, 3H), 7.97 (m, 1H), 8.09 (s, 1H), 8.23 (d, 1H), 8.69-8.77 (m, 3H), 8.84 (s, 1H), 9.66 (br, NH).

Example 60

N-(2,6-Dichloropyridin-4-yl)-1-[3-(1-oxidopyridin-3-yl)phenyl]-1,4-dihydro[1,8]naphthyridin-4-one-3-carboxamide

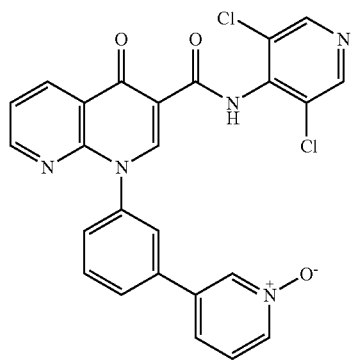

Following the procedure of Step 2 of Example 30, but substituting N-(2,6-dichloropyridin-4-yl)-1-[3-(pyridin-3-yl)phenyl]-1,4-dihydro[1,8]naphthyridin-4-one-3-carboxamide from Example 10 for 5-bromo-2-(1-hydroxy-1-methylethyl)pirydine, the title compound was obtained as a white solid.

¹H NMR (DMSO-d₆) δ 7.51 (m, 1H), 7.69-7.78 (m, 4H), 7.99 (dd, 1H), 8.14 (s, 1H), 8.24 (dd, 1H), 8.70 (s, 1H), 8.73 (s, 2H), 8.84 (m, 2H), 8.99 (s, 1H), 12.05 (br, NH).

Example 61

N-Isopropyl-1-[3-(5-carboethoxy-1-oxidopyridin-3-yl)phenyl]-1,4-dihydro[1,8]naphthyridin-4-one-3-carboxamide

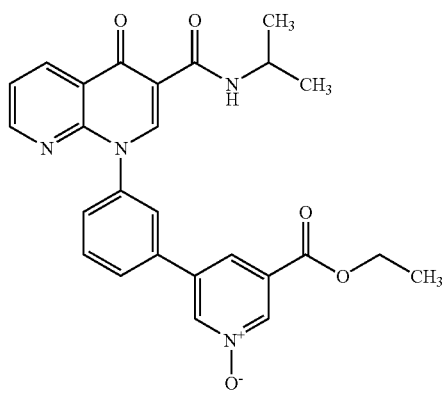

Following the procedure of Step 2 of Example 30, but substituting N-isopropyl-1-[3-(5-carboethoxypyridin-3-yl)phenyl]-1,4-dihydro[1,8]naphthyridinone-3-carboxamide from Example 24 for 5-bromo-2-(1-hydroxy-1-methylethyl)pyridine, the title compound was obtained as a white solid.

¹H NMR (CDCl₃) δ 1.28 (d, 6H), 1.40 (t, 3H), 4.28 (m, 1H), 4.43 (q, 2H), 7.49 (dd, 1H), 7.56 (m, 1H), 7.68 (s, 1H), 7.73 (d, 2H), 8.04 (s, 1H), 8.60 (s, 1H), 8.68 (dd, 1H), 8.77 (s, 1H), 8.82 (d, 1H), 9.01 (s, 1H), 9.61 (br, NH).

Example 62

N-Isopropyl-1-{3-[5-(1-hydroxy-1-methylethyl)-1-oxidopyridin-3-yl]phenyl}-1,4-dihydro[1,8]naphthyridin-4-one-3-carboxamide

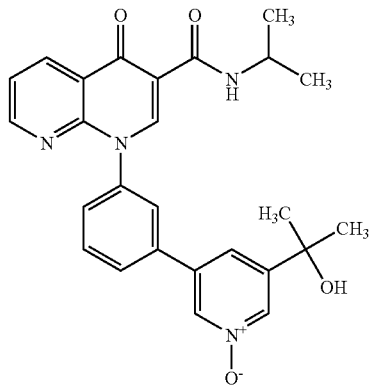

Following the procedure of Step 2 of Example 30, but substituting N-isopropyl-1-{3-[5-(1-hydroxy-1-methylethyl)pyridin-3-yl]phenyl}-1,4-dihydro[1,8]naphthyridin-4-one-3-carboxamide from Example 25 for 5-bromo-2-(1-hydroxy-1-methylethyl)pirydine, the title compound was obtained as a white solid $^1$HNMR (CDCl$_3$) δ 1.29 (d, 6H), 1.60 (s, 6H), 4.11 (brs, 1H), 4.23 (m, 1H), 7.42-7.51 (m, 2H), 7.58 (s, 2H) 7.65 (m, 2H), 8.28 (s, 1H), 8.33 (s, 1H), 8.64 (m, 1H), 8.80 (d, 1H), 8.98 (s, 1H), 9.61 (br, NH).

Example 63

N-Isopropyl-1-{3-[6-(2-methylpropyl)-1-oxidopyridin-3-yl]phenyl}-1,4-dihydro [1,8]naphthyridin-4-one-3-carboxamide

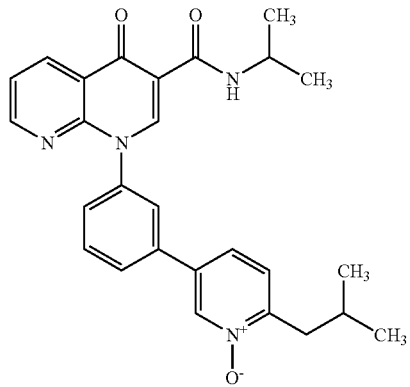

Following the procedure of Step 2 of Example 30, but substituting N-isopropyl-1-{3-[6-(2-methylpropyl)pyridin-3-yl]phenyl)-1,4-dihydro[1,8]naphthyridin-4-one-3-carboxamide from Example 26 for 5-bromo-2-(1-hydroxy-1-methylethyl)pirydine, the title compound was obtained as an off-white solid.

$^1$H NMR (CDCl$_3$) δ 0.98 (d, 6H), 1.29 (d, 6H), 2.29 (m, 1H), 2.32 (d, 2H), 4.26 (m, 1H), 7.28 (d, 1H), 7.38 (d, 1H), 7.47-7.52 (m, 2H), 7.60 (s, 1H), 7.69 (m, 2H), 8.53 (s, 1H), 8.69 (m, 1H), 8.82 (dd, 1H), 9.03 (s, 1H), 9.62 (br, NH).

Example 64

N-Isopropyl-1-[3-(6-methyl-1-oxidopyridin-3-yl)phenyl]-1,4-dihydro[1,8]naphthyridin-4-one-3-carboxamide

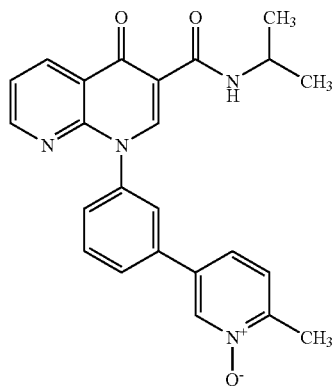

Following the procedure of Step 2 of Example 30, but substituting N-isopropyl-1-[3-(6-methylpyridin-3-yl)phenyl]-1,4-dihydro[1,8]naphthyridin-4-one-3-carboxamide from Example 28 for 5-bromo-2-(1-hydroxy-1-methylethyl)pirydine, the title compound was obtained as an off-white solid.

$^1$H NMR (CDCl$_3$) δ 1.32 (d, 6H), 2.60 (s, 3H), 4.30 (m, 1H), 7.35-7.45 (m, 2H), 7.50 (m, 2H), 7.62 (s, 1H), 7.72 (d, 2H), 8.58 (s, 1H), 8.72 (m, 1H), 8.85 (dd, 1H), 9.06 (s, 1H), 9.66 (br, NH).

Example 65

N-Cyclopropyl-1-[3-(1-oxidopyridin-3-yl)phenyl]-1,4-dihydro[1,8]naphthyridin-4-one-3-carboxamide

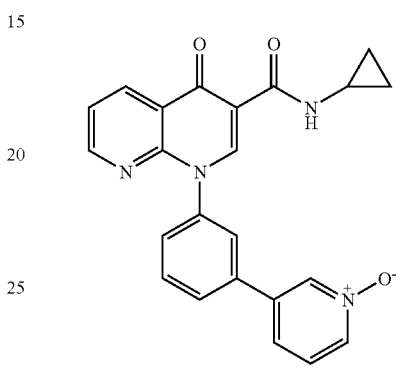

Following the procedure of Step 2 of Example 30, but substituting N-cyclopropyl-1-[3-(pyridin-3-yl)phenyl]-1,4dihydro[1,8]naphthyridin-4-one-3-carboxamide from Example 14 for 5-bromo-2-(1-hydroxy-1-methylethyl)pirydine, the title compound was obtained as a white solid.

$^1$H NMR (DMSO-d$_6$) δ 0.57 (m, 2H), 0.78 (m, 2H), 2.90 (m, 1H), 7.52 (t, 1H), 7.65 (m, 1H), 7.72-7.76 (m, 3H), 7.98 (m, 1H), 8.10 (s, 1H), 8.25 (d, 1H), 8.70-8.79 (m, 3H), 8.85 (s, 1H), 9.72 (br, NH).

Example 66

N-Cyclopropyl-1-{3-[6-(1-hydroxy-1-methylethyl)-1-oxidopyridin-3-yl]phenyl}-1,4-dihydro[1,8]naphthyridin-4-one-3-carboxamide

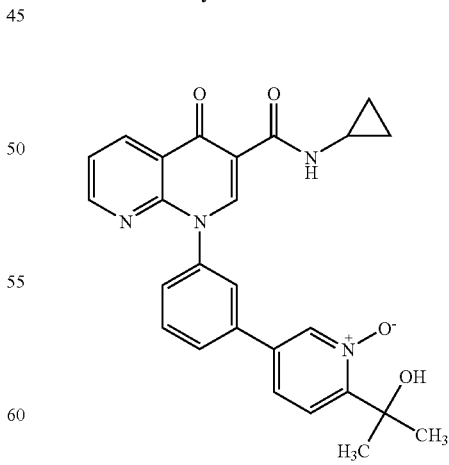

Following the procedure of Step 2 of Example 29 but substituting 5-bromo-2-(1-hydroxy-1-methylethyl)pirydine N-oxide from Step 2 of Example 30 for 5-bromo-1-oxidopyrimidine, the title compound was obtained as a white solid.

¹H NMR (CDCl₃) δ 0.66 (m, 2H), 0.85 (m, 2H), 1.70 (s, 6H), 2.97 (m, 1H), 7.43-7.49 (m, 2H), 7.52-7.56 (m, 2H), 7.61 (s, 2H) 7.71-7.74 (m, 2H), 8.49 (s, 1H), 8.68 (m, 1H), 8.80 (d, 1H), 9.02 (s, 1H), 9.74 (br, NH).

Example 67

N-Cyclopropyl-1-[3-(1-oxidopyridin-4-yl)phenyl]-1,4-dihydro[1,8]naphthyridin-4-one-3-carboxamide

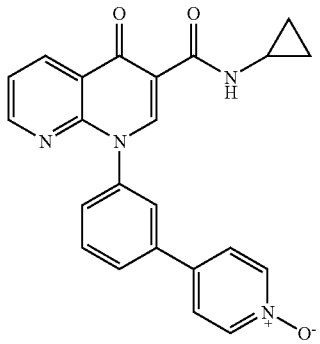

Following the procedure of Step 2 of Example 30, but substituting N-cyclopropyl-1-[3-(pyridin-4-yl)phenyl]-1,4-dihydro[1,8]naphthyridinone-3-carboxamide from Example 17 for 5-bromo-2-(1-hydroxy-1-methylethyl)pirydine, the title compound was obtained as a white solid.

¹H NMR (DMSO-d₆) δ 0.57 (m, 2H), 0.79 (m, 2H), 2.92 (m, 1H), 7.62-7.70 (m, 2H), 7.75 (t, 1H), 7.88 (d, 2H), 8.03 (d, 1H), 8.15 (s, 1H), 8.30 (d, 2H), 8.75 (d, 1H), 8.80 (m, 1H), 8.86 (s, 1H), 9.73 (br, NH).

Example 68

N-Cyclopropyl-1-[3-(5-bromo-1-oxidopyridin-3-yl)phenyl]-1-1,4-dihydro[1,8]naphthyridin-4-one-3-carboxamide

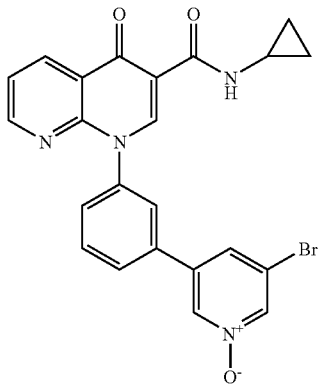

Following the procedure of Step 2 of Example 30, but substituting N-cyclopropyl-1-[3-(5-bromopyridin-3-yl)phenyl]-1,4-dihydro[1,8]naphthyridinone-3-carboxamide from Example 41 for 5-bromo-2-(1-hydroxy-1-methylethyl)pirydine, the title compound was obtained as a light yellow solid.

¹H NMR (DMSO-d₆) δ 0.56 (m, 2H), 0.78 (m, 2H), 2.91 (m, 1H), 7.65 (m, 1H), 7.71-7.74 (m, 2H), 8.02-8.06 (m, 2H), 8.15 (s, 1H), 8.60 (s, 1H), 8.73-8.79 (m, 3H), 8.86 (s, 1H), 9.73 (br, NH).

Example 69

N-Cyclopropyl-1-[[3-{5-[6-(1-hydroxy-1-methylethyl)-1-oxidopyridin-3-yl]pyridin-3-yl}phenyl]]-1,4-dihydro[1,8]naphthyridin-4-one-3-carboxamide

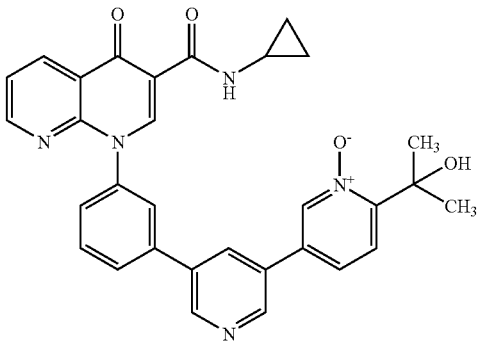

Following the procedure of Step 2 of Example 30, but substituting N-cyclopropyl-1-[[3-{5-[6-(1-hydroxy-1-methylethyl)pyridin-3-yl]pyridin-3-yl}phenyl]]-1,4-dihydro[1,8]naphthyridin-4-one-3-carboxamide from Example 58 for 5-bromo-2-(1-hydroxy-1-methylethyl)pirydine, and using 1.6 eq. of m-chloroperoxybenzoic acid, the title compound was obtained as a white solid.

¹H NMR (DMSO-d₆) δ 0.57 (m, 2H), 0.78 (m, 2H), 2.91 (m, 1H), 6.94 (s, 1H, OH), 7.65 (m, 1H), 7.71-7.79 (m, 3H), 7.97 (dd, 1H), 8.13 (d, 1H), 8.25 (s, 1H), 8.55 (s, 1H), 8.74 (dd, 1H), 8.80 (m, 1H), 8.87 (s, 1H), 8.91 (s, 1H), 9.00 (s, 1H), 9.09 (s, 1H), 9.73 (br, NH).

Example 70

N-Cyclopropyl-1-[[3-{5-[6-(1-hydroxy-1-methylethyl)pyridin-3-yl]-1-oxidopyridin-3-yl}phenyl]]1,4-dihydro[1,8]naphthyridin-4-one-3-carboxamide

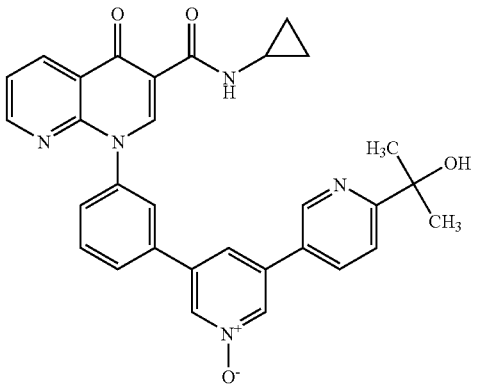

From the procedure of Example 69, the title compound was also obtained as a white solid.

¹H NMR (DMSO-d₆) δ 0.57 (m, 2H), 0.79 (m, 2H), 2.92 (m, 1H), 5.32 (s, 1H, OH), 7.65 (m, 1H), 7.72-7.80 (m, 3H), 8.08-8.17 (m, 2H), 8.27 (m, 2H), 8.70-8.82 (m, 4H), 8.88 (s, 1H), 8.98 (s, 1H), 9.73 (br, NH).

Example 71

N-Cyclopropyl-1-[[3-{5-[6-(1-hydroxy-1-methylethyl)-1-oxidopyridin-3-yl]-1-oxidopyridin-3-yl}phenyl]]-1,4-dihydro[1,8]naphthyridin-4-one-3-carboxamide

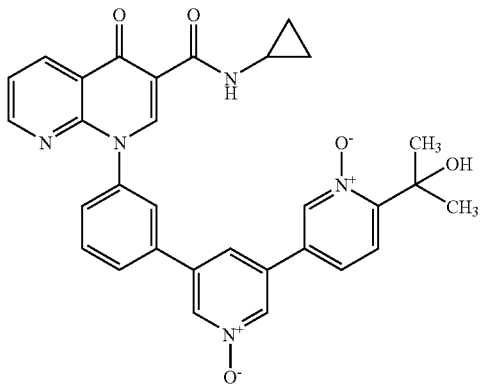

From the procedure of Example 69 the title compound was also obtained as a white solid.

$^1$H NMR (DMSO-$d_6$) δ 0.58 (m, 2H), 0.80 (m, 2H), 2.92 (m, 1H), 6.85 (brs, 1H, OH), 7.65 (m, 1H), 7.70-7.80 (m, 3H), 7.96 (d, 1H), 8.13 (m, 2H), 8.29 (s, 1H), 8.71-8.84 (m, 4H), 8.89 (s, 1H), 8.92 (s, 1H), 9.73 (br, NH).

Example 72

N-Isopropyl-1-[3-(1-oxidoquinolin-3-yl)phenyl]-1,4-dihydro[1,8]naphthyridin-4-one-carboxamide

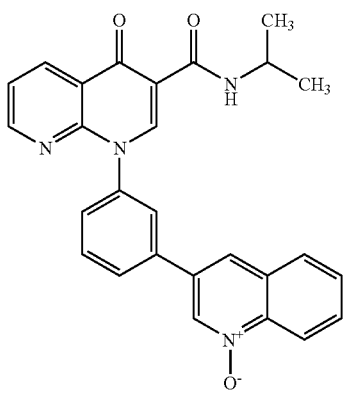

Following the procedure of Step 2 of Example 30, but substituting N-isopropyl-1-[3-(quinolin-3-yl)phenyl]-1,4-dihydro[1,8]naphthyridin-4-one-carboxamide from Example 12 for 5-bromo-2-(1-hydroxy-1-methylethyl)pirydine, the title compound was obtained as a solid.

$^1$H NMR (CDCl$_3$) δ 1.30 (d, 6H), 4.28 (m, 1H), 7.49 (dd, 1H), 7.54 (d, 1H), 7.66-7.85 (m, 5H), 7.92 (m, 2H), 8.69-8.75 (m, 2H), 8.84 (d, 1H), 8.86 (s, 1H), 9.08 (s, 1H), 9.64 (br, NH).

Example 73

N-Isobutyl-1-{3-[6-(1-hydroxy-1-methylethyl)-1-oxidopyridin-3-yl]phenyl}-1,4-dihydro[1,8]naphthyridinone-3-carboxamide

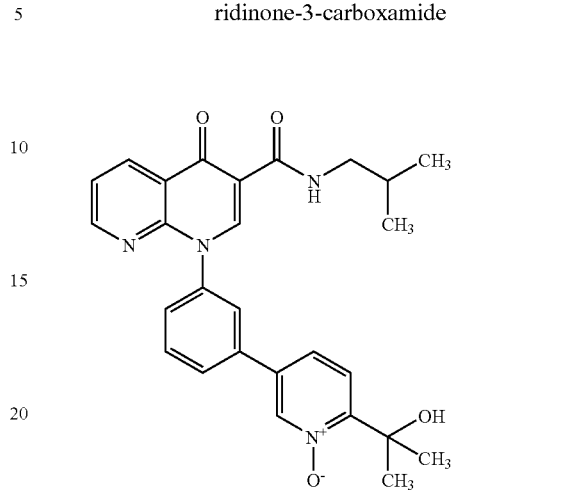

To a mixture of N-isobutyl-1-{3-[6-(1-hydroxy-1-methylethyl)pyridin-3-yl]phenyl}-1,4-dihydro[1,8]naphthyridin-4-one-3-carboxamide from Example 46 in 13:1 methylene chloride/methanol (33 ml/mmol) at room temperature was added magnesium monoperoxyphthalate hexahydrate (MMPP, 1.1 molareq) and the resulting mixture was stirred at room temperature for 24 hours. The mixture was filtered through a bed of celite and the filtrate was washed with aqueous sodium carbonate, then water and dried. The crude product was chromatographed on silica gel eluting with 8% ethanol in ethyl acetate and the solid obtained was stirred at room temperature in ether for several hours and filtered to afford the title compound as a light pink solid.

$^1$H NMR (Acetone-$d_6$) δ 0.98 (d, 6H), 1.61 (s, 6H), 1.88 (m, 1H), 3.26 (t, 2H), 7.52 (s, 1H, OH), 7.61 (m, 1H), 7.66 (d, 1H), 7.77-7.82 (m, 2H), 7.88 (d, 1H), 7.99 (d, 1H), 8.12 (s, 1H), 8.68 (s, 1H), 8.73 (m, 1H), 8.80 (dd, 1H), 8.93 (s, 1H), 9.81 (br, NH).

Example 74

N-Cyclopropyl-1-[3-(6-methyl-1-oxidopyridin-3-yl)]phenyl]-1,4-dihydro[1,8]naphthyridin-4-one-3-carboxamide

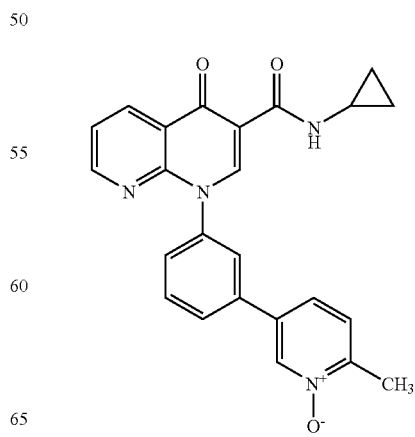

Following the procedure of Example 73, but substituting N-cyclopropyl-1-[3-(6 3-methylpyridin-3-yl)]phenyl]-1,4-dihydro[1,8]naphthyridin-4-one-3-carboxamide from Example 39 for N-isobutyl-1{[3-[6-(1-hydroxy-1-methylethyl)pyridin-3-yl]phenyl}-1,4-dihydro[1,8]naphthyridin-4-one-3-carboxamide, the title compound was obtained as a solid.

$^1$H NMR (CDCl$_3$) δ 0.72 (m, 2H), 0.91 (m, 2H), 2.61 (s, 3H), 3.02 (m, 1H), 7.38 (d, 1H), 7.45 (dd, 1H), 7.49-7.58 (m, 2H), 7.66 (s, 1H), 7.75 (m, 2H), 8.61 (s, 1H), 8.72 (m, 1H), 8.87 (dd, 1H), 9.08 (s, 1H), 9.78 (br, NH).

Example 75

N-Cyclopropyl-1-[3-(6-methylsulfonyl-1 oxidopyridin-3-yl)phenyl]-1,4-dihydro [18]naphthyridin-4-one-3-carboxamide

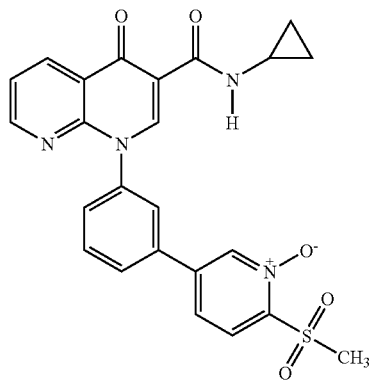

To a suspension of N-cyclopropyl-1-[3-(6-methylsulfonylpyridin-3-yl)phenyl]-1,4-dihydro[1,8]naphthyridin-4-one-3-carboxamide from Example 51 in methylene chloride (30 ml/mmol) was added urea-hydrogen peroxide (8 eq) and the resulting mixture was cooled to 0° C. Trifluoroacetic acid (4.7 eq) was added and the mixture was warmed to room temperature as a solution was obtained. After 18 hours, more urea-hydrogen peroxide (2.6 eq) and trifluoroacetic acid (2 eq) were added and stirring was continued for 2 hours. The mixture was quenched with saturated aqueous sodium metabisulfite, diluted with methylene chloride and the organic phase was washed with 1N aqueous HCl, then brine and water, dried and evaporated. The crude product was chromatographed on silica gel eluting with 40% toluene in acetone to afford the title compound as a solid.

$^1$H NMR (CDCl$_3$) δ 0.66 (m, 2H), 0.85 (m, 2H), 2.97 (m, 1H), 3.52 (s, 3H), 7.48 (m, 1H), 7.58-7.65 (m, 3H), 7.72-7.78 (m, 2H), 8.15 (d, 1H), 8.54 (s, 1H), 8.68 (brs, 1H), 8.81 (d, 1H), 9.01 (s, 1H), 9.71 (br, NH).

Example 76

N-Cyclopropyl-1-{5-bromo-3-[6-(1-hydroxy-1-methylethyl)-1-oxidopyridin-3-yl]phenyl}-4-1-dihydro [1,8]naphthyridin-4-one-3-carboxamide

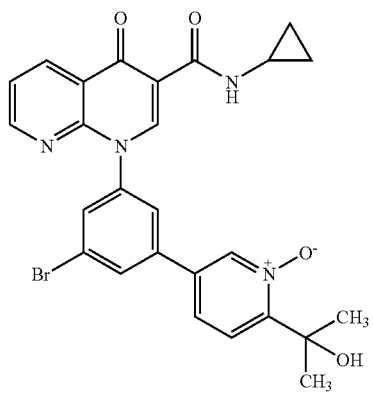

Following the procedure of Step 2 of Example 30, but substituting N-cyclopropyl-1-{5-bromo-3-[6-(1-hydroxy-1-methylethyl)pyridin-3-yl]phenyl}-1,4-dihydro[1,8]naphthyridin-4-one-3-carboxamide from Example 47 for 5-bromo-2-(1-hydroxy-1-methylethyl)pirydine, the title compound was obtained as a solid.

$^1$H NMR (CDCl$_3$) δ 0.71 (m, 2H), 0.90 (m, 2H), 1.75 (s, 6H), 3.02 (m, 1H), 7.48-7.60 (m, 5H), 7.73 (s, 1H), 7.88 (s, 1H), 8.52 (s, 1H), 8.72 (m, 1H), 8.84 (dd, 1H), 9.04 (s, 1H), 9.71 (br, NH).

Example 77

N-Cyclopropyl-1-{3-[6-(1,2-dihydroxy-1-methylethyl)-1-oxidopyridin-3-yl]phenyl}1-1,4-dihydro[1,8]naphthyridinone-3-carboxamide

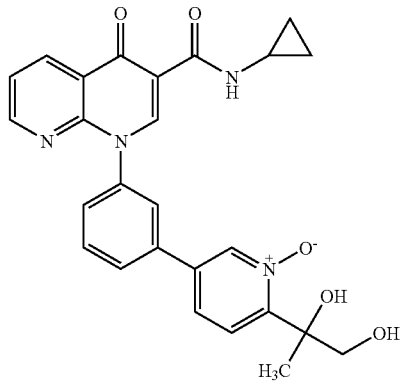

Step 1: 5-Bromo-2-(1-methylvinyl)pyridine N-oxide

A mixture of 5-bromo-2-(1-hydroxy-1-methylethyl)pyridine N-oxide from step 2 of example 30 (1.29 g) and 25% aqueous sulfuric acid was heated at 130° C. for 2 days. After cooling, the mixture was made slightly basic using 10N aqueous sodium hydroxide and partitioned between ethyl acetate and water. The crude product from evaporation of the organic phase was used as such in step 2.

Step 2: 5-bromo-2-(1,2-dihydroxy-1-methylethyl)pirydine N-oxide

The crude product from step 1 was dissolved in a 3:1 mixture of acetone and water (16 mL) and 4-methylmorpholine N-oxide (1 g) and potassium osmate dihydrate (90 mg) were added. The resulting mixture was stirred at room temperature for 3 days then excess solid sodium bisulfite was added and the mixture was evaporated. The residue was diluted with methylene chloride and filtered. The filtrate was evaporated and the residue chromatographed on silica gel eluting with ethyl acetate to afford the title compound as a white solid.

Step 3: N-Cyclopropyl-1-{3-[6-(1,2-dihydroxy-1-methylethyl)-1-oxidopyridin-3-yl]phenyl}-1,4-dihydro[1,8]naphthyridin-1-one-3-carboxamide Following the procedure of step 2 of example 32 but substituting 5-bromo-2-(1,2-dihydroxy-1-methylethyl)pyridine N-oxide from step 2 for 3-bromo-5-methylsulfonylpyridine the title compound was obtained as a white solid.

$^1$H NMR (CDCl$_3$) δ 0.66 (m, 2H), 0.85 (m, 2H), 1.61 (s, 3H), 2.78 (m, 1H, OH), 2.97 (m, 1H), 3.90 (m, 1H), 3.97 (m, 1H), 7.48 (m, 1H), 7.53 (m, 2H), 7.60 (m, 2H), 7.69-7.72 (m, 2H), 7.92 (s, 1H, OH), 8.49 (s, 1H), 8.68 (m, 1H), 8.80 (dd, 1H), 9.02 (s, 1H), 9.73 (br, NH).

PDE4 INHIBITOR EXAMPLE B

N-Cyclopropyl-1-{3-[(1-oxidopryidin-3-yl)ethynyl]phenyl}-4-oxo-1,4-dihydro-1,8-naphthyridine-3-carboxyamide (Compound IX)

Step 1:

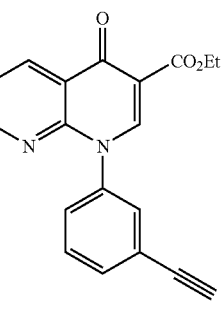

Va

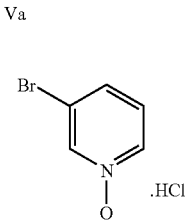

VII

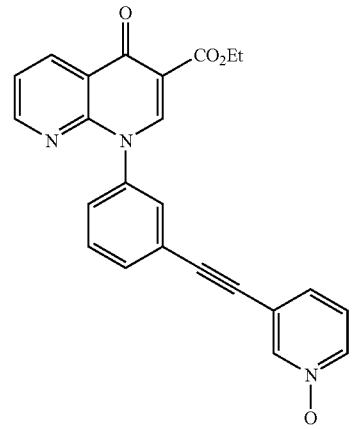

VIII

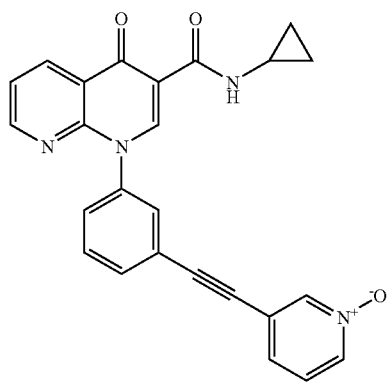

IX

| Materials | MW | Amount | Moles | Eq |
|---|---|---|---|---|
| Ethyl ester naphthyridone-phenylacetylene | 318.33 | 2.50 Kg | 7.85 | 1.0 |
| 3-Bromopyridine-N-oxide HCl salt | 210.46 | 1.82 Kg | 8.64 | 1.1 |
| Tert-amylamine | 87.17 d = 0.746 | 2.7 L | 45.6 | 3.0 |
| Allylpalladiumchloride dimer | 365.85 | 72 g | 0.2 | 2.5 mol % |
| Tri-t-butylphosphine | 10% in hexanes (0.33 M) | 2.38 L | 0.8 | 10 mol % |
| Dimethylaminoacetamide (DMAc) | solvent | 60 L | — | 24 vol |
| water | anti-solvent | 90 L | — | 36 vol |
| n-Butanol | rinse solvent | 87.6 L | — | 35 vol |

A 100 L round bottom flask was equipped with a reflux condenser and nitrogen sweep, and charged with bromopyridine-N-oxide HCl salt, followed by DMAc 12.5 L, and cooled with ice bath. Neat t-amylamine was added via dropping funnel over 1 hour. Addition of amine was noted to be mildly exothermic: temperature rose from 5° C. to 10° C. The phosphine solution was added to produce a light yellow, homogeneous solution. Next, the π-allylpalladium dimer was added as a slurry in DMAc 1.5 L. The reaction was allowed to stir at 10° C. for 30 minutes. The acetylene compound was weighed out into a carboy and DMAc 9.9 Kg added. This acetylene solution was added into the reaction flask. The carboy was rinsed with DMAc 22 Kg and added to the reaction mixture. Enough DMAc was added to achieve a total of 60 L. This milky yellow solution was heated to 60° C., becoming a homogeneous brown solution, until reaction was complete, judged by consumption of the acetylene compound. The reaction was cooled to 0° C. before adding water 90 L to precipitate product from solution. The slurry was filtered to collect product. To remove palladium, the cake was washed with 87.5 L of n-butanol on the filter pot, and then dried in vacuum oven at 50° C. under nitrogen stream overnight to give white solids 2.68 Kg, 83% yield NMR $^1$H (CDCl$_3$ 400 MHz) δ: 1.35 (t, J=7.1 Hz, 3H), 4.34 (q, J=7.1, 2H), 7.28 (dd, J=8.0, 6.8 Hz, 1H), 7.34 (dT, J=8.0, 1.2 Hz, 1H), 7.38 (dd, J=8.0, 4.4 Hz, 1H), 7.49 (ddd, J=8.0, 2.4, 1.2 Hz, 1H), 7.58 (t, J=7.9 Hz, 1H), 7.64 (t, J=1.8 Hz, 1H), 7.67 (dt, J=7.6, 1.2 Hz, 1H), 8.12 (dt, J=6.5, 1.1 Hz, 1H), 8.27 (s, 1H), 8.59 (dd, J=4.4, 1.9 Hz, 1H), 8.64 (s, 1H), 8.74 (dd, J=8.0, 1.9 Hz, 1H).

NMR $^{13}$C (CDCl$_3$ 400 MHz) δ: 14.3, 61.1, 84.7, 92.4, 112.8, 121.4, 122.7, 123.0, 123.2, 125.8, 128.3, 128.5, 129.8, 130.7, 132.5, 136.8, 139.1, 141.0, 149.0, 149.9, 152.5, 164.6, 174.5.

An alternative method of Palladium reduction has also been used and is as follows:

| Materials | MW | Amount | Moles | Eq |
|---|---|---|---|---|
| Ester product | 411.14 | 0.718 Kg | 7.85 | 1.0 |
| Darco G-60 | — | 0.359 Kg | — | 50 wt % |
| Methanol | solvent | 82 L | — | 50 vols |

After precipitation with water, the wet filter cake was dried under a nitrogen stream. A 100 L round bottom flask was equipped with a reflux condenser, stir paddle, and nitrogen sweep, then charged with the ester product and methanol 72 L. Mixture was heated to 60° C. until solids dissolved. Mixture was cooled to 55° C. and Darco G-60 was added as a slurry in 6 L methanol. Mixture was heated back to 60° C. for four hours. The solution was filtered through Solka Floc while warm to remove Darco. Solka Floc pad was rinsed with another 4 L of methanol. Combined filtrates were concentrated to 25 L volume, at which point a copious white precipitate was noted. This slurry can be carried forward into the amide formation step directly.

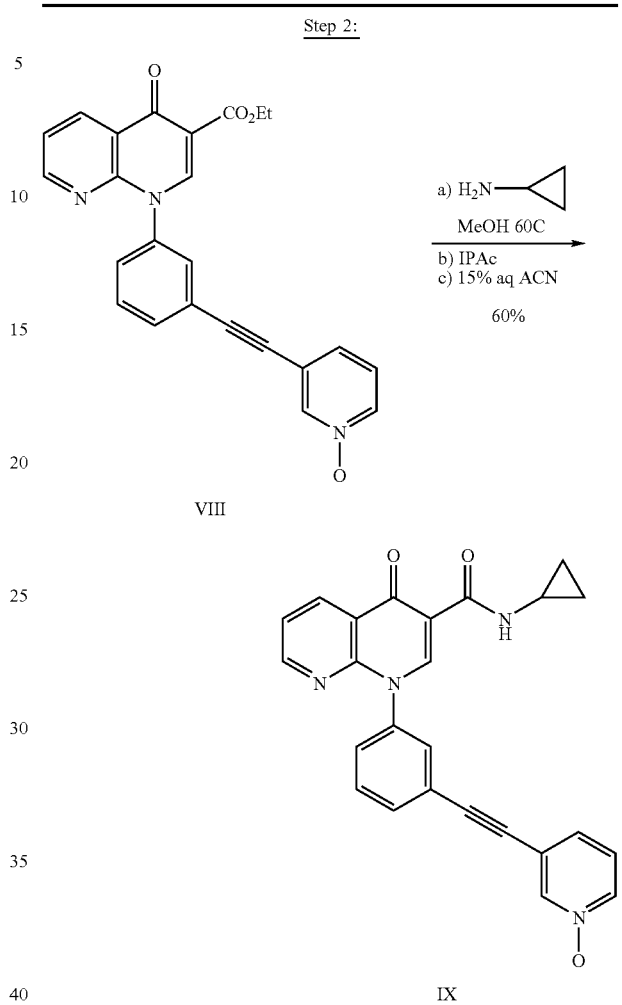

VIII

IX

| Materials | MW | Amount | Moles | Eq |
|---|---|---|---|---|
| Penultimate ester | 411.41 | 1.4 Kg | 3.4 | 1.0 |
| Cyclopropylamine | 57.10, d = 0.824 | 21 L | — | 15 vols |
| (Butylphosphite) | 250, d = 0.915 | 46 mL | 0.17 | 5 mol %)* |
| Methanol | solvent | 21 L | — | 15 vols |
| Isopropyl acetate | anti-solvent | 72 L | — | — |
| 15% aq. acetonitrile | solvent | 24 L | — | 24 vols |

In-line filter, 1 micron
*Note that the parentheses around the butylphosphite data indicate that the experiment was run both with and without the butylphosphite.

A 100 L round bottom flask was equipped with a reflux condenser and nitrogen sweep, and charged with penultimate ester and methanol followed by cyclopropylamine. As indicated above, catalyst or Lewis acid can be added. The reaction was heated to 60° C. until consumption of the ester. The reaction was judged to be complete when esters were less than 2% by HPLC. Upon completion, the reaction was allowed to cool to 40° C. and concentrated to ~half volume. Isopropyl acetate was added while distilling out the remainder of the methanol and amine. After completion of the solvent switch to isopropyl acetate, the final volume was 20 L. The slurry was sampled and filtered. The cake was washed with 2 L of isopropyl acetate and then dried in vacuum oven at 50° C. under nitrogen stream overnight.

A 72 L round bottom flask was equipped with a reflux condenser and nitrogen sweep, and charged with Compound IX product solids and 24 L 15% aq. acetonitrile. The Slurry was heated to 60° C. All solids went into solution. Batch solution was filtered through a 1 micron in-line filter while warm into a second 72 L round bottom flask, then allowed to cool to 22° C. The slurry was filtered and solids dried in vacuum oven at 50° C. under nitrogen stream overnight to give 0.86 Kg of crystallized Compound IX, 60% yield.

NMR $^1$H (CDCl$_3$ 400 MHz) δ: 0.61-0.73 (m, 2H), 0.79-0.92 (m, 2H), 2.95-3.01 (m, 1H), 7.28 (dd, J=8.0, 6.8 Hz, 1H), 7.40 (d, J=8.0 Hz, 1H), 7.48 (dt) J=8.0, 4.4 Hz, 1H), 7.49 (ddd, J=8.0, 2.0, 1.2 Hz, 1H), 7.61 (t, J=8.0 Hz, 1H), 7.64 (m, J=2.0 Hz, 1H), 7.71 (dt, J=7.6, 1.2 Hz, 1H), 8.19 (d, J=6.6, 1H), 8.34 (s, 1H), 8.70 (dd, J=4.6, 1.8 Hz, 1H), 8.80 (dd, J=8.0, 1.9 Hz, 1H), 9.00 (s, 1H), 9.74 (br d, J=3.6 Hz, 1H).

NMR $^{13}$C (CDCl$_3$ 400 MHz) δ: 6.5, 22.4, 84.6, 92.5, 113.5, 121.4, 122.0, 122.9, 123.2, 125.7, 128.4, 128.6, 129.8, 130.7, 132.6, 136.4, 139.0, 140.4, 141.1, 148.0, 149.7, 153.0, 165.1, 177.1.

Alternative Procedure Illustrating Amide Formation with Magnesium Chloride

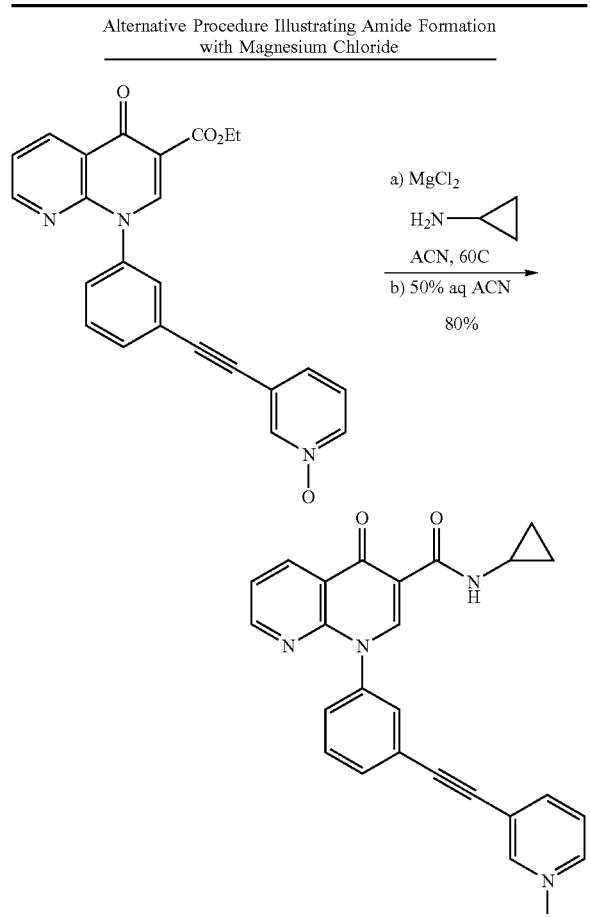

| Materials | MW | Amount | Moles | Eq |
|---|---|---|---|---|
| Penultimate ester | 411.41 | 1.0 Kg | 2.43 | 1.0 |
| Magnesium chloride | 95.22 | 0.231 Kg | 2.43 | 1.0 |
| Cyclopropylamine | 57.10, d = 0.824 | 10 L | — | 10 vol |
| Acetonitrile | solvent | 30 L | — | 30 vol |
|  |  | 16 L |  | 16 vol |
| Water | solvent | 8 L | — | 8 vol |
| sodium citrate | 294.10 | 0.79 Kg | 2.67 | 1.1 |

In-line filter, 1 micron

Process Description

A 72 L round bottom flask was equipped with a reflux condenser and nitrogen sweep, and charged with penultimate ester and acetonitrile followed by magnesium chloride and then cyclopropylamine. Reaction was heated to 60° C. until complete consumption of ester. Reaction was judged complete when esters were less than 0.5% by HPLC. Upon completion, reaction was allowed to cool to 40° C. and concentrated to ~half volume. Acetonitrile was added while distilling out remainder of cyclopropylamine. After complete solvent switch to acetonitrile, final volume was 8 L. Water 8 L was added and slurry was heated to 60° C. All solids went into solution. Batch solution was filtered through a 1 micron in-line filter while warm into a 22 L round bottom flask, then allowed to cool to 22° C. Slurry was filtered and solids dried in vacuum oven at 50° C. under nitrogen stream overnight to give 0.82 Kg of '191, 80% yield.

Step 3: Recrystalization of Compound IX

| Materials | MW | Amount | Moles | Eq |
|---|---|---|---|---|
| Compound IX | 422.45 | 0.86 Kg | 2.0 | 1.0 |
| Ethanol | solvent | 20 L | — | 4.3 vols |

A 72 L round bottom flask was equipped with a reflux condenser and nitrogen sweep, and charged with Compound IX and ethanol. Slurry was heated to 50° C. with stirring until recrystallization was complete. Recrystallization was judged to be complete when greater than 95% Form A by solid-state NMR and/or powder diffraction X-ray. The batch was allowed to cool to 22° C., then filtered to collect white solids which were dried in a vacuum oven at 50° C. under a nitrogen stream overnight to give 0.74 Kg of the desired form. The solids were co-milled through a size 12 mesh to provide fluffy white solids 0.719 Kg.

PDE-4 INHIBITOR EXAMPLE 2

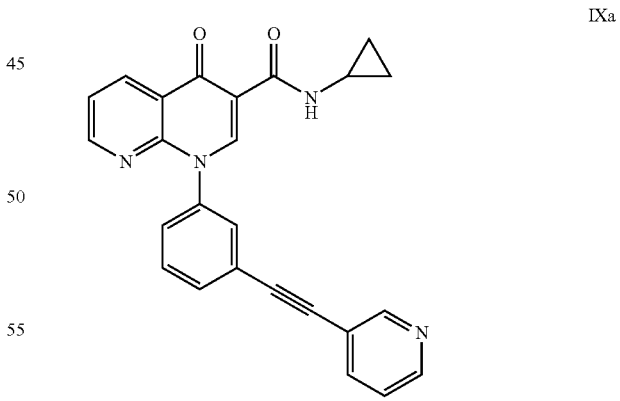

N-Cyclopropyl-1-{3-[(pryidin-3-yl)ethynyl]phenyl}1,4-oxo-1,4-dihydro-1,8-naphthyridine-3-carboxyamide (Compound IXa)

Compound IIa was prepared by following the procedure as described for Example 1, with the exception that 3-bromopyridine was substituted for 3-bromopyridine-N-oxide.

Other variations or modifications, which will be obvious to those skilled in the art, are within the scope and teachings of this invention. This invention is not to be limited except as set forth in the following claims.

What is claimed is:

1. A method of preparing a compound of preparing a compound of the formula IX and Formula IXa:

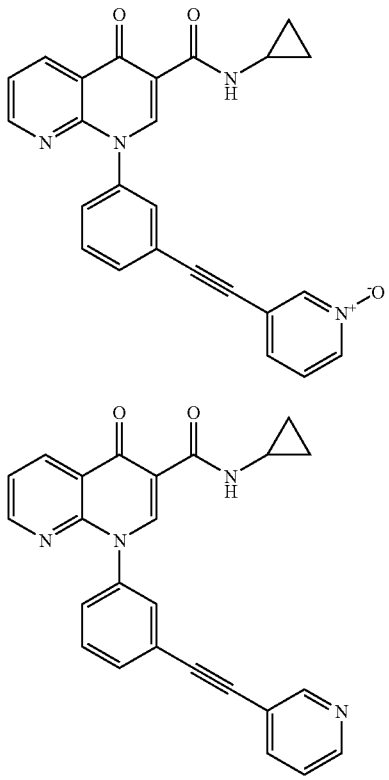

comprising

Step C: reacting, in solvent A, a compound of Formula Va

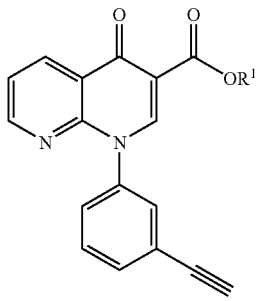

wherein
$R^1$ is selected from the group consisting of $C_{1-8}$ alkyl, aryl, and heteroaryl; optionally substituted with aryl and/or $C_{1-8}$ alkyl,
solvent A is dimethylaminoacetamide, dimethylformamide, acetonitrile, DMSO, methylacetamide, ethers or mixtures thereof;
with a compound of Formula VII or Formula VIIa

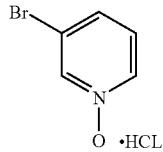

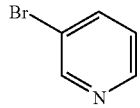

in the presence of a palladium catalyst and a phosphine ligand in amine base to yield a compound of Formula VIII or Formula VIIa

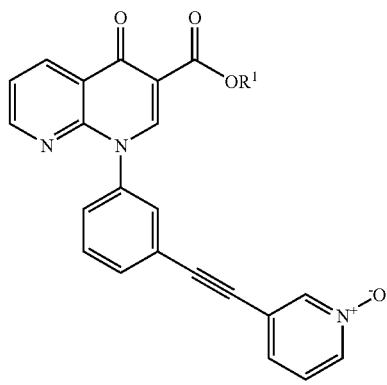

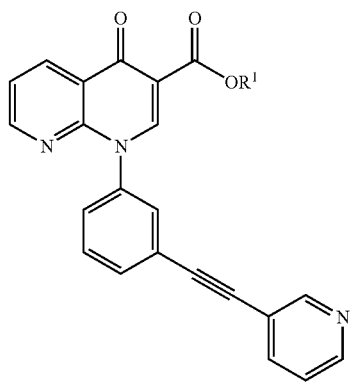

Step D: reacting, in solvent B, a compound of Formula VIII or VIIIa with cyclopropylamine optionally in the presence of a catalyst to yield a compound of Formula IX or IXa.

2. A method according to claim 1 wherein the phosphine ligand is $P(C_{1-6}alkyl)$.

3. A method according to claim 1 wherein the palladium catalyst is selected from the group consisting of, the palladium catalyst selected from $P(t-butyl)_3$-Pd—$P(t-butyl)_3$, $[PdCl(allyl)]_2$, $Pd_2(dba)_3$, and $[P(t-butyl)_3PdBr]_2$.

4. A method according to claim 1 wherein the molar ratio of the compound of Formula Va to Formula VII or VIIa is approximately 1:1.5 to 1.5 to 1.

5. A method according to claim 1 wherein the ratio of molar equivalents of amine base per mole of compound of Formula VII or VIIa is 2:1 to 3.5:1.

6. A method according to claim 1 wherein the molar ratio of Palladium catalyst to compound of Formula Va is 0.05:1 to 0.10:1.

7. A method according to claim 1 wherein step C is carried out at 40 to 70° C.

8. A method according to claim 1 wherein solvent B is a $C_{1-8}$ alkanol solvent or acetonitrile.

9. A method according to claim 1 wherein the catalyst is selected from Butyl phosphite $(BuO)_3P$ and magnesium chloride.

10. A method according to claim 1 wherein molar ratio of cyclopropylamine to compound of Formula VIII or VIIa is at least 1:1.

11. A method according to claim 1 wherein step D is carried out at 40 to 60°C.

12. A method according to claim 1 wherein reaction step C and reaction Step D are carried out in a single pot without purification or isolation of the product of Step C prior to proceeding with Step D.

13. A method claim 1 further comprising mixing compound of Formula IX with a conversion solvent to recrystallize the compound of Formula IX or IXa.

14. A method according to claim 13 wherein the conversion solvent is selected from dry ethanol, methanol, N-methylpyrrolidinone, trifluoroethanol, methyl t-butyl ether or mixtures thereof.

15. A method of purifying a compound of Formula IX or IXa

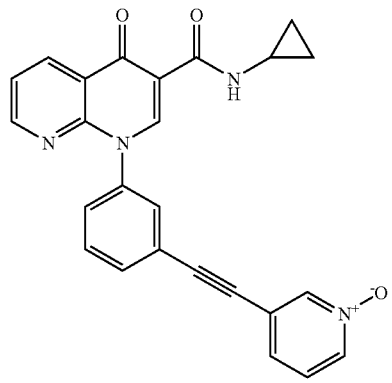

IX

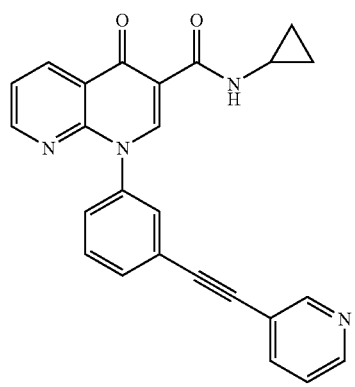

IXa comprising: combining a compound of Formula IX or IXa with an amount of a conversion solvent sufficient to suspend the compound and recrystallize said compound of Formula IX or IXa.

16. A method according to claim 15, wherein the conversion solvent is selected from dimethylformamide, dimethylacetamide, N-methylpyrrolidinone and C1-4alkanol.

17. A method according to claim 16, wherein the conversion solvent has a water content of less than 5%.

18. A method of preparing a compound of preparing a compound of the formula VIII and Formula VIIIa:

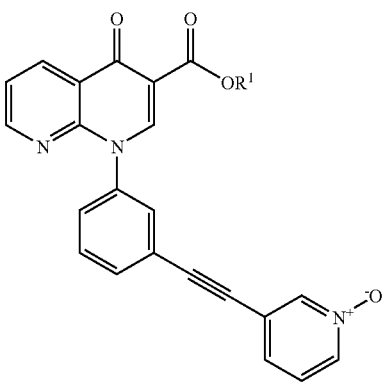

VIII

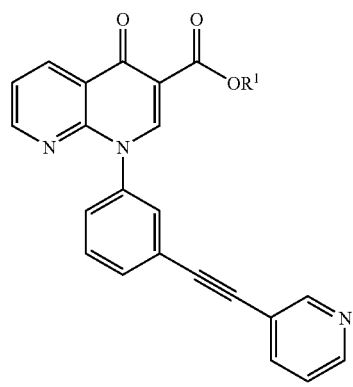

VIIIa comprising

Step C: reacting, in solvent A. a compound of Formula Va

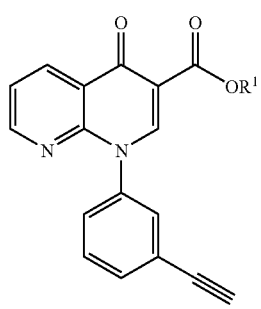

Va wherein

R[1] is selected from the group consisting of $C_{1-8}$ alkyl, aryl, and heteroaryl; optionally substituted with aryl and/or $C_{1-8}$ alkyl.

solvent A is dimethylaminoacetamide, dimethylformamide, acetonitrile, DMSO, methylacetamide, ethers or mixtures thereof;

with a compound of Formula VII or Formula VIIa

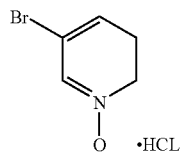

VII

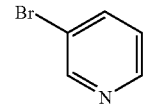

VIIa in the presence of a palladium catalyst and a phosphine ligand in amine base to yield a compound of Formula VIII or Formula VIIIa.

19. A method according to claim 18 wherein the phosphine ligand is P($C_{1-6}$alkyl) and the palladium catalyst is selected from the group consisting of, the palladium catalyst selected from P(t-butyl)$_3$-Pd—P(t-butyl)$_3$, [PdCl(allyl)]$_2$, Pd$_2$(dba)$_3$, and [P(t-butyl)$_3$PdBr]$_2$.

* * * * *